(12) United States Patent
Hudson et al.

(10) Patent No.: US 7,527,948 B2
(45) Date of Patent: May 5, 2009

(54) DETECTION OF HPV

(75) Inventors: Angela Hudson, Oregon, WI (US); Tamara Sander, Mazomanie, WI (US); Poonam Agarwal, Madison, WI (US); Michelle Garsha, Verona, WI (US); Hon Ip, Madison, WI (US); Robert W. Kwiatkowski, Jr., Hopewell Junction, NY (US); Vecheslav Elagin, Waunakee, WI (US); Marilyn Olson-Munoz, Middleton, WI (US); Michelle Curtis, Cottage Grove, WI (US); Sarah Olson, Cross Plains, WI (US); Ilse Tyler, Cottage Grove, WI (US)

(73) Assignee: Third Wave Technologies, Inc., Madison, WI (US)

(*) Notice: Subject to any disclaimer, the term of this patent is extended or adjusted under 35 U.S.C. 154(b) by 219 days.

(21) Appl. No.: 10/951,241

(22) Filed: Sep. 27, 2004

(65) Prior Publication Data

US 2007/0111200 A1    May 17, 2007

Related U.S. Application Data

(60) Provisional application No. 60/505,786, filed on Sep. 25, 2003.

(51) Int. Cl.
*C12P 19/34* (2006.01)
*C12Q 1/68* (2006.01)
*C07H 21/04* (2006.01)

(52) U.S. Cl. .................. 435/91.2; 435/6; 536/24.33
(58) Field of Classification Search ............... 435/91.2, 435/6; 536/24.33
See application file for complete search history.

(56) References Cited

U.S. PATENT DOCUMENTS

| | | | |
|---|---|---|---|
| 4,551,270 A | 11/1985 | Danos | |
| 4,849,331 A | 7/1989 | Lorincz | |
| 4,849,332 A | 7/1989 | Lorincz | |
| 4,849,334 A | 7/1989 | Lorincz | |
| 4,908,306 A | 3/1990 | Lorincz | |
| 5,057,411 A | 10/1991 | Lancaster | |
| 5,182,377 A | 1/1993 | Manos | |
| 5,283,171 A | 2/1994 | Manos | |
| 5,342,930 A | 8/1994 | Orth et al. | |
| 5,364,758 A | 11/1994 | Meijer et al. | |
| 5,411,857 A | 5/1995 | Beaudenon | |
| 5,447,839 A | 9/1995 | Bauer | |
| 5,484,699 A | 1/1996 | Bouma | |
| 5,501,947 A | 3/1996 | Emery | |
| 5,527,898 A | 6/1996 | Bauer | |
| 5,534,439 A | 7/1996 | Orth et al. | |
| 5,554,538 A | 9/1996 | Cole | |
| 5,580,970 A | 12/1996 | Hendricks | |
| 5,591,574 A | 1/1997 | Orth et al. | |
| 5,639,871 A | 6/1997 | Bauer | |
| 5,643,715 A | 7/1997 | Lancaster | |
| 5,648,459 A | 7/1997 | Cole et al. | |
| 5,656,423 A | 8/1997 | Orth | |
| 5,665,535 A | 9/1997 | Orth et al. | |
| 5,665,571 A | 9/1997 | Beaudenon | |
| 5,679,509 A | 10/1997 | Wheeler | |
| 5,681,944 A | 10/1997 | Crooke | |
| 5,705,627 A | 1/1998 | Manos | |
| 5,712,092 A | 1/1998 | Orth | |
| 5,783,412 A | 7/1998 | Morris | |
| 5,811,232 A | 9/1998 | Crooke | |
| 5,824,466 A | 10/1998 | Orth et al. | |
| 5,840,306 A | 11/1998 | Hofmann | |
| 5,863,717 A | 1/1999 | Lancaster | |
| 5,876,922 A | 3/1999 | Orth | |
| 5,888,724 A | 3/1999 | Silverstein | |
| 5,952,487 A | 9/1999 | Philipp et al. | |
| 5,958,674 A | 9/1999 | Beaudenon | |
| 5,981,173 A | 11/1999 | Orth | |
| 5,994,069 A | 11/1999 | Hall et al. | |
| 6,045,993 A | 4/2000 | Mahony | |
| 6,107,086 A | 8/2000 | Cole | |
| 6,127,164 A | 10/2000 | de Villiers et al. | |
| 6,159,729 A | 12/2000 | Hofmann et al. | |
| 6,218,104 B1 | 4/2001 | Morris | |
| 6,228,577 B1 | 5/2001 | Mahony | |
| 6,242,250 B1 | 6/2001 | Cole | |
| 6,265,154 B1 | 7/2001 | Kroeger | |
| 6,352,825 B1 | 3/2002 | Meijer et al. | |
| 6,420,106 B1 | 7/2002 | Gyllensten | |
| 6,458,940 B2 | 10/2002 | Robert | |
| 6,482,588 B1 | 11/2002 | Van Doorn | |
| 6,503,704 B1 | 1/2003 | Mahony | |
| 6,509,149 B2 | 1/2003 | Roberts | |

(Continued)

FOREIGN PATENT DOCUMENTS

EP    0342128 A1    11/1989

(Continued)

OTHER PUBLICATIONS

Ikenberg, Hans et al. Human Papillomavirus Type-16-Related DNA in Genital Bowen's Disease and in Bowenoid Papulosis. Int. J. Cancer. (1983), 32, 563-565.

(Continued)

*Primary Examiner*—Kenneth R. Horlick
*Assistant Examiner*—Cynthia B Wilder
(74) *Attorney, Agent, or Firm*—Casimir Jones S.C.

(57) ABSTRACT

The present invention provides compositions and methods for the detection and characterization of HPV sequences. More particularly, the present invention provides compositions, methods and kits for using invasive cleavage structure assays (e.g. the INVADER assay) to screen nucleic acid samples, e.g., from patients, for the presence of any one of a collection of HPV sequences. The present invention also provides compositions, methods and kits for screening sets of HPV sequences in a single reaction container.

10 Claims, 14 Drawing Sheets

U.S. PATENT DOCUMENTS

| | | | |
|---|---|---|---|
| 6,511,805 | B1 | 1/2003 | Gocke |
| 6,583,278 | B1 | 6/2003 | Carter |
| 6,613,557 | B1 | 9/2003 | Frazer |
| 6,649,167 | B2 | 11/2003 | Hallek |
| 6,858,412 | B2 | 2/2005 | Willis et al. |
| 2001/0049137 | A1 | 12/2001 | Cole et al. |
| 2002/0051968 | A1 | 5/2002 | Orth et al. |
| 2002/0155427 | A1 | 10/2002 | Cohenford et al. |
| 2003/0152942 | A1 | 8/2003 | Fors et al. |
| 2003/0152971 | A1* | 8/2003 | Lyamichev et al. ............ 435/6 |
| 2004/0170982 | A1* | 9/2004 | Morris et al. ................. 435/6 |

FOREIGN PATENT DOCUMENTS

| | | |
|---|---|---|
| EP | 0458668 A1 | 11/1991 |
| EP | 0192001 B1 | 3/1992 |
| EP | 0563255 B1 | 9/1994 |
| EP | 0342128 B1 | 4/1995 |
| EP | 0591376 B1 | 8/1998 |
| WO | WO 8303623 A1 | 10/1983 |
| WO | WO 8705630 A1 | 9/1987 |
| WO | WO 9109866 A1 | 7/1991 |
| WO | WO 9118118 A1 | 11/1991 |
| WO | WO 9211369 A1 | 7/1992 |
| WO | WO 9300435 A1 | 1/1993 |
| WO | 98/46793 A | 10/1998 |
| WO | WO0357914 * | 7/2003 |
| WO | 03/070977 A2 | 8/2003 |

OTHER PUBLICATIONS

Pfister, Herbert et al. Characterization of a Human Papillomavirus From Epidermodysplasia Verruciformis Lesions of a Patient From Upper-Volta. Int. J. Cancer. (1981), 27, 645-650.

Danos, Oliver et al. Molecular Cloning, Refined Physical Map and Heterogeneity of Methylation Sites of Papilloma Virus Type 1a DNA. Eur. J. Biochem. (1980), 109, 457-461.

Howley, Peter M. The Human Papillomaviruses. Arch Pathol Lab Med. (1982), 106, 429-432.

Lancaster, Wayne D. Human Papillomavirus: Detection of Viral DNA Sequences and Evidence for Molecular Heterogeneity in Metaplasias and Dysplasias of the Uterine Cervix. Intervirology. (1983), 20, 202-212.

Gissmann, Lutz et al. Presence of Human Papillomavirus in Genital Tumors. The Journal of Investigative Dermatology. (1984), 83, 26s-28s.

Allawi, Hatim T. et al. Thermodynamics and NMR of Internal G•T Mismatches in DNA. Biochemistry. (1997), 36, 10581-10594.

Murmur, J. et al. Strand Separation and Specific Recombination in Deoxyribonucleic Acids: Biological Studies. Proc. N. A. S. (1960), 46, 453-461.

Lyamichev, Victor et al. Polymorphism Identification and Quantitative Detection of Genomic DNA by Invasive Cleavage of Oligonucleotide Probes. Nature Biotechnology. (1999), 17, 292-296.

Lin, Paul Kong Thoo et al. Synthesis and Duplex Stability of Oligonucleotides Containing Cytosine-Thymine Analogues. Nucleic Acids Res., 1989, 17, 10373-10383.

Gissmann, L. Human Papillomavirus DNA In Genital Tumours. IARC Sci. Publ. 1984, 63, 405-411.

Crum, Christopher P., et al. Human Papillomavirus Type 16 and Early Cervical Neoplasia. The New England Journal of Medicine. Apr. 1984; 310(14):880-883.

Ostrow, Ronald S., et al. Molecular Cloning and Characterization of a Unique Type of Human Papillomavirus from an Immune Deficient Patient. The Journal of Investigative Dermatology. Apr. 1984; 82(4):362-366.

Orth, Gerard et al. Identification of Papillomaviruses in Butchers' Warts. The Journal of Investigative Dermatology. 1981; 76(2): 97-102.

Pfister, Herbert et al. Characterization of Human Papillomavirus 3 in Warts of a Renal Allograft Patient. The Journal of Investigative Dermatology. 1979; 73(5):349-353.

Potter, Harold L. et al. Nucleotide Sequence of Bovine Papillomavirus Type 2 Late Region. J. gen. Virol. (1985), 66, 187-193.

Coggins, L.W. et al. The Genomes of Bovine Papillomaviruses Types 3 and 4 are Colinear. J. gen. Virol. (1983), 64, 2771-2776.

Campo, M. Saveria et al. Molecular Cloning of Bovine Papillomavirus Genomes and Comparison of Their Sequence Homologies by Heteroduplex Mapping. J. gen. Virol. (1982), 63, 255-264.

Ostrow, Ronald S. et al. Identification of three distinct papillomavirus genomes in a single patient with epidermodysplasia verruciformis. J. Am. Acad. Dermatol. (1983), 8, 398-404.

Okagaki, T. et al. Identification of Human Papillomavirus DNA in Cervical and Vaginal Intraepithelial Neoplasia with Molecularly Cloned Virus-Specific DNA Probes. International Journal of Gynecological Pathology. (1983), 2, 153-159.

Lin, Paul Kong Thoo et al. Synthesis of Oligodeoxyribonucleotides Containing Degenerate Bases and Their Use as Primers in the Polymerase Chain Reaction. Nucleic Acids Research. (1992), 20(19), 5149-5152.

Schweitzer, Barbara A. et al. Aromatic Nonpolar Nucleosides as Hydrophobic Isosteres of Pyrimidine and Purine Nucleosides. J. Org. Chem. (1994), 59, 7238-7242.

Schweitzer, Barbara A. et al. Hydrophobic, Non-Hydrogen-Bonding Bases and Base Pairs in DNA. Journal of the American Chemical Society. (1995), 117, 1863-1872.

Rossi, John J. et al. An Alternate Method for Synthesis of Double-stranded DNA Segments. The Journal of Biological Chemistry. (1982), 257(16), 9226-9229.

Reynaldo, Luis P. et al. The Kinetics of Oligonucleotide Replacements. J. Mol. Biol. (2000), 297, 511-520.

Poljak et al., Journal of Clinical Virology, vol. 25, pp. S89-S97, 2002.

Vernon et al., BMC Infectious Diseases, vol. 3: 12 pp. 1-9, Jun. 2003.

Kleter et al., Journal of Clinical Microbiology, vol. 37, No. 8, pp. 2508-2517, Aug. 1999.

* cited by examiner

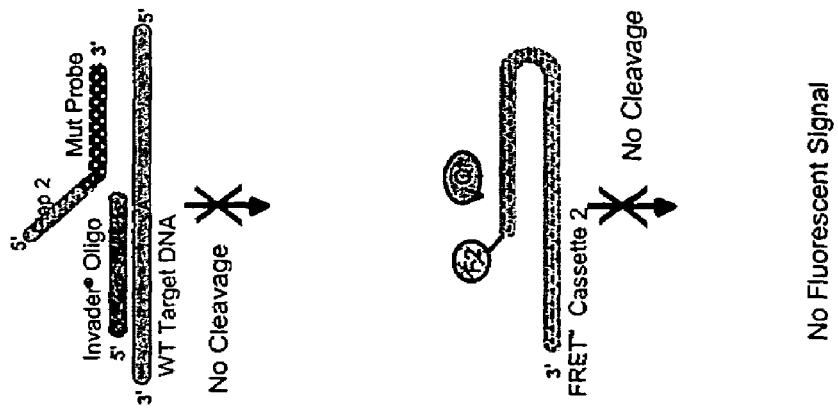
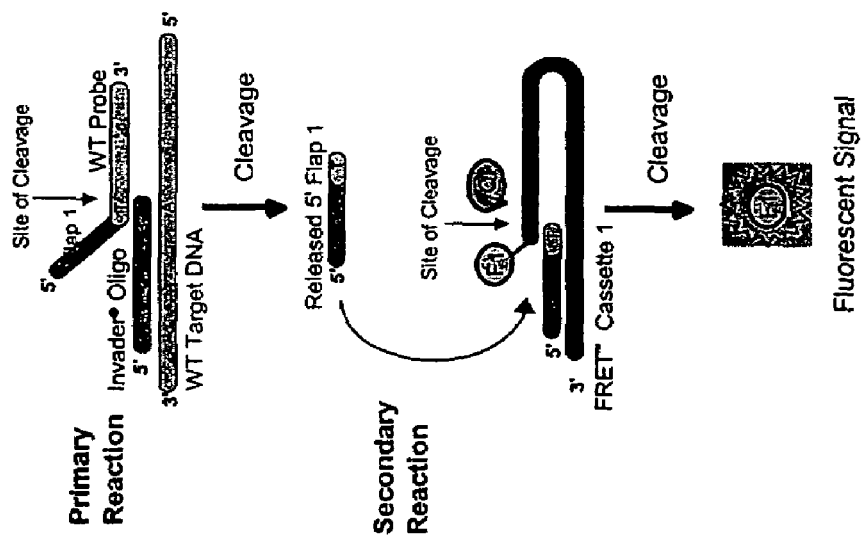
Fig. 1

|  | 18c1 | T3rT59 |
|---|---|---|
| Avg d1 | 443.0 | 361.3 |
| Avg d2 | 294.0 | 234.0 |
| Avg d3 | 200.5 | 181.8 |
| Avg d4 | 142.0 | 131.3 |
| Avg d5 | 118.0 | 115.0 |
| Avg d6 | 109.8 | 105.3 |
| Avg d7 | 98.3 | 96.3 |
| Avg NTC | 90.0 | 89.3 |
| %CV d1 | 2% | 5% |
| %CV d2 | 3% | 4% |
| %CV d3 | 3% | 9% |
| %CV d4 | 4% | 2% |
| %CV d5 | 5% | 3% |
| %CV d6 | 5% | 4% |
| %CV d7 | 3% | 2% |
| %CV NTC | 3% | 1% |

FOZ's calculated with NTC averages:
avg NTC 89.714  %CV NTC 2.5%

|  | 18c1 | T3rT59 | cp/rxn |
|---|---|---|---|
| FOZ d1 | 4.94 | 4.03 | 8000 |
| FOZ d2 | 3.28 | 2.61 | 4000 |
| FOZ d3 | 2.23 | 2.03 | 2000 |
| FOZ d4 | 1.58 | 1.46 | 1000 |
| FOZ d5 | 1.32 | 1.28 | 500 |
| FOZ d6 | 1.22 | 1.17 | 250 |
| FOZ d7 | 1.10 | 1.07 | 125 |

T-test from neighbors:

|  | 18c1 | T3rT59 | cp/rxn |
|---|---|---|---|
| d1 | 0.00000 | 0.00001 | 8000 |
| d2 | 0.00000 | 0.00065 | 4000 |
| d3 | 0.00000 | 0.00041 | 2000 |
| d4 | 0.00055 | 0.00025 | 1000 |
| d5 | 0.03254 | 0.00853 | 500 |
| d6 | 0.00326 | 0.00610 | 250 |
| d7 | 0.00291 | 0.00233 | 125 |

FIGURE 3

| | Oligo Name | Design | | Common Name | | Sequence | Target | | FRET |
|---|---|---|---|---|---|---|---|---|---|
| SEQ ID NO: 1 | 958504-1zp | A1g | Hex | A1g3P | probe oligo | cggccgagqGTCCGgTTCTgCTTGaCC | 16 | 31 | FRET 16 |
| SEQ ID NO: 2 | 958507-2ZI | A1g | | A1g10ci | INVADER oligo | CTTACACTGCCAACAAAAGGTTACGATATTGTAATGGATCTc | 16 | 31 | FRET 16 |
| SEQ ID NO: 3 | 797806-2ZI | A1g | | A1g18i | INVADER oligo | GTAGACTCACACTGCCAACAAAAGGTTACGATATTGTAATTGGATGTc | 16 | 31 | FRET 16 |
| SEQ ID NO: 4 | 1536733-4ZP | D2 | Hex | D2a2bp | probe oligo | cgcagtctgggagtCAACACAAACAGGgACCACAA | | 35 | AH 9 |
| SEQ ID NO: 5 | 1535672-2ZI | D2 | | D2a5i | INVADER oligo | gctccaacgggtttcctgcGCACAATATTAaACACACATTTACACGCCATGTAt | | 35 | AH 9 |
| SEQ ID NO: 6 | | | Hex | AH9FAM | FRET cassette | 5'(FAM)-TCT-(Z28)-AGCCGGTTTTCCGGCTGAGAACTCCAGACTGCC 3' | | | |
| SEQ ID NO: 7 | 1067594-22P | D3 | Hex | D3a2p | probe oligo | cgcagtctgggagtGTTGTATGACTATGGaGCACCG | | 35 | AH 9 |
| SEQ ID NO: 8 | 1535672-5ZI | D3 | | D3a5i | INVADER oligo | gctccaacgggtTCtgTAGCCATaAtGTGATGTGTGTTTTATAATTAACACTGTATTt | | 35 | AH 9 |
| SEQ ID NO: 9 | 1067596-12P | D5 | Hex | D5a1p | probe oligo | cgcagtctcgagtGAAGTGGACAGACCTTGTAAGGT | | 35 | AH 9 |
| SEQ ID NO: 10 | 1535672-8ZI | D5 | | D5a6i | INVADER oligo | agatgcgacaccaatccggcGACAATATTAaACACACATTTACACGCCATGTAt | | 35 | AH 9 |
| SEQ ID NO: 11 | 660504-32P | F3 | | F3e1 | probe oligo | cggccgaggtcaaCggtttctggcacc | 18 | 45 | FRET 16 |
| SEQ ID NO: 12 | 726636-6ZI | F3 | | F3e5i | INVADER oligo | gtcgttttcctaaggtgtctaagttttctgctgggta | 18 | 45 | FRET 16 |
| SEQ ID NO: 13 | 726636-7ZI | F3 | | F3e8i | INVADER oligo | gtcgtttgtcattaaggtgtctaagttttctgctggata | 18 | 45 | FRET 16 |
| SEQ ID NO: 14 | 614188-12P | F6 | Hex | F6a1b | probe oligo | cggccgagggtcctttgtgtgaccgtggt | 18 | 45 | FRET 16 |
| SEQ ID NO: 15 | 660449-1zi | F6 | | F6a4i | INVADER oligo | ggattgcgagcattacagcagctgtctggaamccctc | 18 | 45 | FRET 16 |
| SEQ ID NO: 16 | 660449-3zi | F6 | | F6a6i | INVADER oligo | gaccttcgagcactccagcagctgttttgagcacttc | 18 | 45 | FRET 16 |
| SEQ ID NO: 17 | 1067557-22P | G6b | Hex | G6b3P redesign Arm 1 | probe oligo | cggccgaggAGGGCAATAGGGtCGCCa | 51 | 82 | FRET 16 |
| SEQ ID NO: 18 | 1076582-22I | G6b | | G6b182-2 | INVADER oligo | ACAAATATAAACTGTGTGCTGCAAAAATGGGtt | 51 | 82 | FRET 16 |
| SEQ ID NO: 19 | 1076582-3ZI | G6b | | G6b151-2 | INVADER oligo | CAAGTGTGTGCAAGCCACAAATATGGGTt | 51 | 82 | FRET 16 |
| SEQ ID NO: 20 | 614174-12P | J4 | Hex | J4a1b | probe oligo | cgcgccgaggGTCCATCTGGCCagtGCa | 33 | 52 58 | FRET 16 |
| SEQ ID NO: 21 | 733068-2ZI | J4 | | J4a6i | INVADER oligo | CCCAAATATAATCACAATGCTgATGTAGTAATTGCTTATGGCTTGTTCTGCTTc | 33 | 52 58 | FRET 16 |
| SEQ ID NO: 22 | 733068-4ZI | J4 | | J4a8i | INVADER oligo | GTAGTAATCAGCTGTGGCCGGTTGTGTCTTc | 33 | 52 58 | FRET 16 |
| SEQ ID NO: 23 | 660427-22P | K10a | Hex | 1616-11-22P | probe oligo | CGCGCCGAGgGACCTTGTATGTCACGTGCAATTA | 39 | 68 | FRET 16 |
| SEQ ID NO: 24 | 958594-6ZI | K10a | | 1688-09-6ZI | INVADER oligo | TGCAAGAAATTGTTAGATTTATATCCATGCAATGAAATAGAGCCGGTCA | (39 & 68var) | | FRET 16 |
| SEQ ID NO: 25 | 958596-7ZI | K10a | | 1688-10-5ZI | INVADER oligo | AGGAAATTGTATTAGAGTTATGTCCTTACAATGAAATACAGCCGGTTc | (68 & 70) | | FRET 16 |
| SEQ ID NO: 26 | 726638-22P | L1b | Hex | L1b2p | probe oligo | cgcgccgaggGTGCACCTGGAgAGGATG | 39 | 59 | FRET 16 |
| SEQ ID NO: 27 | 958550-3ZI | L1b | | L1b61 (T39) | INVADER oligo | AGGGTGGAGATATGTATGCTGCCAAGTATTGTTGCAa | 39 | 59 | FRET 16 |
| SEQ ID NO: 28 | 958550-3ZI | L1b | | L1b8i (T39) | INVADER oligo | AGGGTGGAGATATAGATGTTGCCAAACTATTGTTGCAa | 39 | 59 | FRET 16 |
| SEQ ID NO: 29 | 958550-4ZI | L1b | | L1b9i (T59) | INVADER oligo | CCTATGCCTAAAAGCTGTTTATTACAAGGGTGGCGCCACCAAAGTTGTGCAAGTATTGTTAGAa | 39 | 59 | FRET 16 |
| SEQ ID NO: 30 | 865933-12P | P11b | Hex | 1662-38-12P | probe oligo | CGCGCCGAGGATGAGCAATTACGTGACAGCTC | 33 | 58 | FRET 16 |
| SEQ ID NO: 31 | 1076274-1ZI | P11b | | 1720-06-1ZI | INVADER oligo | CAGCCAAGCCAGGCGGCGTTGAGATTTATATCCTGTACCAACTGACCTATACTGCTT | -33 | | FRET 16 |
| SEQ ID NO: 32 | 1076274-2ZI | P11b | | 1720-06-2ZI | INVADER oligo | CAGCCAAGCCAGGCGGCGTAGATTTACATCCTGTACCAACTGACCTATTCTGCTT | -58 | | FRET 16 |
| SEQ ID NO: 33 | 1076274-3ZI | P11b | | 1720-06-3ZI | INVADER oligo | CAGCCAAGCCAGGCGGCGTATTTAGATTTACATCCTGTACCAATTGACCTATTCTGCT | (58iso) | | FRET 16 |
| SEQ ID NO: 34 | 1076274-4ZI | P11b | | 1720-06-4ZI | INVADER oligo | CAGCCAAGCCAGGCGGCGTTGCAACCTGTAACAACTGACCTACACTGCTT | 52 | | FRET 16 |
| SEQ ID NO: 35 | 1076274-5ZI | P11b | | 1720-06-5ZI | INVADER oligo | CAGCCAAGCCAGGCGGCGTAGATTTGCAACCAGTGACGAACTGATCTCTACTGTTT | 16Ty2 | | FRET 16 |

FIGURE 3

| SEQ ID NO: | | | | | | | | |
|---|---|---|---|---|---|---|---|---|
| SEQ ID NO: 36 | 958676-42P | R4 | Hex | R4d1b lot 2 | probe oligo | cgcgccgaggagcggaaccacaccgt | 45 | 59 | FRET 16 |
| SEQ ID NO: 37 | 660522-32I | R4 | | R4d4i | INVADER oligo | gggccataaataataattatcccacgcacaactaccggccgacc | 45 | 59 | FRET 16 |
| SEQ ID NO: 38 | 660522-42I | R4 | | R4d5i | INVADER oligo | gaggaagaaacgatcAACTAGATGGAGTTAATCATCAttgctactagctagacc | 45 | 59 | FRET 16 |
| SEQ ID NO: 39 | 660509-42P | T3 | | T3e1b | probe oligo | cgcgccgagggatcctcaaagcgAgcc | 18 | 59 | FRET 16 |
| SEQ ID NO: 40 | 660521-42I | T3 | | T3e4i | INVADER oligo | atcctgtgcacaaatcagtagcctgataggtctgtcgtgc | 18 | 59 | FRET 16 |
| SEQ ID NO: 41 | 660521-62I | T3 | | T3e6i | INVADER oligo | tgcacaaatcagcagcttgtaaggtcgttgtgtagc | 18 | 59 | FRET 16 |
| SEQ ID NO: 42 | 726593-42T | T3 | | T3rT59b | synthetic target | gcatggcacgcttgaggatcctacacacgaccatacacaaactgcctgattggcaccaacattga | 18 | 59 | FRET 16 |
| SEQ ID NO: 43 | 958514-32P | Y14 | Hex | Y14c3P | probe oligo | cgcgccgaggGCCCACTCTGCGCtTC | 56 | 66 | FRET 16 |
| SEQ ID NO: 44 | 958514-72P | Y14 | Hex | Y14d2P | probe oligo | cgcgccgaggGTAACTGCCCACTCTGCG | 56 | 66 | FRET 16 |
| SEQ ID NO: 45 | 958514-82P | Y14 | Hex | Y14d3P | probe oligo | cgcgccgaggGTAACGTGCCCtCTGC | 56 | 66 | FRET 16 |
| SEQ ID NO: 46 | 958514-92P | Y14 | Hex | Y14d4P | probe oligo | cgcgccgaggGTAACGTGCCCCTCTGC | 56 | 66 | FRET 16 |
| SEQ ID NO: 47 | 958514-52I | Y14 | | Y14c1i | INVADER oligo | CAACTGCTGCTTATGGGTGCGTTAACAGTAACGTc | 56 | 66 | FRET 16 |
| SEQ ID NO: 48 | 958514-102I | Y14 | | Y14d1i | INVADER oligo | GTACTACAGCTGCTTATGGGTGCGTTAACAc | 56 | 66 | FRET 16 |
| SEQ ID NO: 49 | 1574988-32P | W13 | Hex | W13a2bp | probe oligo | GGCAGTCTGGGAGT gtacgagcagttaatggc | 51 | | AH9 |
| SEQ ID NO: 50 | 1574989-42I | W13 | | W13a3ai | INVADER oligo | gctccaacgggttcctgcgcagtggagactcccttcgcgttC | 51 | | AH9 |
| SEQ ID NO: 51 | 1574988-42P | W13 | Hex | W13a3bp | probe oligo | CCAGTCTGCCAGT gtacagcagatgttatgggc | 51 | | AH9 |
| SEQ ID NO: 52 | 1574989-32I | W13 | | W13a2ci | INVADER oligo | agatggcgacaccaatccgggcagagagcaccccttcgcgttC | 51 | | AH9 |
| SEQ ID NO: 53 | 1708847-42P | 39B11 | Hex | 39B11a3b | probe oligo | ggcagtctgggagt GTCCATACCGATcGCGCGatt | 39 | | AH9 |
| SEQ ID NO: 54 | 1708847-52I | 39B11 | | 39B11a6i | INVADER oligo | AAACGGTTTcAACCGAAATCGGTGATTAAAAgGCAGTCACAGTTCTc | 39 | | AH9 |
| SEQ ID NO: 55 | 1708848-12P | 39B8 | Hex | 39B8a1b | probe oligo | ggcagtctgggagt gcaacatccattcctccaccta | 39 | | AH9 |
| SEQ ID NO: 56 | 1708848-32I | 39B8 | | 39B8a3i | INVADER oligo | CTTACTCATCATCCTGTCCAGGTGCCACTAcCAACAATACTTTGc | 39 | | AH9 |
| SEQ ID NO: 57 | 1708849-12P | 68B10 | Hex | 68B1Ca1b | probe oligo | ggcagtctgggagt agtaggcacacatcca | 68 | | AH9 |
| SEQ ID NO: 58 | 1708849-52I | 68B10 | | 68B10a6iD12 | INVADER oligo | cgtcccaagccgcaggcCGTGACTAATACCACATCCATt-AATTGTGCAACCGAAATc | 68 | | AH9 |
| SEQ ID NO: 59 | 1708850-12P | 68B5 | Hex | 68B5a4b | probe oligo | ggcagtctgggagt AGAAGGCAACTAgAACGGACa | 68 | | AH9 |
| SEQ ID NO: 60 | 1708850-32I | 68B5 | | 68B5a8i | INVADER oligo | TGGACCACCTTGCAtGACtTTACAATAGACTGTGTCTATTGCc | 68 | | AH9 |
| SEQ ID NO: 61 | 1575046-42P | O5b | Hex | O5b2p | probe oligo | ggcagtctgggagt GCAGCTTATTCTGaGTGACT | 56 | | AH9 |
| SEQ ID NO: 62 | 1708977-52I | O5b | | O5b2i | INVADER oligo | ACCGAAcGCGTTTATGACCCGAAAACGGTACATATAAAGc | 56 | | AH9 |
| SEQ ID NO: 63 | | | Hex | DM/FAM | FRET cassette | Y-tct-X-agc-cgg-ttt-tcc-ggc-tga-gac-ctc-ggc-gcg-hex | | |
| | | | | | | X = Quencher = Z28, Y = Dye = FAM | | |

| SEQ ID NO: 64 | | | Hex | alpha actin IC probe | probe oligo | ttcgcgctcc_AGGAACCCTGTGACAT |
| SEQ ID NO: 65 | | | | alpha actin Invader oligo | INVADER oligo | CCATCCAGGAAGAGTGGCCTGTTT |
| SEQ ID NO: 66 | | | hex | CFTR IC probe | probe oligo | tccgcgggtctgaggaagcaccaatcatg |
| SEQ ID NO: 67 | | | none | CFTR Invader oligo | INVADER oligo | tgtacttcatgctgtcacactaagagagaatgagagacacaca |

| SEQ ID NO: 68 | | | hex | CFTR & alpha actin FRET cassette | FRET cassette | Y-tct-X-tcg-gcc-ttt-tgg-ccg-aga-gag-gac-gcg-cgg-a-hex |
| SEQ ID NO: 69 | | | hex | hIGF probe | probe oligo | cgc_gcc_gag_g_ca_gca_ctc_atc_cac_ga |
| SEQ ID NO: 70 | | | | hIGF Invader oligo | INVADER oligo | cca gcc tcc tta gat cac agc tcc gga agt |
| SEQ ID NO: 71 | | | hex | hIGF FRET cassette | FRET cassette | Y-tct-X-tcg-gcc-ttt-tcg-ccg-aga-gag-tct-gcc-acg-tca-t-hex |
| | | | | | | *X=quencher, Z28, Y=dye, Z35 (RED dye) |
| SEQ ID NO: 72 | | | | B1f118 | synthetic target | tTCGGTTGCACAGCAAGATGAGGATTGTAGGATAAAATGATGCTGTAAGGTGTGCAGTTTTATAACTTGAt |
| SEQ ID NO: 73 | | | | B1b8i | INVADER oligo | tCTGCACACCTTACAGCATCCATTTTCTCCTACAATCCta |
| SEQ ID NO: 74 | | | | B1b9i | INVADER oligo | aCAAGTTATAAACTTGCATACTACACAGCATCCATTTTCTTATAATCCta |
| SEQ ID NO: 75 | | | | B1b10i | INVADER oligo | aGCATTTGCACATTATATGGCTCCATTTTCTCCTTTAAATCCta |
| SEQ ID NO: 76 | | | hex | B1b3 | probe oligo | cgcgccgaggCCATTTTGCAGTGCAACCG |

*T-dye, Z35 (RED dye)

FIGURE 6

A9 Pool

| Assay | Gene | HPV Strains Detected | | | | | | |
|---|---|---|---|---|---|---|---|---|
| | | 16 | 31 | 33 | 35 | 52 | 58 | 67 |
| J4 | E7 | | | 1 | | 1 | 1 | 1 |
| Z1 | L1 | | | 1 | | 1 | 1 | 1 |
| N12 | L1 | | 1 | | 1 | | | |
| AN1 | E7 | 1 | 1 | | 1 | | | |
| A3a | L1 | 1 | 1 | | | | | |
| Total Assays per strain | | 2 | 3 | 2 | 2 | 2 | 2 | 2 |

A7 Pool

| Assay | Gene | HPV Strains Detected | | | | | |
|---|---|---|---|---|---|---|---|
| | | 18 | 39 | 45 | 59 | 68 | 70 |
| T3 | E6 | 1 | | | 1 | | |
| K5 | E6 | | 1 | | | 1 | 1 |
| F11 | L1 | 1 | | 1 | | | |
| K15 | E6 | | 1 | | | 1 | 1 |
| R4 | E7 | | | 1 | 1 | | |
| Total Assays per Strain | | 2 | 2 | 2 | 2 | 2 | 2 |

A5/A6 Pool

| Assay | Gene | HPV Strains Detected | |
|---|---|---|---|
| | | 51 | 56 |
| W13 | E7 | 1 | |
| W17 | L1 | 1 | |
| O5 | LCR | | 1 |
| O12 | L1 | | 1 |
| Total Assays per Strain | | 2 | 2 |

FIGURE 7

| | Assay Name | Strains Detected by Assay | Gene | Oligo Type | Sequence (5'-3') | Oligo Name |
|---|---|---|---|---|---|---|
| | A5/A6 Pool | | | | | |
| SEQ ID NO: 77 | W13 | 51 | E7 | Probe | GGCAGTCTGGGAGTGTACAGCAGATGTTTATGGC | W13a3p |
| SEQ ID NO: 78 | | | | Invader | AGATGGCGACACCAATCCGGGCAGAGGAGACACCCTTCGCGTTC | W13a2ci |
| SEQ ID NO: 79 | W17 | 51 | L1 | Probe | GGCAGTCTGGGAGTGCTTAGCCTGTGTGGAAGGG | W17c3P |
| SEQ ID NO: 80 | | | | Invader | CGTTCCTTAGATCTACATTCCAAATTTATATTTGGCCAAAGGATCTGC | W17c1ci |
| SEQ ID NO: 81 | O5 | 56 | LCR | Probe | GGCAGTCTGGGAGTGCAGCTTATTCTGAGTGGACT | O5b2p |
| SEQ ID NO: 82 | | | | Invader | ACCGAAACGGGTTTATGACCGAAAACGGTACATATAAAAGC | O5b2i |
| SEQ ID NO: 83 | O12 | 56 | L1 | Probe | GGCAGTCTGGGAGTGTTCCTGCTGTTGTGGCTGTTACCG | O12a4P |
| SEQ ID NO: 84 | | | | Invader | GCTCCAACGGGTTTCCTGCCATCCCACAATTTATATTTAGCTAATGGGTCCTGTTTTCTC | O12a3ci |
| | A7 Pool | | | | | |
| SEQ ID NO: 85 | T3 | 18,59 | E6 | Probe | CGCGCCGAGGGATCCTCAAAGCGAGCC | T3e1b |
| SEQ ID NO: 86 | | | | Invader | ATTCTGTGCACAATCAGGTAGCTTGTAGGGTCGTCGTGTTGC | T3e4i |
| SEQ ID NO: 87 | | | | Invader | TGCACAAATCAGGCAGTTTGTAAGGTCGTTGTGTAGC | T3e6i |
| SEQ ID NO: 88 | R4 | 45,59 | E7 | Probe | CGCGCCGAGGGAGCGAACCACAGCGT | R4d1b |
| SEQ ID NO: 89 | | | | Invader | GGGCCATAAATAATAATTCCTCATGCACAACTACCGGCCGACC | R4d4i |
| SEQ ID NO: 90 | | | | Invader | GAGGAAGAAAAACGATGAACTAGATGGAGTTAATCATCATTTGCTACTAGCTAGACC | R4d5i |
| SEQ ID NO: 91 | F11 | 18,45 | L1 | Probe | CGCGCCGAGGGATTGGACAAAACGATATGTATCCA | F11a2 |
| SEQ ID NO: 92 | | | | Invader | GGTGTAGCATCCTTTTGACAGGTAATAGCAACAT | F11a3i |
| SEQ ID NO: 93 | | | | Invader | GGTGTAGTATCCTTTTGACAGGTAACAGCAACTT | F11a4i |
| SEQ ID NO: 94 | K15 | 39,68,70 | E6 | Probe | CGCGCCGAGGAGGAAGCTTTACAGGACAGTG | K15d1 |
| SEQ ID NO: 95 | | | | Invader | CTGAAACCGTTGAGTCCAGCAGAAAAATTAAGGCACCTAACTACCAAACGAAGATTTCATAAAATAGCC | K15d7i |
| SEQ ID NO: 96 | | | | Invader | CTGAAACCGTTGTGTCCAGCAGAGAAAATTAAGACACGTTAATACCAAACGAAGATTTCATCAAATAGCC | K15d8i |
| SEQ ID NO: 97 | K5 | 39, 68, 70 | E6 | Probe | CGCGCCGAGGGGTCCGGCAATTTGTATGGC | K5g2 |
| SEQ ID NO: 98 | | | | Invader | GTCTTGCAAGGTAGTGTCCAGCGCTGTGCACAC | K5g39i |
| SEQ ID NO: 99 | | | | Invader | GTAATGTCATGCAAGTGTGTCCAACGTCGTGCACAC | K5g68i |
| SEQ ID NO: 100 | | | | Invader | TGTCTTGCAAGTAGTGTCCAGCGTCGTGCACAC | K5g70i |
| | A9 Pool | | | | | |
| SEQ ID NO: 101 | J4 | 33,52,58,67 | E7 | Probe | CGCGCCGAGGGTCCATCTGGCCAGTCCA | J4a1b |
| SEQ ID NO: 102 | | | | Invader | CCCAAATATAATCACAATGCTGATGTAGTAATTGCTTATGGCTTGTTCTGCTTC | J4a6i |
| SEQ ID NO: 103 | | | | Invader | TGTAGTAATTAGCTGTGGCAGGTTGTCTTC | J4a10i |
| SEQ ID NO: 104 | | | | Invader | GCTCCAACGGGTTCCTGCAGTAACAATTGGTAATTGGTTGTATCTGGTTTTGCTTC | J4a13i |
| SEQ ID NO: 105 | N12 | 31,35 | L1 | Probe | CGCGCCGAGGGCACGTTGCAGCCAATATG | N12a1p |
| SEQ ID NO: 106 | | | | Invader | CAGCCAAGCGCAGGCGCCCAACAAATAGCATTATTGTCCCTGAC | N12a3ib |
| SEQ ID NO: 107 | | 35, 1A | | Invader | CAGCCAAGCGCAGGCGCGTTACTCCAACAAATAGCATTATTATGGCCTTGTC | N12a5ib |
| SEQ ID NO: 108 | Z1 | 33,52,58,67 | L1 | Probe | CGCGCCGAGGGCCACGGTGTACCTGCCT | Z1a1pa |

FIGURE 7

| | | | | | |
|---|---|---|---|---|---|
| SEQ ID NO: 109 | AN1 | 16, 31, 35 | E7 | Invader | ATGTCCGTGAGGCGGGCCTAGTGAGC | Z1a3i |
| SEQ ID NO: 110 | | | | Probe | CGCGGCCGAGGGGTTATGCTTGTCCAGCTG | AN1a7p |
| SEQ ID NO: 111 | | | | Invader | CAGCCAAGCGCAGGCGCATTTCCAACAGGACGTTACAATATTATAATTGGAGGTGTCTC | AN1a8i |
| SEQ ID NO: 112 | | | | Invader | CAGCCAAGCGCAGGCGCTGACAACAACAGGTAACGATATTGTAATTGGATGTGTCCC | AN1a9i |
| SEQ ID NO: 113 | | | | Invader | CAGCCAAGCGCAGGCGGGCAACACAAGGTTACAATATTGTAATGGGCTCTGTCCC | AN1a10i |
| SEQ ID NO: 114 | A3a | 16,31 | L1 | Probe | CGCGGCCGAGGACATAATCATCCGTGCTTACAAC | A3a3p |
| SEQ ID NO: 115 | | | | Invader | TGCCTGCATGATAATAGATGTTTGTGCGTGCAT | A3a5i |
| SEQ ID NO: 116 | | | | Invader | GCCTAGAACTGCCTGCGTGATAGTATATGTTTGTTCGTGTTT | A3a6i |
| Internal Control | | | | | | |
| SEQ ID NO: 117 | α-actin | NA | α-actin | Probe | ACGGACGCGGAGAGGAACCCTGTGACAT | 1825-20-03 |
| SEQ ID NO: 118 | | NA | α-actin | Invader | CCATCCAGGGAAGAGTGGCCTGTTT | 1825-20-04 |
| FRET Cassettes | | | | | | |
| SEQ ID NO: 119 | Arm 1 | | | FRET | Fam-TCT-Z28-AGCCGGTTTCCGGCTGAGACCTCGGCGCG-hex | 23-428 |
| SEQ ID NO: 120 | Arm AH9 | | | FRET | Fam-TCT-Z28-AGCCGGTTTCCGGGTGAGAACTCCCAGACTGCC-hex | |
| SEQ ID NO: 121 | Arm 3 | | | FRET | Red-TCT-Z28-TCGGCCTTTTGGCCGGAGAGACTCCGCGTCCGT-hex | 23-394 |

FIGURE 10

| | Assay Name | Strains Detected by Assay | Gene | Oligo Type | Sequence (5'-3') | Oligo Name |
|---|---|---|---|---|---|---|
| | A5/A6 Pool | | | | | |
| SEQ ID NO: 122 | W18 | 51 | L1 | Probe | GGCAGTCTGGGAGTGCTGAGGTTTCCCAACA | W18a1P |
| SEQ ID NO: 123 | | | | Probe | GGCAGTCTGGGAGTGCTGCAGTTTCCCAACA | W18a2P |
| SEQ ID NO: 124 | | | | Invader | GCTCCAACGGGTTTCCTGCACTACCAGACGTACAAATTAACTATTAGCACTGCCACTC | W18a2ci |
| SEQ ID NO: 125 | O13 | 56 | L1 | Probe | GGCAGTCTGGGAGTGGTAGGGAGCAGACCGCTT | O13a5P |
| SEQ ID NO: 126 | | | | Invader | CAGCCAAGCGCAGGCGGCCCTCTTACGTTTTGCTGGTGTAGAGGTGGAC | O13a1ci |
| | A7 Pool | | | | | |
| SEQ ID NO: 127 | R12 | 45, 70 | L1 | Probe | CGCGGCCGAGGATTCCCCTTCCCCCAGTGGC | R12b4b |
| SEQ ID NO: 128 | | | | Invader | TCCGGTGCATTATACACAAGTGTGCACACGGATATACTTGAGGCGTCCTGGTACTCATGTATC | R12b70i |
| SEQ ID NO: 129 | | | | Invader | TCCGGTGCATTATACACAAGTGTGCACTAATATGCTTGAAACCCCTGGCAGTTGTGTGTC | R12b45i |
| SEQ ID NO: 130 | R12 | 45, 70 | L1 | Probe | CGCGCCGAGGATTCCCCTTCCCCCAGTGGCT | R12b4c |
| SEQ ID NO: 131 | R12 | 45, 70 | L1 | Probe | CGCGCCGAGGATTCCCCTTCCCCCAGTGGCTC | R12b4d |
| SEQ ID NO: 132 | F3 | 18, 45 | E6 | Probe | CGCGCCGAGGGCTGGGTTCAACGGTTTCTGG | F3g3b |
| SEQ ID NO: 133 | | | | Invader | GTCCAGCTATGTTGTGGAATCGTCGTTTTCCTTAAGGTGTCTAGGTTTTTCTC | F3g5i |
| SEQ ID NO: 134 | F6 | 18, 39, 45 | E7 | Probe | CGCGCCGAGGTTTGTCAAGGGTGTGCCAGCAGCTGTTTCTGAAGACCCTGTCA | F6d1 |
| SEQ ID NO: 135 | | | | Invader | TGGATGCTGTCAAGGGTGTGCCAGCAGTGTCTGAAGACCCTGTCA | F6d18i |
| SEQ ID NO: 136 | | | | Invader | GGTGGAGGCGACAGATTGTGAGAACTACAGCAGATGTTATGGACTCACTAGGAA | F6d39i |
| SEQ ID NO: 137 | | | | Invader | GGTGGAGGCGACAGATTGTGAGACTACAGACATCTGTTTTGAGCACCTTGTCCA | F6d45i |
| SEQ ID NO: 138 | T3 | 18,59 | E6 | Probe | CGCGCCGAGGGATCCTCAAAGCGAGCCAT | T3e1c |
| SEQ ID NO: 139 | T3 | 18,59 | E6 | Probe | CGCGCCGAGGGGATCCTCAAAGCGAGCC | T3c1 |
| SEQ ID NO: 140 | | | | Invader | ATTCTGTGCACAAATCAGGTAGCTTGTAGGGTCGTCGTGTTC | T3c4i |
| SEQ ID NO: 141 | | | | Invader | TGCACAAATCAGGCAGTTGTAAGGTCGTTGTGTAGC | T3c6i |
| SEQ ID NO: 142 | R4 | 45, 59 | E7 | Probe | CGCGCCGAGGGAGCGGAACCACAGCGTCA | R4d1c |
| SEQ ID NO: 143 | R4 | 45, 59 | E6 | Probe | CGCGCCGAGGCGAGCGGAACCACACAGG | R4b1 |
| SEQ ID NO: 144 | | | | Invader | GGGCCATAAATAATAATTATCCTCATGCACAACTACCGGCCCGAA | R4b4i |
| SEQ ID NO: 145 | | | | Invader | GAGGAAGAAAACGATGAACTAGATGAGTTAATCATTGCTACTAGCTAGAA | R4b5i |
| SEQ ID NO: 146 | F11 | 18, 45 | L1 | Probe | CGCGCCGAGGATTGGACAAAACGATATGTATCCAC | F11a2b |
| SEQ ID NO: 147 | K5 | 39, 68, 70 | E6 | Probe | CGCGCCGAGGGGGTCCGGCAATTTGTATGGCC | K5g2b |
| SEQ ID NO: 148 | | | | Probe | CGCGCCGAGGGCCATACAAATTGCCGGACC | K5b2 |
| SEQ ID NO: 149 | | | | Invader | GAATGGCGCGATTTCACAACCCTGAAGAACGC | K5b3i |
| SEQ ID NO: 150 | K15 | 39,68,70 | E6 | Invader | AGATGGCGACACCAATCCGGAGAAAAATTAAGACACCTAAATAGAAAACGAAGATTTCATAAAATAGCC | K15d9i |
| SEQ ID NO: 151 | | | | Invader | AGATGGCGACACCAATCCGGCTAAGGCACCTAACAACCAAACGAAGATTACATAAAATAGCC | K15d10i |
| SEQ ID NO: 152 | | | | Invader | AGATGGCGACACCAATCCGAACTAAGGCACCTAAATTCCAAACGAAGATTTCATAAAATAGCC | K15d11i |
| SEQ ID NO: 153 | | | | Invader | AGATGGCGACACCAATCCGGAATTAAGGCATGTTAATACAAAAGAAGATTTCACCAAATAGCC | K15d12i |

FIGURE 10

| | | | | | |
|---|---|---|---|---|---|
| SEQ ID NO: 154 | T16 | 18, 59 | E7 | Probe | CGCGCCGAGGGTTGCCTTTGGTCCATGCAT | T16b1b |
| SEQ ID NO: 155 | | | | Invader | CAGCCAAGCGCAGGCGTTCATTTTGTGGCTCTAAATGCAATACAATGTATTGCAATC | T16b18i |
| SEQ ID NO: 156 | | | | Invader | CAGCCAAGCGCAGGCGCTCATAATTTTGTGGTTCCAAATCTAAATCAATGTCACAAAGTC | T16b59i |
| SEQ ID NO: 157 | I2 | 59, 70 | L1 | Probe | CGCGCCGAGGGCCAGGTACACAGCCTATAATACA | I2a2p |
| SEQ ID NO: 158 | | | | Invader | GTCAGCCAAGCGCAGGCGCAGGGCGTAGCCCTTCGCCCAGTGCTCTCCCATAC | I2a3i |
| SEQ ID NO: 159 | | | | Invader | GTCAGCCAAGCGCAGGCGCTACAGTCGCCCTGTGTCCAGTGTCTCCAATGC | I2a4i |
| A9 Pool | | | | | | |
| SEQ ID NO: 160 | C7 | 16, 35 | E6 | Probe | CGCGCCGAGGACGTAGAGAAACCCAGGTGT | 2017-13-01 |
| SEQ ID NO: 161 | | | | Invader | CCAAGCGCAGGCGTAAGGCGGTCGATGTATGTCTTGTTGGAGATCATCAAGAACT | 2017-22-01 |
| SEQ ID NO: 162 | | | | Invader | CCAAGCGCAGGCGTAAGGCAGGTCGGTGTGTCCTGTTGGAAACCAACT | 2017-22-02 |
| SEQ ID NO: 163 | A3 V2 | 16, 31, 58 | L1 | Probe | CGCGCCGAGGACATATTCATCTGTGCTTACAAC | 1982-74-02 |
| SEQ ID NO: 164 | | | | Invader | TGCCTGCTGATAATAGATGTTTGTGCGTGCAT | A3a5i |
| SEQ ID NO: 165 | | | | Invader | GCCTAGAATGCCCTGCGTGATAGTATATGTTTTGTTCGTGTTT | A3a6i |
| SEQ ID NO: 166 | | | | Invader | GTCTGGAACTGCCAGCGTAATAGTAAATGCTTGTGCGTGACT | 1982-74-03 |
| SEQ ID NO: 167 | PIIb | 33, 52, 58 | | Probe | CGCGCCGAGGATGAGCAATTACGTGACAGCTC | 1662-38-12P |
| SEQ ID NO: 168 | | | | Invader | TACTAGATATGAAACCCGAAACAACTGACCTACACTGCTC | P11b7i |
| SEQ ID NO: 169 | | | | Invader | TGTTTAGATTTATATCCTGAACCAAGTGACCTATTCTGCTC | P11b8i |
| SEQ ID NO: 170 | Z2 | 33, 52, 67 | L1 | Probe | CGCGCCGAGGGTTTACGACTGCGACG | 12576-Ss1P1 |
| SEQ ID NO: 171 | | | | Invader | GCCGCCACACGGACATCTGGAAAAAATATGGAAAACT | 1935-60-02 |
| SEQ ID NO: 172 | | | | Invader | CCGGCCACACGGACACTCTGTAAAAAATATGGAAACCT | 6063Z1 |
| SEQ ID NO: 173 | J4 v2 | 33, 52, 58, 67 | E7 | Probe | CGCGCCGAGGGCTTGTCCATCTGGCCAGTC | 2030-74-09 |
| SEQ ID NO: 174 | | | | Invader | GCTCCAACGGGTTCCTGCTGTCACAATGTAGTAATTGCTTGTAGCTTGTTCTT | 2030-74-11 |
| SEQ ID NO: 175 | | | | Invader | ACAACAGGTTACAATGTAGTAATTAGCTGTGTGGCAGGTTGTT | 2030-74-12 |
| SEQ ID NO: 176 | | | | Invader | GCTCCAACGGGTTCCTGCCACACAGTAACAATTTGGTAATTGGTTGTATCTGGTTTT | 2030-74-13 |
| SEQ ID NO: 177 | N12 v2 | 31, 35 | L1 | Probe | CGCGCCGAGGGCACGTTGCAGCCAATATGG | 2030-79-01 |
| SEQ ID NO: 178 | | | | Invader | CAGCCAAGCGCAGGCGCCCAACAAATAGCATTATTGTCCCTGAC | N12a3ib |
| SEQ ID NO: 179 | | | | Invader | CAGCCCAAGCGCAGGCGGTTACTCCAACAAATAGCATTATTATGGCCTTGTC | N12a5ib |

FIGURE 10

| | | | | | |
|---|---|---|---|---|---|
| SEQ ID NO: 180 | Z1 v2 | 33, 52, 58, 67 | L1 | Probe | CGCGCCGAGGGCCACGGTGTACCTGCCTC | 2030-81-01 |
| SEQ ID NO: 181 | | | | Invader | ATGTCCGTGAGGCGGCCTAGTGAGC | Z1a3i |
| SEQ ID NO: 182 | PIIb v2 | 33, 35 | E7 | Probe | CGCGCCGAGGATGAGCAATTGAGTGACAGCT | 1982-70-01 |
| SEQ ID NO: 183 | | | | Invader | GGTCGTGCTCCAACGGGTTTCCTTTAGATTTGGAACTGAGGCAACTGACCTATACTGTTC | 1982-70-04 |
| SEQ ID NO: 184 | | | | Invader | GGTCGTGCTCCAACGGGTTTCCTTTAGATTTGCAACCTCAGGCAACTGACCTATACTGCTC | 1982-70-05 |
| SEQ ID NO: 185 | C9 | 16, 35 | L1 | Probe | CGCGCCGAGGCCAGCCCTATTAAATAAATGTCAAAC | 2030-19-26 |
| SEQ ID NO: 186 | | | | Invader | CAGCCAAGCGCAGCGGCCTTTAATGTATAAATCGTTTGGTACATTTTCACCAACAGTAT | 2030-19-29 |
| SEQ ID NO: 187 | | | | Invader | CAGCCAAGCGCAGGCGCCCTTAATATATAGGTCTGTAGGTACTGTTTCACCTACAGTTT | 2030-19-30 |
| SEQ ID NO: 188 | A1g v2 | 16, 31 | E7 | Probe | CGCGCCGAGGGTCCGGTTATGCTTGTCC | A1g3px |
| SEQ ID NO: 189 | | | | Invader | CAGCCAAGCGCAGGCGCTTGCAACACAAGGTTACAATATTGTAATGGGCTCTC | A1g3i-1 |
| SEQ ID NO: 190 | | | | Invader | CAGCCAAGCGCAGGCGCTGACGAGCAACAAAAGGAAAACGATATTGTAATTGGATGTC | A1g3i-3 |
| SEQ ID NO: 191 | A1g v3 | 16, 31 | E7 | Probe | CAGCCGCGAGGGTCCGGTTGTGCTTGTCC | A1g3py |
| SEQ ID NO: 192 | | | | Invader | CAGCCAAGCGCAGGCGCTTGCAACACAAGGTTACAATATTGTAATGGGCTCTC | A1g3i-1 |
| SEQ ID NO: 193 | | | | Invader | CAGCCAAGCGCAGGCGACTGACAACAAAAGGAAAACGATATTGTAATTGGATGTC | A1g3i-3 |

DETECTION OF HPV

The present Application claims priority to U.S. Provisional Application Ser. No. 60/505,786, filed Sep. 25, 2003, herein incorporated by reference in its entirety.

FIELD OF THE INVENTION

The present invention provides methods and composition related to nucleic acid detection assays for use in basic research, clinical research, and for the development of clinical detection assays. In particular, the present invention provides methods for characterizing human papillomavirus (HPV) sequences.

BACKGROUND

Cervical cancer accounts for nearly 10% of all female cancers and is a leading cause of cancer among women in developing countries (Franco, E. L. et al., Can Med Assoc J. 2001;164:1017-25). The regions with the highest incidence of the disease are generally those with the greatest mortality and include Central America, Africa, and the Caribbean (Ferlay, J. et al., 1998. IARC Cancer Base no. 3. Lyon:IARC-Press). Incidence in Europe and North America has declined precipitously over the past 50 years, possibly due to the advent of routine screening by Papanicolaou (Pap) smear testing (reviewed in Franco et al., ibid). Cervical cancer is one of the most preventable cancers, with survival being directly related to the stage of the disease at diagnosis. The 5-year survival rate is 88% for women having initial diagnosis of localized disease as opposed to 13% for women diagnosed with distant disease (Report of the Gynecologic Cancers Progress Review Group, November 2001, National Cancer Institute). More than 50% of women diagnosed with cervical cancer in the U.S. have not had a Pap smear in the past three years (Wright, T. C. et al., JAMA. 2000; 283:81-6).

Pap screening remains the predominant mode of detecting cancerous and precancerous cervical lesions; more than 50 million women undergo Pap screening each year in the U.S. (Wright, T. C. et al., JAMA 2002; 287:2120-29). Despite its widespread use, Pap smear testing is only partially effective; some estimates place the sensitivity of conventional Pap smear testing at 50-60% (Lorincz, A. T. and Richart, R. M., (Arch Pathol Lab Med. 2003;127:959-68; Nanda, K. et al., 2000. Ann Intern Med 132:810; Fahey M T, et al. Am J. Epidemiol. 1995;141:680-9; Myers E R, McCrory D C, Subramanian S, et al. Obstet Gynecol. 2000;96:645-52) or 70-80% (Clavel, C. et al., 2001. Br J Cancer 84:1616). Recent innovations in cytological screening and sampling, such as liquid-based tests, have improved the sensitivity of these methods to 75-95% (Lorincz, A. T. et al. ibid; Nanda, K. et al., ibid.; Hutchinson M L, Zahniser D J, Sherman M E, et al. Cancer. 1999;87:48-55). Nonetheless, even these improved methods fail to detect a significant portion of abnormal, and often precancerous, cells. Once identified, patients with atypical squamous cells of undetermined significance (AS-CUS) are subjected to various levels of monitoring and treatment, depending on the particular attendant risk factors and clinical presentation (reviewed in Wright, T. C. et al. JAMA 2002, ibid).

Human Papillomavirus (HPV) has been identified as the primary, and possibly only, cause of cervical cancer (Muñoz N, Bosch FX, de Sanjosé S, et al., Int J Cancer 1992;52:743-9; Bosch F X, Lorincz A, Munoz N, Meijer Shah K V., Clin Pathol 2002;55:244-65), implicated in as many as 99.7% of all cases (Wallboomers, J. M. et al., 1999. J Pathol 189:12-19). The HPV genome is an 8 kb, circular, double stranded DNA comprising 8 genes, all encoded on the same strand. As many as 200 different HPV types have been identified in humans (Burd, E. M. Clin Microbiol Rev. 2003;16:1-17); of these approximately 40 types have been found capable of infecting the genital tract (Munoz, N. N Engl J Med 2003; 348:518-27). Still further classification has resulted in the identification of high- and low-risk viral types for development of cervical cancer. Estimates place the number of high-risk types between 13-19 strains, with two strains, HPV 16 and 18 together accounting for as much as 55-85% of infections, depending on subject age and geographical location (Munoz, N., ibid). The predominant low-risk strains are HPV 6 and 11; these may lead to genital warts (reviewed in Burd, E. M., ibid).

The elucidation of certain high risk HPV strains as the causative agents of cervical cancer, coupled with advances in molecular biological methods, has expanded the spectrum of methods available for both preventing and detecting HPV infection. Vaccines for the most common high-risk HPV strains are currently in clinical trials (Koutsky, L A. et al., 2002. NEJM 347:1645-51). Moreover, some authorities are calling for HPV DNA screening for use in conjunction with, or in some cases, in lieu of, conventional cytological methods (Wright, T. C. and Schiffman, M. N. Engl. J. Med, 2003; 348: 489-90). Various alternative DNA-based detection methods have been introduced, including the HYBRID CAPTURE II (HCII) test (Digene, Gaithersburg, Md.), which was been approved by the FDA in March, 1999. The HYBRID CAPTURE method relies on hybridization of target DNA to complementary RNA probes. The resultant RNA-DNA hybrids are recognized by surface-bound antibodies as well as antibodies conjugated to alkaline phosphatase, allowing generation of a chemiluminescent signal in the presence of appropriate substrates (Lorincz, A. T. J Obstet Gynaecol Res. 1996;22:629-36; also U.S. Pat. No. 4,908,306 and related patents and applications). Further alternative methods include the use of sequence specific probes for use in PCR or sandwich hybridization assays, such as those described in U.S. Pat. No. 6,583,278. Other methods rely on various PCR primers for selective amplification of specific strains, as in U.S. Pat. No. 5,447,839 and related applications. Still other methods rely on in situ hybridization of sequence-specific probes to isolated cervical cells, described in WO 00/24760A1 (e.g. INFORM HPV, Ventana Medical Systems, Inc., Tuscon, Ariz.; Qureshi MN et al., Diagn. Cytopathol. 2003;29:149-155).

Therefore, there exists a need for a rapid, sensitive, and highly quantitative direct detection assay for detecting HPV infection by high risk strains in cervical samples. Given the current reliance on molecular methods, it is likely that there will be an ongoing and increasing need for rapid, quantitative methods of detecting HPV infection.

SUMMARY OF THE INVENTION

The present invention provides compositions and methods for the detection and characterization of sequences associated with human papillomavirus (HPV). More particularly, the present invention provides compositions, methods and kits for using invasive cleavage structure assays (e.g. the INVADER assay, Third Wave Technologies, Madison, Wis.) to screen nucleic acid samples, e.g., from patients, for the presence of any one or more of a collection of sequences associated with HPV. The present invention also provides compositions, methods and kits for screening sets of different HPV sequences in a single reaction container. The present invention may be used to detect integrated and/or non-integrated viral sequences.

In other embodiments, synthetic DNA suitable for use with the methods and compositions of the present invention is made using a purified polymerase on multiply-primed genomic DNA, as provided, e.g., in U.S. Pat. Nos. 6,291,187, and 6,323,009, and in PCT applications WO 01/88190 and WO 02/00934, each herein incorporated by reference in their entireties for all purposes. In these embodiments, amplification of DNA such as genomic DNA is accomplished using a DNA polymerase, such as the highly processive Φ 29 polymerase (as described, e.g., in U.S. Pat. Nos. 5,198,543 and 5,001,050, each herein incorporated by reference in their entireties for all purposes) in combination with exonuclease-resistant random primers, such as hexamers.

The method is not limited by the nature of the target nucleic acid. In some embodiments, the target nucleic acid is single stranded or double stranded DNA or RNA. In some embodiments, double stranded nucleic acid is rendered single stranded (e.g., by heat) prior to formation of the cleavage structure. In some embodiments, the source of target nucleic acid comprises a sample containing genomic DNA. Sample include, but are not limited to, tissue sections, blood, saliva, cerebral spinal fluid, pleural fluid, milk, lymph, sputum and semen.

In some embodiments, the present invention provides methods of detecting an HPV sequence or method for diagnosing cancer, comprising; a) providing; i) a sample from a subject; and ii) a composition comprising an oligonucleotide detection assay (e.g. as described herein); and b) contacting said sample with said composition such that the presence or absence of at least one HPV sequence is determined. In some embodiments, the sample is a tissue section, blood sample, mouth swab sample, saliva sample, or other biological fluid sample from the subject.

In some embodiments, the present invention provides a method for detecting at least one HPV sequence in a sample, comprising using a first and a second oligonucleotide, wherein the oligonucleotides are configured to form an invasive cleavage structure with a target sequence comprising the at least one HPV sequence. In some embodiments, the first oligonucleotide comprises a 5' portion and a 3' portion, wherein the 3' portion is configured to hybridize to the target sequence, and the 5' portion is configured to not hybridize to the target sequence. In some embodiments, the second oligonucleotide comprises a 5' portion and a 3' portion, wherein the 5' portion is configured to hybridize to the target sequence, and wherein the 3' portion is configured to not hybridize to the target sequence. In preferred embodiments, the first and second oligonucleotides are selected from the group consisting of SEQ ID NOS. 1-5, 7-62, 64-67, 69-70, 73-116 and 122-193.

In some embodiments, the present invention provides a method for detecting the presence or absence of HPV nucleic acid in a sample comprising providing a sample comprising nucleic acids and an invasive cleavage assay configured to detect at least one HPV nucleic acid and exposing the sample to the detection assay under conditions such that the at least one HPV nucleic acid can be detected, and detecting the presence or absence of HPV nucleic acid in a sample. In some embodiments, the detecting comprises identifying one or more strains of HPV present in the sample. In preferred embodiments, the HPV strain is selected from the group consisting of, but not limited to, HPV 16, 16Ty2, 18, 31, 33, 35, 39, 45, 51, 52, 56, 58, 58iso, 59, 66, 67, 68, 68var, 69, 70, or 82. In some embodiments, the nucleic acid is amplified prior to said exposure step.

In some embodiments, the present invention provides a method for detecting the presence or absence of HPV nucleic acid in a sample comprising treating the sample using a first oligonucleotide and a second oligonucleotide, wherein the oligonucleotides are configured to form an invasive cleavage reaction and detecting the presence or absence of HPV nucleic acid. In particular embodiments, the oligonucleotides comprise one or more oligonucleotides selected from the group consisting of, but not limited to, SEQ ID NOS. 1-5, 7-62, 64-67, 69-70, 73-116 and 122-193. In some preferred embodiments, the oligonucleotides individually contain one or more mismatches with target HPV nucleic acid. In some embodiments, the oligonucleotides are configured to hybridize to non-HPV nucleic acid sequences or two hybridize to two or more strains of HPV. In some embodiments, the oligonucleotides are configured such that a stable hybridization duplex between one or more of the oligonucleotides and the HPV target nucleic acid is not formed.

In some embodiments, the target nucleic acid comprises genomic DNA or mRNA. In other embodiments, the target nucleic acid comprises synthetic DNA or RNA. In some preferred embodiments, synthetic DNA or RNA within a sample is created using a purified polymerase. In some preferred embodiments, creation of synthetic DNA using a purified polymerase comprises the use of PCR. In some preferred embodiments, creation of synthetic DNA comprises use of the methods and compositions for amplification using RNA-DNA composite primers (e.g., as disclosed in U.S. Pat. No. 6,251,639, herein incorporated by reference in its entirety). In other preferred embodiments, creation of synthetic DNA using a purified DNA polymerase suitable for use with the methods of the present invention comprises use of rolling circle amplification, (e.g., as in U.S. Pat. Nos. 6,210,884, 6,183,960 and 6,235,502, herein incorporated by reference in their entireties). In other preferred embodiments, creation of synthetic DNA comprises amplification using nucleic acids comprising loop-forming sequences, e.g., as described in U.S. Pat. No. 6,410,278, herein incorporated by reference in its entirety.

In some embodiments, the present invention provides methods and kits configured to detect more than one HPV strain in a single reaction vessel (e.g., kits and methods to detect all high risk strains in four or fewer reactions). Thus, the present invention provides kits and methods comprising pooled detection assay components. In some preferred embodiments, a single oligonucleotide in the pooled detection assay components is configured to take part in an invasive cleavage structure in the presence of two or more HPV target strains. The pooled detection assay components also find use in methods and kits using detection technologies other than invasive cleavage technology. For example, the pooled detection assays for detection of HPV sequences (e.g., wherein one or more oligonucleotides find use in detecting multiple HPV sequences in a single reaction) provided in the present invention may find use in detection assays that include, but are not limited to, enzyme mismatch cleavage methods (e.g., Variagenics, U.S. Pat. Nos. 6,110,684, 5,958,692, 5,851,770, herein incorporated by reference in their entireties); polymerase chain reaction; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (Barnay Proc. Natl. Acad. Sci USA 88, 189-93 (1991)); and sandwich hybridization methods (e.g., U.S. Pat. No. 5,288,609, herein incorporated by reference in its entirety).

In some embodiments, the present invention provides kits or compositions comprising a non-amplified oligonucleotide detection assay configured for detecting at least one HPV sequence. In other embodiments, the non-amplified oligonucleotide detection assay comprises first and second oligonucleotides configured to form an invasive cleavage structure (e.g. an INVADER assay) in combination with a target sequence comprising said at least one HPV sequence. In particular embodiments, the first oligonucleotide comprises a 5' portion and a 3' portion, wherein the 3' portion is configured to hybridize to the target sequence, and wherein the 5' portion is configured to not hybridize to the target sequence. In other embodiments, the second oligonucleotide comprises a 5' portion and a 3' portion, wherein the 5' portion is configured to hybridize to the target sequence, and wherein the 3' portion is configured to not hybridize to the target sequence.

In some embodiments, the present invention provides a kit comprising oligonucleotide detection assays configured for detecting a HPV sequence, wherein the kit comprises one or more oligonucleotides selected from the group consisting of SEQ ID NOS. 1-193. In particular embodiments, the multiple HPV strains are detected simultaneously by combining one or more of the oligonucleotides into one or more reactions. In preferred embodiments, none of the oligonucleotides are completely complementary to HPV target nucleic acid sequences. In some embodiments, the oligonucleotides comprise sequences not completely complementary to any target sequence that is detected. In preferred embodiments, all high-risk HPV strains are detected in four or fewer reactions. In other preferred embodiments, all high-risk HPV strains can be detected in three or fewer reactions.

In some embodiments, the present invention provides a kit comprising oligonucleotide detection assays configured for detecting all high-risk HPV strains. In preferred embodiments, the oligonucleotides are not fully complementary to nucleic acid sequences of the HPV strains. In further preferred embodiments, the oligonucleotides hybridize to multiples regions of a single HPV nucleic acid (e.g., to provide redundancy in detection). In even further preferred embodiments, the oligonucleotides are selected from the group consisting of SEQ ID NOS. 77-116 and 122-193.

In some embodiments, the detected HPV sequences are any of those found below in Table 1 or variants thereof. It is understood that sequences will diverge over time and that other HPV varieties, now know, or later discovered are readily adaptable to the methods and invention, per the description herein.

TABLE 1

| strain | accession |
| --- | --- |
| 1a | NC_001356 |
| 1a | U06714 |
| 2a | X55964 |
| 3 | NC_001588 |
| 3 | X74462 |
| 4 | NC_001457 |
| 4 | X70827 |
| 5 | M17463 |
| 5 | NC_001531 |
| 5b | D90252 |
| 5b | NC_001444 |
| 6a | L41216 |
| 6a | NC_001668 |
| 6b | NC_001355 |
| 6 | AF092932 |
| 6 | NC_000904 |
| 7 | M12588 |
| 7 | NC_001595 |
| 7 | X74463 |
| 8 | M12737 |
| 8 | NC_001532 |
| 9 | NC_001596 |
| 9 | X74464 |
| 10 | NC_001576 |
| 10 | X74465 |
| 11 | J04351 |
| 11 | M14119 |
| 11 | NC_001525 |
| 12 | NC_001577 |
| 12 | X74466 |
| 13 | NC_001349 |
| 13 | X62843 |
| 14d | NC_001578 |
| 14d | X74467 |
| 15 | NC_001579 |
| 15 | X74468 |
| 16 | AF125673 |
| 16 | AF472508 |
| 16 | AF472509 |
| 16 | K02718 |
| 16 | NC_001526 |
| 16 | U89348 |
| 17 | NC_001580 |
| 17 | X74469 |
| 18 | NC_001357 |
| 18 | X05015 |
| 18 | X05349 |
| 19 | NC_001581 |
| 19 | X74470 |
| 20 | NC_001679 |
| 20 | U31778 |
| 21 | NC_001680 |
| 21 | U31779 |
| 22 | NC_001681 |
| 22 | U31780 |
| 23 | NC_001682 |
| 23 | U31781 |
| 24 | NC_001683 |
| 24 | U31782 |
| 25 | NC_001582 |
| 25 | X74471 |
| 26 | NC_001583 |
| 26 | X74472 |
| 27 | NC_001584 |
| 27 | X74473 |
| 28 | NC_001684 |
| 28 | U31783 |
| 29 | NC_001685 |
| 29 | U31784 |
| 30 | NC_001585 |
| 30 | X74474 |
| 31 | J04353 |
| 31 | NC_001527 |
| 32 | NC_001586 |
| 32 | X74475 |
| 33 | M12732 |
| 33 | NC_001528 |

TABLE 1-continued

| strain | accession |
|---|---|
| 34 | NC_001587 |
| 34 | X74476 |
| 35 | M74117 |
| 35 | NC_001529 |
| 35h | X74477 |
| 36 | NC_001686 |
| 36 | U31785 |
| 37 | NC_001687 |
| 37 | U31786 |
| 38 | NC_001688 |
| 38 | U31787 |
| 39 | M62849 |
| 39 | AF548856 |
| 39 | AF548857 |
| 39 | NC_001535 |
| 40 | NC_001589 |
| 40 | X74478 |
| 41 | NC_001354 |
| 41 | X56147 |
| 42 | NC_001534 |
| 42 | M73236 |
| 43 | U12504 |
| 43 | Y12214 |
| 44 | NC_001689 |
| 44 | U31788 |
| 45 | NC_001590 |
| 45 | X74479 |
| 47 | M32305 |
| 47 | NC_001530 |
| 48 | NC_001690 |
| 48 | U31789 |
| 49 | NC_001591 |
| 49 | X74480 |
| 50 | NC_001691 |
| 50 | U31790 |
| 51 | M62877 |
| 51 | NC_001533 |
| 52 | NC_001592 |
| 52 | X74481 |
| 53 | NC_001593 |
| 53 | X74482 |
| 54 | AF436129 |
| 54 | NC_001676 |
| 54 | U37488 |
| 55 | NC_001692 |
| 55 | U31791 |
| 56 | NC_001594 |
| 56 | X74483 |
| 57 | NC_001353 |
| 57 | X55965 |
| 57b | U37537 |
| 58 | D90400 |
| 58 | NC_001443 |
| 59 | NC_001635 |
| 59 | X77858 |
| 60 | NC_001693 |
| 60 | U31792 |
| 61 | NC_001694 |
| 61 | U31793 |
| 62 | U12499 |
| 63 | NC_001458 |
| 63 | X70828 |
| 64 | U12495 |
| 65 | NC_001459 |
| 65 | X70829 |
| 66 | NC_001695 |
| 66 | U31794 |
| 67 | D21208 |
| 68 | M73258 |
| 68 | Y14591 |
| 69 | AB027020 |
| 69 | NC_002171 |
| 70 | NC_001711 |
| 70 | U21941 |
| 71 | AB040456 |
| 71 | NC_002644 |
| 72 | X94164 |
| 73 | X94165 |
| 74 | AF436130 |
| 74 | NC_004501 |
| 75 | Y15173 |
| 76 | Y15174 |
| 77 | Y15175 |
| 80 | Y15176 |
| 82 | AB027021 |
| 82 | AF293961 |
| 82 | NC_002172 |
| 83 | AF151983 |
| 83 | NC_000856 |
| 84 | AF293960 |
| 84 | NC_002676 |
| 85 | AF131950 |
| 86 | AF349909 |
| 86 | NC_003115 |
| 87 | AJ400628 |
| 87 | NC_002627 |
| 89 | NC_004103 |
| 90 | AY057438 |
| 90 | NC_004104 |
| 91 | AF419318 |
| 91 | AF436128 |
| 91 | NC_004085 |
| 92 | AF531420 |
| 92 | NC_004500 |
| RXRX7 | U85660 |

In certain embodiments, the oligonucleotide detection assays are selected from sequencing assays, polymerase chain reaction assays, hybridization assays, hybridization assays employing a probe complementary to a mutation, microarray assays, bead array assays, primer extension assays, enzyme mismatch cleavage assays, branched hybridization assays, rolling circle replication assays, NASBA assays, molecular beacon assays, cycling probe assays, ligase chain reaction assays, invasive cleavage structure assays, ARMS assays, and sandwich hybridization assays.

The present invention also provides methods of detecting target nucleic acids through the use of probe sequences that are not completely complementary to the target nucleic acid. For example, the present invention provides kits and methods for detecting a target sequence by using mismatch probe sequences, comprising the steps of: a) providing a sample suspected of containing a target nucleic acid; b) exposing the sample to one or more oligonucleotides that contain a region that is complementary to said target nucleic acid, said region having a first portion completely complementary to said target nucleic acid, a second portion contiguous to said first portion that is not complementary to said target nucleic acid (e.g., a mismatch), and a third portion contiguous to said second portion that is completely complementary to the target nucleic acid; and c) detecting the target nucleic acid under conditions such that no sequences that are completely complementary to the one or more oligonucleotides or said region of the one or more oligonucleotides are detected (i.e., only sequences that are not completely complementary to the oligonucleotides or the region of the oligonucleotides are detected). Thus, even if the sample contains perfect complements to the oligonucleotides or to the region, such perfect complements are not detected. This can be carried out, for example, through use of two or more oligonucleotides that, through their coordinated action, provide specificity for the non-matched target sequence, but do not detect the perfect complement. The INVADER assay, methods employing ligation, the polymerase chain reaction, etc. are examples of methods that permit such detection. This can also be carried out with a single probe sequence in a hybridization method if the probe is of sufficient length to ensure that it is not completely complementary to any sequence in the sample that might be detected.

In some embodiments, the region of the one or more oligonucleotides contains two or more mismatches to the target nucleic acid (e.g., 3, 4, 5, 6, . . . ). In some embodiments, the region contains no more than twenty (e.g., no more than 15, 12, 10, 9, 8, 7, 6, . . . ) contiguous nucleotides that are completely complementary to the target nucleic acid. In some embodiments, one or more of the oligonucleotides are generated by extending a primer in an enzymatic extension reaction using the target nucleic acid as a template (e.g., in a polymerase chain reaction). In some embodiments, the target nucleic acid is a viral target nucleic acid (e.g., HPV). In some embodiments, the target nucleic acid is a conserved region of a viral genome (i.e., a region that is highly conserved between different strains or family members of the virus). For example, the LCR, E6, and E7 regions of the HPV genome contain conserved sequences.

Definitions

To facilitate an understanding of the present invention, a number of terms and phrases are defined below:

As used herein, the terms "subject" and "patient" refer to any organisms including plants, microorganisms and animals (e.g., mammals such as dogs, cats, livestock, and humans).

As used herein, the term "INVADER assay reagents" refers to one or more reagents for detecting target sequences, said reagents comprising oligonucleotides capable of forming an invasive cleavage structure in the presence of the target sequence. In some embodiments, the INVADER assay reagents further comprise an agent for detecting the presence of an invasive cleavage structure (e.g., a cleavage agent). In some embodiments, the oligonucleotides comprise first and second oligonucleotides, said first oligonucleotide comprising a 5' portion complementary to a first region of the target nucleic acid and said second oligonucleotide comprising a 3' portion and a 5' portion, said 5' portion complementary to a second region of the target nucleic acid downstream of and contiguous to the first portion. In some embodiments, the 3' portion of the second oligonucleotide comprises a 3' terminal nucleotide not complementary to the target nucleic acid. In preferred embodiments, the 3' portion of the second oligonucleotide consists of a single nucleotide not complementary to the target nucleic acid.

In some embodiments, INVADER assay reagents are configured to detect a target nucleic acid sequence comprising first and second non-contiguous single-stranded regions separated by an intervening region comprising a double-stranded region. In preferred embodiments, the INVADER assay reagents comprise a bridging oligonucleotide capable of binding to said first and second non-contiguous single-stranded regions of a target nucleic acid sequence. In particularly preferred embodiments, either or both of said first or said second oligonucleotides of said INVADER assay reagents are bridging oligonucleotides.

In some embodiments, the INVADER assay reagents further comprise a solid support. For example, in some embodiments, the one or more oligonucleotides of the assay reagents (e.g., first and/or second oligonucleotide, whether bridging or non-bridging) is attached to said solid support. In some embodiments, the INVADER assay reagents further comprise a buffer solution. In some preferred embodiments, the buffer solution comprises a source of divalent cations (e.g., $Mn^{2+}$ and/or $Mg^{2+}$ ions). Individual ingredients (e.g., oligo-nucleotides, enzymes, buffers, target nucleic acids) that collectively make up INVADER assay reagents are termed "INVADER assay reagent components."

In some embodiments, the INVADER assay reagents further comprise a third oligonucleotide complementary to a third portion of the target nucleic acid upstream of the first portion of the first target nucleic acid. In yet other embodiments, the INVADER assay reagents further comprise a target nucleic acid. In some embodiments, the INVADER assay reagents further comprise a second target nucleic acid. In yet other embodiments, the INVADER assay reagents further comprise a third oligonucleotide comprising a 5' portion complementary to a first region of the second target nucleic acid. In some specific embodiments, the 3' portion of the third oligonucleotide is covalently linked to the second target nucleic acid. In other specific embodiments, the second target nucleic acid further comprises a 5' portion, wherein the 5' portion of the second target nucleic acid is the third oligonucleotide. In still other embodiments, the INVADER assay reagents further comprise an ARRESTOR molecule (e.g., ARRESTOR oligonucleotide).

In some preferred embodiments, the INVADER assay reagents further comprise reagents for detecting a nucleic acid cleavage product. In some embodiments, one or more oligonucleotides in the INVADER assay reagents comprise a label. In some preferred embodiments, said first oligonucleotide comprises a label. In other preferred embodiments, said third oligonucleotide comprises a label. In particularly preferred embodiments, the reagents comprise a first and/or a third oligonucleotide labeled with moieties that produce a fluorescence resonance energy transfer (FRET) effect.

In some embodiments one or more the INVADER assay reagents may be provided in a predispensed format (i.e., premeasured for use in a step of the procedure without re-measurement or re-dispensing). In some embodiments, selected INVADER assay reagent components are mixed and predispensed together. In preferred embodiments, predispensed assay reagent components are predispensed and are provided in a reaction vessel (including but not limited to a reaction tube or a well, as in, e.g., a microtiter plate). In particularly preferred embodiments, predispensed INVADER assay reagent components are dried down (e.g., desiccated or lyophilized) in a reaction vessel.

In some embodiments, the INVADER assay reagents are provided as a kit. As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

In some embodiments, the present invention provides INVADER assay reagent kits comprising one or more of the components necessary for practicing the present invention. For example, the present invention provides kits for storing or delivering the enzymes and/or the reaction components necessary to practice an INVADER assay. The kit may include any and all components necessary or desired for assays including, but not limited to, the reagents themselves, buffers, control reagents (e.g., tissue samples, positive and negative control target oligonucleotides, etc.), solid supports, labels, written and/or pictorial instructions and product information, software (e.g., for collecting and analyzing data), inhibitors, labeling and/or detection reagents, package environmental controls (e.g., ice, desiccants, etc.), and the like. In some embodiments, the kits provide a sub-set of the required components, wherein it is expected that the user will supply the remaining components. In some embodiments, the kits comprise two or more separate containers wherein each container houses a subset of the components to be delivered. For example, a first container (e.g., box) may contain an enzyme (e.g., structure specific cleavage enzyme in a suitable storage buffer and container), while a second box may contain oligonucleotides (e.g., INVADER oligonucleotides, probe oligonucleotides, control target oligonucleotides, etc.).

The term "label" as used herein refers to any atom or molecule that can be used to provide a detectable (preferably quantifiable) effect, and that can be attached to a nucleic acid or protein. Labels include but are not limited to dyes; radiolabels such as $^{32}P$; binding moieties such as biotin; haptens such as digoxgenin; luminogenic, phosphorescent or fluorogenic moieties; mass tags; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, characteristics of mass or behavior affected by mass (e.g., MALDI time-of-flight mass spectrometry), and the like. A label may be a charged moiety (positive or negative charge) or alternatively, may be charge neutral. Labels can include or consist of nucleic acid or protein sequence, so long as the sequence comprising the label is detectable.

As used herein, the term "distinct" in reference to signals refers to signals that can be differentiated one from another, e.g., by spectral properties such as fluorescence emission wavelength, color, absorbance, mass, size, fluorescence polarization properties, charge, etc., or by capability of interaction with another moiety, such as with a chemical reagent, an enzyme, an antibody, etc.

As used herein, the terms "complementary" or "complementarity" are used in reference to polynucleotides (i.e., a sequence of nucleotides such as an oligonucleotide or a target nucleic acid) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

The term "homology" and "homologous" refers to a degree of identity. There may be partial homology or complete homology. A partially homologous sequence is one that is less than 100% identical to another sequence.

As used herein, the term "hybridization" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the $T_m$ of the formed hybrid. "Hybridization" methods involve the annealing of one nucleic acid to another, complementary nucleic acid, i.e., a nucleic acid having a complementary nucleotide sequence. The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

As used herein, the term "$T_m$" is used in reference to the "melting temperature." The melting temperature is the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation: $T_m=81.5+0.41(\% G+C)$, when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr. Thermodynamics and NMR of internal G.T mismatches in DNA. Biochemistry 36, 10581-94 (1997) include more sophisticated computations which take structural and environmental, as well as sequence characteristics into account for the calculation of $T_m$.

The term "gene" refers to a DNA sequence that comprises control and coding sequences necessary for the production of an RNA having a non-coding function (e.g., a ribosomal or transfer RNA), a polypeptide or a precursor. The RNA or polypeptide can be encoded by a full length coding sequence or by any portion of the coding sequence so long as the desired activity or function is retained.

The term "wild-type" refers to a gene or a gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified", "mutant" or "polymorphic" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "recombinant DNA vector" as used herein refers to DNA sequences containing a desired heterologous sequence. For example, although the term is not limited to the use of expressed sequences or sequences that encode an expression product, in some embodiments, the heterologous sequence is a coding sequence and appropriate DNA sequences necessary for either the replication of the coding sequence in a host organism, or the expression of the operably linked coding sequence in a particular host organism. DNA sequences necessary for expression in prokaryotes include a promoter, optionally an operator sequence, a ribosome binding site and possibly other sequences. Eukaryotic cells are known to utilize promoters, polyadenylation signals and enhancers.

The term "oligonucleotide" as used herein is defined as a molecule comprising two or more deoxyribonucleotides or ribonucleotides, preferably at least 5 nucleotides, more preferably at least about 10-15 nucleotides and more preferably at least about 15 to 30 nucleotides. The exact size will depend on many factors, which in turn depend on the ultimate function or use of the oligonucleotide. The oligonucleotide may be generated in any manner, including chemical synthesis, DNA replication, reverse transcription, PCR, or a combination thereof. In some embodiments, oligonucleotides that form invasive cleavage structures are generated in a reaction (e.g., by extension of a primer in an enzymatic extension reaction).

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. Similarly, when two overlapping oligonucleotides are hybridized to the same linear complementary nucleic acid sequence, with the first oligonucleotide positioned such that its 5' end is upstream of the 5' end of the second oligonucleotide, and the 3' end of the first oligonucleotide is upstream of the 3' end of the second oligonucleotide, the first oligonucleotide may be called the "upstream" oligonucleotide and the second oligonucleotide may be called the "downstream" oligonucleotide.

The term "primer" refers to an oligonucleotide that is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The term "cleavage structure" as used herein, refers to a structure that is formed by the interaction of at least one probe oligonucleotide and a target nucleic acid, forming a structure comprising a duplex, the resulting structure being cleavable by a cleavage means, including but not limited to an enzyme. The cleavage structure is a substrate for specific cleavage by the cleavage means in contrast to a nucleic acid molecule that is a substrate for non-specific cleavage by agents such as phosphodiesterases which cleave nucleic acid molecules without regard to secondary structure (i.e., no formation of a duplexed structure is required).

The term "cleavage means" or "cleavage agent" as used herein refers to any means that is capable of cleaving a cleavage structure, including but not limited to enzymes. "Structure-specific nucleases" or "structure-specific enzymes" are enzymes that recognize specific secondary structures in a nucleic molecule and cleave these structures. The cleavage means of the invention cleave a nucleic acid molecule in response to the formation of cleavage structures; it is not necessary that the cleavage means cleave the cleavage structure at any particular location within the cleavage structure.

The cleavage means may include nuclease activity provided from a variety of sources including the Cleavase enzymes, the FEN-1 endonucleases (including RAD2 and XPG proteins), Taq DNA polymerase and E. coli DNA polymerase I. The cleavage means may include enzymes having 5' nuclease activity (e.g., Taq DNA polymerase (DNAP), E. coli DNA polymerase I). The cleavage means may also include modified DNA polymerases having 5' nuclease activity but lacking synthetic activity. Examples of cleavage means suitable for use in the method and kits of the present invention are provided in U.S. Pat. Nos. 5,614,402; 5,795,763; 5,843,669; 6,090; PCT Appln. Nos WO 98/23774; WO 02/070755A2; and WO0190337A2, each of which is herein incorporated by reference it its entirety.

The term "thermostable" when used in reference to an enzyme, such as a 5' nuclease, indicates that the enzyme is functional or active (i.e., can perform catalysis) at an elevated temperature, i.e., at about 55° C. or higher.

The term "cleavage products" as used herein, refers to products generated by the reaction of a cleavage means with a cleavage structure (i.e., the treatment of a cleavage structure with a cleavage means).

The term "target nucleic acid" refers to a nucleic acid molecule containing a sequence that has at least partial complementarity with at least a probe oligonucleotide and may also have at least partial complementarity with an INVADER oligonucleotide. The target nucleic acid may comprise single- or double-stranded DNA or RNA.

The term "non-target cleavage product" refers to a product of a cleavage reaction that is not derived from the target nucleic acid. As discussed above, in the methods of the present invention, cleavage of the cleavage structure generally occurs within the probe oligonucleotide. The fragments of the probe oligonucleotide generated by this target nucleic acid-dependent cleavage are "non-target cleavage products."

The term "probe oligonucleotide" refers to an oligonucleotide that interacts with a target nucleic acid to form a cleavage structure in the presence or absence of an INVADER oligonucleotide. When annealed to the target nucleic acid, the probe oligonucleotide and target form a cleavage structure and cleavage occurs within the probe oligonucleotide.

The term "INVADER oligonucleotide" refers to an oligonucleotide that hybridizes to a target nucleic acid at a location near the region of hybridization between a probe and the target nucleic acid, wherein the INVADER oligonucleotide comprises a portion (e.g., a chemical moiety, or nucleotide—whether complementary to that target or not) that overlaps with the region of hybridization between the probe and target. In some embodiments, the INVADER oligonucleotide contains sequences at its 3' end that are substantially the same as sequences located at the 5' end of a probe oligonucleotide.

The term "cassette" as used herein refers to an oligonucleotide or combination of oligonucleotides configured to generate a detectable signal in response to cleavage of a probe oligonucleotide in an INVADER assay. In preferred embodiments, the cassette hybridizes to a non-target cleavage product from cleavage of the probe oligonucleotide to form a second invasive cleavage structure, such that the cassette can then be cleaved.

In some embodiments, the cassette is a single oligonucleotide comprising a hairpin portion (i.e., a region wherein one portion of the cassette oligonucleotide hybridizes to a second portion of the same oligonucleotide under reaction conditions, to form a duplex). In other embodiments, a cassette comprises at least two oligonucleotides comprising complementary portions that can form a duplex under reaction conditions. In preferred embodiments, the cassette comprises a label. In particularly preferred embodiments, cassette comprises labeled moieties that produce a fluorescence resonance energy transfer (FRET) effect.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

As used herein, the phrase "non-amplified oligonucleotide detection assay" refers to a detection assay configured to detect the presence or absence of a particular polymorphism (e.g., SNP, repeat sequence, etc.) in a target sequence (e.g. genomic DNA) that has not been amplified (e.g. by PCR), without creating copies of the target sequence. A "non-amplified oligonucleotide detection assay" may, for example, amplify a signal used to indicate the presence or absence of a particular polymorphism in a target sequence, so long as the target sequence is not copied.

The term "sequence variation" as used herein refers to differences in nucleic acid sequence between two nucleic acids. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene.

The term "liberating" as used herein refers to the release of a nucleic acid fragment from a larger nucleic acid fragment, such as an oligonucleotide, by the action of, for example, a 5' nuclease such that the released fragment is no longer covalently attached to the remainder of the oligonucleotide.

The term "$K_m$" as used herein refers to the Michaelis-Menten constant for an enzyme and is defined as the concentration of the specific substrate at which a given enzyme yields one-half its maximum velocity in an enzyme catalyzed reaction.

The term "nucleotide analog" as used herein refers to modified or non-naturally occurring nucleotides including but not limited to analogs that have altered stacking interactions such as 7-deaza purines (i.e., 7-deaza-dATP and 7-deaza-dGTP); base analogs with alternative hydrogen bonding configurations (e.g., such as Iso-C and Iso-G and other non-standard base pairs described in U.S. Pat. No. 6,001,983 to S. Benner); non-hydrogen bonding analogs (e.g., non-polar, aromatic nucleoside analogs such as 2,4-difluorotoluene, described by B. A. Schweitzer and E. T. Kool, J. Org. Chem., 1994, 59, 7238-7242, B. A. Schweitzer and E. T. Kool, J. Am. Chem. Soc., 1995, 117, 1863-1872); "universal" bases such as 5-nitroindole and 3-nitropyrrole; and universal purines and pyrimidines (such as "K" and "P" nucleotides, respectively; P. Kong, et al., Nucleic Acids Res., 1989, 17, 10373-10383, P. Kong et al., Nucleic Acids Res., 1992, 20, 5149-5152). Nucleotide analogs include comprise modified forms of deoxyribonucleotides as well as ribonucleotides.

The term "polymorphic locus" is a locus present in a population that shows variation between members of the population (e.g., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The term "microorganism" as used herein means an organism too small to be observed with the unaided eye and includes, but is not limited to bacteria, virus, protozoans, fungi, and ciliates.

The term "microbial gene sequences" refers to gene sequences derived from a microorganism.

The term "bacteria" refers to any bacterial species including eubacterial and archaebacterial species.

As used herein, the terms "high-risk HPV strains" or "high-risk HPV types" refer to those strains of HPV that have been found in cancers (e.g., carcinomas). These HPV strains include HPV types 16, 18, 30, 31, 33, 35, 39, 45, 51, 52, 56, 58, 59, 67, 68, 69 and 70.

The term "virus" refers to obligate, ultramicroscopic, intracellular parasites incapable of autonomous replication (i.e., replication requires the use of the host cell's machinery).

The term "multi-drug resistant" or multiple-drug resistant" refers to a microorganism that is resistant to more than one of the antibiotics or antimicrobial agents used in the treatment of said microorganism.

The term "sample" in the present specification and claims is used in its broadest sense. On the one hand it is meant to include a specimen or culture (e.g., microbiological cultures). On the other hand, it is meant to include both biological and environmental samples. A sample may include a specimen of synthetic origin.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The term "source of target nucleic acid" refers to any sample that contains nucleic acids (RNA or DNA). Particularly preferred sources of target nucleic acids are biological samples including, but not limited to blood, saliva, cerebral spinal fluid, pleural fluid, milk, lymph, sputum and semen.

An oligonucleotide is said to be present in "excess" relative to another oligonucleotide (or target nucleic acid sequence) if that oligonucleotide is present at a higher molar concentration that the other oligonucleotide (or target nucleic acid sequence). When an oligonucleotide such as a probe oligonucleotide is present in a cleavage reaction in excess relative to the concentration of the complementary target nucleic acid sequence, the reaction may be used to indicate the amount of the target nucleic acid present. Typically, when present in excess, the probe oligonucleotide will be present at least a 100-fold molar excess; typically at least 1 pmole of each probe oligonucleotide would be used when the target nucleic acid sequence was present at about 10 fmoles or less.

A sample "suspected of containing" a first and a second target nucleic acid may contain either, both or neither target nucleic acid molecule.

The term "reactant" is used herein in its broadest sense. The reactant can comprise, for example, an enzymatic reactant, a chemical reactant or light (e.g., ultraviolet light, particularly short wavelength ultraviolet light is known to break oligonucleotide chains). Any agent capable of reacting with an oligonucleotide to either shorten (i.e., cleave) or elongate the oligonucleotide is encompassed within the term "reactant."

As used herein, the term "purified" or "to purify" refers to the removal of contaminants from a sample. For example, recombinant CLEAVASE nucleases are expressed in bacterial host cells and the nucleases are purified by the removal of host cell proteins; the percent of these recombinant nucleases is thereby increased in the sample.

As used herein the term "portion" when in reference to a protein (as in "a portion of a given protein") refers to fragments of that protein. The fragments may range in size from four amino acid residues to the entire amino acid sequence minus one amino acid (e.g., 4, 5, 6, . . . , n−1).

The term "nucleic acid sequence" as used herein refers to an oligonucleotide, nucleotide or polynucleotide, and fragments or portions thereof, and to DNA or RNA of genomic or synthetic origin that may be single or double stranded, and represent the sense or antisense strand. Similarly, "amino acid sequence" as used herein refers to peptide or protein sequence.

As used herein, the terms "purified" or "substantially purified" refer to molecules, either nucleic or amino acid sequences, that are removed from their natural environment, isolated or separated, and are at least 60% free, preferably 75% free, and most preferably 90% free from other components with which they are naturally associated. An "isolated polynucleotide" or "isolated oligonucleotide" is therefore a substantially purified polynucleotide.

The term "continuous strand of nucleic acid" as used herein is means a strand of nucleic acid that has a continuous, covalently linked, backbone structure, without nicks or other disruptions. The disposition of the base portion of each nucleotide, whether base-paired, single-stranded or mismatched, is not an element in the definition of a continuous strand. The backbone of the continuous strand is not limited to the ribose-phosphate or deoxyribose-phosphate compositions that are found in naturally occurring, unmodified nucleic acids. A nucleic acid of the present invention may comprise modifications in the structure of the backbone, including but not limited to phosphorothioate residues, phosphonate residues, 2' substituted ribose residues (e.g., 2'-O-methyl ribose) and alternative sugar (e.g., arabinose) containing residues.

The term "continuous duplex" as used herein refers to a region of double stranded nucleic acid in which there is no disruption in the progression of basepairs within the duplex (i.e., the base pairs along the duplex are not distorted to accommodate a gap, bulge or mismatch with the confines of the region of continuous duplex). As used herein the term refers only to the arrangement of the basepairs within the duplex, without implication of continuity in the backbone portion of the nucleic acid strand. Duplex nucleic acids with uninterrupted basepairing, but with nicks in one or both strands are within the definition of a continuous duplex.

The term "duplex" refers to the state of nucleic acids in which the base portions of the nucleotides on one strand are bound through hydrogen bonding the their complementary bases arrayed on a second strand. The condition of being in a duplex form reflects on the state of the bases of a nucleic acid. By virtue of base pairing, the strands of nucleic acid also generally assume the tertiary structure of a double helix, having a major and a minor groove. The assumption of the helical form is implicit in the act of becoming duplexed.

The term "template" refers to a strand of nucleic acid on which a complementary copy is built from nucleoside triphosphates through the activity of a template-dependent nucleic acid polymerase. Within a duplex the template strand is, by convention, depicted and described as the "bottom" strand. Similarly, the non-template strand is often depicted and described as the "top" strand.

DESCRIPTION OF THE DRAWINGS

FIG. 1 shows a schematic diagram of INVADER oligonucleotides, probe oligonucleotides and FRET cassettes for detecting a two different alleles (e.g., differing by a single nucleotide) in a single reaction.

FIG. 3 shows sequences of detection assay components in some embodiments of the present invention. Underlined portions of the sequence refer to the 5' arm portion of probe oligonucleotides.

FIG. 6 shows HPV strains detected with Invader assay pools A9, A7 and A5/A6.

FIG. 7 shows sequences of detection assay components in some embodiments of the present invention. Underlined portions of the sequence refer to the 5' arm portion of probe oligonucleotides.

FIG. 10 shows sequences of detection assay components in some embodiments of the present invention. Underlined portions of the sequence refer to the 5' arm portion of probe oligonucleotides.

DESCRIPTION OF THE INVENTION

Figure 2:
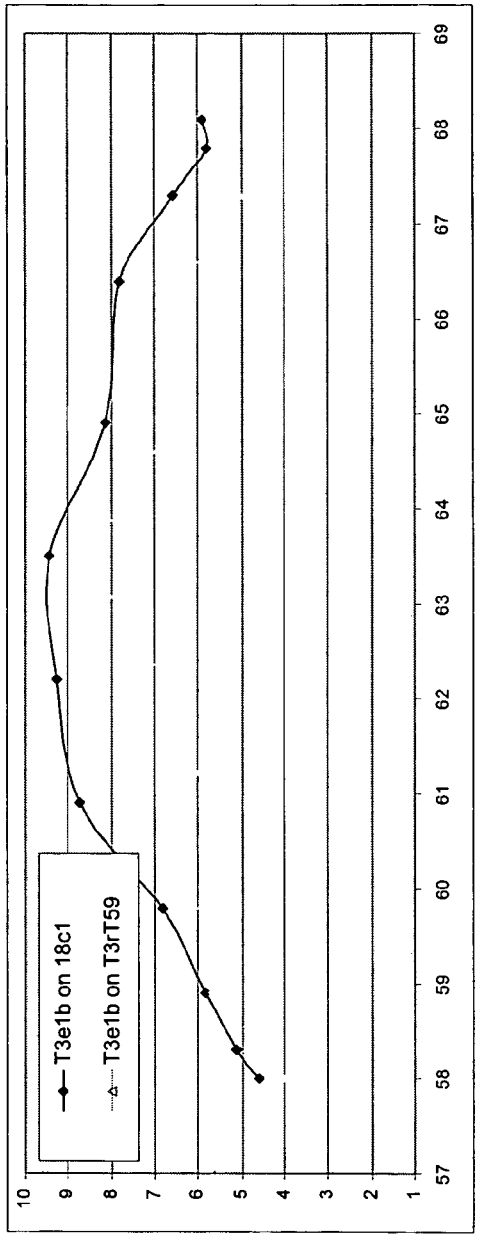
FIG. 2 shows the results of a temperature optimization experiment carried out in some embodiments of the present invention.

The present invention provides means for forming a nucleic acid cleavage structure that is dependent upon the presence of a target nucleic acid and cleaving the nucleic acid cleavage structure so as to release distinctive cleavage products. 5' nuclease activity, for example, is used to cleave the target-dependent cleavage structure and the resulting cleavage products are indicative of the presence of specific target nucleic acid sequences in the sample. When two strands of nucleic acid, or oligonucleotides, both hybridize to a target nucleic acid strand such that they form an overlapping invasive cleavage structure, as described below, invasive cleavage can occur. Through the interaction of a cleavage agent (e.g., a 5' nuclease) and the upstream oligonucleotide, the cleavage agent can be made to cleave the downstream oligonucleotide at an internal site in such a way that a distinctive fragment is produced. Such embodiments have been termed the INVADER assay (Third Wave Technologies) and are described in U.S. patent application Nos. 5,846,717, 5,985, 557, 5,994,069, 6,001,567, and 6,090,543, WO 97/27214 WO 98/42873, Lyamichev et al., Nat. Biotech., 17:292 (1999), Hall et al., PNAS, USA, 97:8272 (2000), each of which is herein incorporated by reference in their entirety for all purposes).

The INVADER assay detects hybridization of probes to a target by enzymatic cleavage of specific structures by structure specific enzymes (See, INVADER assays, Third Wave Technologies; See e.g., U.S. Pat. Nos. 5,846,717; 6,090,543; 6,001,567; 5,985,557; 6,090,543; 5,994,069; Lyamichev et al., Nat. Biotech., 17:292 (1999), Hall et al., PNAS, USA, 97:8272 (2000), WO97/27214 and WO98/42873, each of which is herein incorporated by reference in their entirety for all purposes).

The INVADER assay detects specific DNA and RNA sequences by using structure-specific enzymes (e.g. FEN endonucleases) to cleave a complex formed by the hybridization of overlapping oligonucleotide probes (See, e.g. FIG. 1). Elevated temperature and an excess of one of the probes enable multiple probes to be cleaved for each target sequence present without temperature cycling. In some embodiments, these cleaved probes then direct cleavage of a second labeled probe. The secondary probe oligonucleotide can be 5'-end labeled with fluorescein that is quenched by an internal dye. Upon cleavage, the de-quenched fluorescein labeled product may be detected using a standard fluorescence plate reader.

The INVADER assay detects specific mutations and SNPs in unamplified, as well as amplified, RNA and DNA including genomic DNA. In the embodiments shown schematically in FIG. 1, the INVADER assay uses two cascading steps (a primary and a secondary reaction) both to generate and then to amplify the target-specific signal. For convenience, the alleles in the following discussion are described as wild-type (WT) and mutant (MT), even though this terminology does not apply to all genetic variations. In the primary reaction (FIG. 1, panel A), the WT primary probe and the INVADER oligonucleotide hybridize in tandem to the target nucleic acid to form an overlapping structure. An unpaired "flap" is included on the 5' end of the WT primary probe. A structure-specific enzyme (e.g. the CLEAVASE enzyme, Third Wave Technologies) recognizes the overlap and cleaves off the unpaired flap, releasing it as a target-specific product. In the secondary reaction, this cleaved product serves as an INVADER oligonucleotide on the WT fluorescence resonance energy transfer (WT-FRET) probe to again create the structure recognized by the structure specific enzyme (panel A). When the two dyes on a single FRET probe are separated by cleavage (indicated by the arrow in FIG. 1), a detectable fluorescent signal above background fluorescence is produced. Consequently, cleavage of this second structure results in an increase in fluorescence, indicating the presence of the WT allele (or mutant allele if the assay is configured for the mutant allele to generate the detectable signal). In some embodiments, FRET probes having different labels (e.g. resolvable by difference in emission or excitation wavelengths, or resolvable by time-resolved fluorescence detection) are provided for each allele or locus to be detected, such that the different alleles or loci can be detected in a single reaction. In such embodiments, the primary probe sets and the different FRET probes may be combined in a single assay, allowing comparison of the signals from each allele or locus in the same sample.

If the primary probe oligonucleotide and the target nucleotide sequence do not match perfectly at the cleavage site (e.g., as with the MT primary probe and the WT target, FIG. 1, panel B), the overlapped structure does not form and cleavage is suppressed. The structure specific enzyme (e.g., CLEAVASE VIII enzyme, Third Wave Technologies) used cleaves the overlapped structure more efficiently (e.g. at least 340-fold) than the non-overlapping structure, allowing excellent discrimination of the alleles.

The probes turn over without temperature cycling to produce many signals per target (i.e., linear signal amplification). Similarly, each target-specific product can enable the cleavage of many FRET probes.

The primary INVADER assay reaction is directed against the target DNA (or RNA) being detected. The target DNA is the limiting component in the first invasive cleavage, since the INVADER and primary probe are supplied in molar excess. In the second invasive cleavage, it is the released flap that is limiting. When these two cleavage reactions are performed sequentially, the fluorescence signal from the composite reaction accumulates linearly with respect to the target DNA amount.

In certain embodiments, the INVADER assay, or other nucleotide detection assays, are performed with accessible site designed oligonucleotides and/or bridging oligonucleotides. Such methods, procedures and compositions are described in U.S. Pat. No. 6,194,149, WO9850403, and WO0198537, all of which are specifically incorporated by reference in their entireties.

In certain embodiments, the target nucleic acid sequence is amplified prior to detection (e.g. such that synthetic nucleic acid is generated). In some embodiments, the target nucleic acid comprises genomic DNA. In other embodiments, the target nucleic acid comprises synthetic DNA or RNA. In some preferred embodiments, synthetic DNA within a sample is created using a purified polymerase. In some preferred embodiments, creation of synthetic DNA using a purified polymerase comprises the use of PCR. In other preferred embodiments, creation of synthetic DNA using a purified DNA polymerase, suitable for use with the methods of the present invention, comprises use of rolling circle amplification, (e.g., as in U.S. Pat. Nos. 6,210,884, 6,183,960 and 6,235,502, herein incorporated by reference in their entireties). In other preferred embodiments, creation of synthetic DNA comprises copying genomic DNA by priming from a plurality of sites on a genomic DNA sample. In some embodiments, priming from a plurality of sites on a genomic DNA sample comprises using short (e.g., fewer than about 8 nucleotides) oligonucleotide primers. In other embodiments, priming from a plurality of sites on a genomic DNA comprises extension of 3' ends in nicked, double-stranded genomic DNA (i.e., where a 3' hydroxyl group has been made available for extension by breakage or cleavage of one strand of a double stranded region of DNA). Some examples of making synthetic DNA using a purified polymerase on nicked genomic DNAs, suitable for use with the methods and compositions of the present invention, are provided in U.S. Pat. No. 6,117,634, issued Sep. 12, 2000, and U.S. Pat. No. 6,197,557, issued Mar. 6, 2001, and in PCT application WO 98/39485, each incorporated by reference herein in their entireties for all purposes.

In some embodiments, the present invention provides methods for detecting a target sequence, comprising: providing a) a sample containing DNA amplified by extension of 3' ends in nicked double-stranded genomic DNA, said genomic DNA suspected of containing said target sequence; b) oligonucleotides capable of forming an invasive cleavage structure in the presence of said target sequence; and c) exposing the sample to the oligonucleotides and the agent. In some embodiments, the agent comprises a cleavage agent. In some particularly preferred embodiments, the method of the invention further comprises the step of detecting said cleavage product.

In some preferred embodiments, the exposing of the sample to the oligonucleotides and the agent comprises exposing the sample to the oligonucleotides and the agent under conditions wherein an invasive cleavage structure is formed between said target sequence and said oligonucleotides if said target sequence is present in said sample, wherein said invasive cleavage structure is cleaved by said cleavage agent to form a cleavage product.

In some particularly preferred embodiments, the target sequence comprises a first region and a second region, said second region downstream of and contiguous to said first region, and said oligonucleotides comprise first and second oligonucleotides, said wherein at least a portion of said first oligonucleotide is completely complementary to said first portion of said target sequence and wherein said second oligonucleotide comprises a 3' portion and a 5' portion, wherein said 5' portion is completely complementary to said second portion of said target nucleic acid.

In other embodiments, synthetic DNA suitable for use with the methods and compositions of the present invention is made using a purified polymerase on multiply-primed genomic DNA, as provided, e.g., in U.S. Pat. Nos. 6,291,187, and 6,323,009, and in PCT applications WO 01/88190 and WO 02/00934, each herein incorporated by reference in their entireties for all purposes. In these embodiments, amplification of DNA such as genomic DNA is accomplished using a DNA polymerase, such as the highly processive Φ 29 polymerase (as described, e.g., in U.S. Pat. Nos. 5,198,543 and 5,001,050, each herein incorporated by reference in their entireties for all purposes) in combination with exonuclease-resistant random primers, such as hexamers.

In some embodiments, the present invention provides methods for detecting a target sequence, comprising: providing a) a sample containing DNA amplified by extension of multiple primers on genomic DNA, said genomic DNA suspected of containing said target sequence; b) oligonucleotides capable of forming an invasive cleavage structure in the presence of said target sequence; and c) exposing the sample to the oligonucleotides and the agent. In some embodiments, the agent comprises a cleavage agent. In some preferred embodiments, said primers are random primers. In particularly preferred embodiments, said primers are exonuclease resistant. In some particularly preferred embodiments, the method of the invention further comprises the step of detecting said cleavage product.

In some preferred embodiments, the exposing of the sample to the oligonucleotides and the agent comprises exposing the sample to the oligonucleotides and the agent under conditions wherein an invasive cleavage structure is formed between said target sequence and said oligonucleotides if said target sequence is present in said sample, wherein said invasive cleavage structure is cleaved by said cleavage agent to form a cleavage product.

In some preferred embodiments, the exposing of the sample to the oligonucleotides and the agent comprises exposing the sample to the oligonucleotides and the agent under conditions wherein an invasive cleavage structure is formed between said target sequence and said oligonucleotides if said target sequence is present in said sample, wherein said invasive cleavage structure is cleaved by said cleavage agent to form a cleavage product.

In some particularly preferred embodiments, the target sequence comprises a first region and a second region, said second region downstream of and contiguous to said first region, and said oligonucleotides comprise first and second oligonucleotides, said wherein at least a portion of said first oligonucleotide is completely complementary to said first portion of said target sequence and wherein said second oligonucleotide comprises a 3' portion and a 5' portion, wherein said 5' portion is completely complementary to said second portion of said target nucleic acid.

In certain embodiments, the present invention provides kits for assaying a pooled sample (e.g., a pooled blood sample) using INVADER detection reagents (e.g. primary probe, INVADER probe, and FRET cassette). In preferred embodiments, the kit further comprises instructions on how to perform the INVADER assay and specifically how to apply the INVADER detection assay to pooled samples from many individuals, or to "pooled" samples from many cells (e.g. from a biopsy sample) from a single subject.

The present invention further provides assays in which the target nucleic acid is reused or recycled during multiple rounds of hybridization with oligonucleotide probes and cleavage of the probes without the need to use temperature cycling (i.e., for periodic denaturation of target nucleic acid strands) or nucleic acid synthesis (i.e., for the polymerization-based displacement of target or probe nucleic acid strands). When a cleavage reaction is run under conditions in which the probes are continuously replaced on the target strand (e.g. through probe-probe displacement or through an equilibrium between probe/target association and disassociation, or through a combination comprising these mechanisms, (The kinetics of oligonucleotide replacement. Luis P. Reynaldo, Alexander V. Vologodskii, Bruce P. Neri and Victor I. Lyamichev. J. Mol. Biol. 97: 511-520 (2000)), multiple probes can hybridize to the same target, allowing multiple cleavages, and the generation of multiple cleavage products.

In some embodiments, the detection assays of the present invention are designed to detect one or more HPV sequences (See, e.g., Example 5). In some embodiments, multiple HPV sequences are detected in a single reaction (See, e.g., Example 5, FIG. 9, reactions 10-658, 10-662, 10-677 and 10-682). In some preferred embodiments, a single oligonucleotide used in the detection assays is configured to hybridize to two or more HPV sequences such that multiple HPV sequences can be detected with a single set of detection assay reagents (See, e.g., Example 5, FIG. 9). In some embodiments, the oligonucleotides used in the detection assay are perfectly complementary to the intended HPV target sequence. In other embodiments, the oligonucleotides contain one or more mismatches to the HPV target sequence of interest. Mismatches find multiple uses, including, but not limited to, the ability to reduce hybridization efficiency (which may be desired in some detection assay formats), the ability to add degeneracy (e.g., to detect two or more strains or variants), and the ability to compensate for sequence variation that may be in a sample. In some embodiments, where variation at a particular nucleotide position is identified in some members of a tested population, multiple oligonucleotides are provides that differ in sequence at the position so that each variant within the population is detected. Exemplary detection assay components for use in invasive cleavage assays are provided in the Example section below for certain preferred strains of HPV.

EXAMPLES

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); l or L (liters); ml (milliliters); µl (microliters); cm (centimeters); mm (millimeters); µm (micrometers); nm (nanometers); DS (dextran sulfate); ° C. (degrees Centigrade); and Sigma (Sigma Chemical Co., St. Louis, Mo.).

Example 1

Design of Oligonucleotides to Detect Multiple HPV Strains

The objective of these experiments was to arrive at oligonucleotide designs suitable for use in INVADER assays comprising multiple target HPV strains. As a first step, HPV DNA sequences were obtained from Genbank and aligned using SEQ WEB GAP and PRETTY programs (Accelrys, San Diego, Calif.). Only those regions of HPV that are reported to remain intact following chromosomal integration were analyzed to permit the assays to detect both integrated and non-integrated HPV sequences. Regions of suitable sequence conservation were chosen for select groups of strains. In this example, areas within the LCR, E6, and E7 genes were found to have considerable homology between HPV 18 and 59.

Candidate probe oligonucleotides were designed by searching for stretches of sequence comprising a limited number of mismatches between the two targets in either pair. Designs were generated to several sequences on either the sense or antisense strands. Suitable INVADER oligonucleotides were designed to accompany the respective probe oligonucleotide candidates. Initial INVADER oligonucleotide designs were selected to associate with only a single target, e.g. HPV 18, HPV 45, or HPV 59; subsequent designs hybridize to more than one HPV strain. Candidate probe sets were then evaluated for two types of performance criteria: (1) signal generation at the chosen reaction temperature and (2) limit of detection, i.e. signal over background ratios at low levels of target DNA. Probe sets meeting desired performance cut-offs, in this case, optimal signal generation at 63° C. and LOD of ≦1000 copies of HPV DNA, were then selected for further evaluation.

Temperature Optimization

INVADER assays were performed in 96 well MJ Skirted microtiter plates. Plates were incubated using either an MJ Research PTC100 Thermocycler or a ThermoHybaid PCR Express (Molecular Biology Instrumentation, Needham Heights, Mass.) and read with an Applied Biosystems CYTOFLUOR® 4000 series multiwell plate reader.

INVADER assays to determine temperature optima of probe sets were set up by preparing primary and secondary reaction master mixes. In these experiments, two different INVADER oligonucleotides were tested in combination with a single probe oligonucleotide in each reaction. For example, in experiments designed to test probe sets for HPV 18 and 59, INVADER oligonucleotides for both HPV 18 and HPV 59 were included in each reaction along with a single probe oligonucleotide designed to associate with both strains of HPV. These reaction mixtures were tested separately on plasmid DNA comprising a portion of the HPV 18 (18c1) sequence (ATCC Catalog Number: 45152D) and a synthetic target comprising a portion of the HPV 59 sequence (SEQ ID NO: 42). Similarly, in experiments designed to detect HPV 45 and 59, INVADER oligonucleotides for both strains were included in each reaction along with the corresponding probe oligonucleotide and appropriate controls.

Master mixes containing primary reaction components were assembled for each set of temperature optimization reactions as follows. Reactions were carried out in parallel in microtiter plates.

| Reagent | Primary Mix (PM) | | | | |
| --- | --- | --- | --- | --- | --- |
|  | Stock Conc. | Final Conc. | # Rxns | Vol/ Rxn | Total Vol |
| Invader Oligo 1 (µM) | 10 | 0.05 | 120 | 0.10 | 12 |
| Invader Oligo 2 (µM) | 10 | 0.05 |  | 0.10 | 12 |
| Primary Probe (µM) | 10 | 0.5 |  | 1.00 | 120 |
| MOPS (mM) | 400 | 10 |  | 0.50 | 60 |
| CLEAVASE X enzyme (ng/µl) | 50 | 2.5 |  | 1.00 | 120 |
| MgCl$_2$ (mM) | 250 | 12.5 |  | 1.00 | 120 |
| Distilled Water | 0 | 0 |  | 0.30 | 36 |
|  |  |  |  | 4.00 µl/rxn |  |

Aliquots of 15 µl of each target at a concentration of 20 fM were placed in the appropriate wells of a microtiter plate and were overlaid with 20 µl of mineral oil; 20 µl of 10 ng/µl tRNA were used for the no target control reactions. All reactions were run in duplicate. The targets were heat denatured at 95° C. for 5 minutes, cooled to 20° C., and then aliquots of 4 µl of the primary mix were added to each well. The microtiter plates were incubated for 2 hours in a ThermoHybaid thermocycler with a gradient heat block over a span of 10 degrees (i.e. reactions were run at 58, 58.3, 58.9, 59.8, 60.9, 62.2, 63.5, 64.9, 66.4, 67.3, 67.8, 68.1° C.) and then returned to 20° C.

A secondary master mix (SM) was assembled as follows.

Secondary Mix (SM)

| Reagent | Stock Conc. | Final Conc. | Vol/Rxn | Total Vol |
|---|---|---|---|---|
| FRET Cassette Arm 1 FAM SEQ ID NO: 63 (µM) | 10 | 0.25 | 0.50 | 62.50 |
| MOPS (mM) | 400 | 0.91 | 0.05 | 5.68 |
| Water | — | — | 2.45 | 306.82 |
| | | | 3 µl/rxn | |

Aliquots of 3 µl of secondary mix were then added to each well, and the plate was incubated at 63° C. for 10 minutes and then cooled to 4° C. prior to scanning in a CYTOFLUOR 4000 fluorescence plate reader (Applied Biosystems, Foster City, Calif.). The settings used were: 485/20 nm excitation/bandwidth and 530/25 nm emission/bandwidth for FAM dye detection. Unlike typical biplex INVADER reactions, because these assays include only a single probe molecule, only the single corresponding FRET cassette is required. The instrument gain was set for each dye so that the No Target Blank produced between 50-150 Relative Fluorescence Units (RFUs).

Because the optimal gain setting can vary between instruments, gain is adjusted as needed to give the best signal/background ratio (sample raw signal divided by the No Target Control signal) or No Target Control sample readings of ~100 RFUs. Fluorescence microplate readers that use a xenon lamp source generally produce higher RFUs. For directly reading the microplates, the probe height of, and how the plate is positioned in, the fluorescence microplate reader may need to be adjusted according to the manufacturer's recommendations.

The raw data that is generated by the device/instrument is used to measure the assay performance (real-time or endpoint mode). The equations below provide how FOZ (Fold Over Zero), and other values are calculated. NTC in the equations below represents the signal from the No Target Control.

FOZ or Signal/No Target $$FOZ_{Dye}=(RawSignal_{Dye}/NTC_{Dye})$$

Candidate probe sets were selected based on the temperature profiles generated in these experiments. In particular, desirable probe sets exhibit temperature profiles on the two targets (e.g. HPV 18 and 59) tested together that exhibit similar trends with respect to increase in temperature, typically a bell shaped curve with its peak at the chosen reaction temperature, in this case 63° C. An additional desirable feature is that the peak not be precipitously lower plus or minus 1 or 2 degrees from 63° C. Fewer than 30% of the candidate probe sets yielded suitable temperature profiles.

In order to unify reaction conditions at a single reaction temperature, probe designs that gave rise to similar trends in response to temperature were chosen for further design optimization. Redesigned probes in which probe length was altered were tested. FIG. 2 shows the results of a temperature optimization experiment carried out with probe T3e1b (SEQ ID NO:39) and INVADER oligonucleotides designed to detect HPV 18 (T3e4i) (SEQ ID NO:40) and HPV 59 (T3e6i) (SEQ ID NO:41), respectively, on both the HPV 18 plasmid and HPV 59 (T3rT59) synthetic target (SEQ ID NO:42).

Similar temperature optimization and redesign procedures were carried out for all of the oligonucleotides presented in FIGS. 3 and 7.

Limit of Detection (LOD) Analysis

In addition to optimizing for temperature profiles that follow the same general trends in response to temperature and do not present steep slopes in the immediate vicinity of the target reaction temperature, it is also desirable to optimize probe sets for analytical sensitivity or limit of detection (LOD). Measuring LOD is accomplished by conducting INVADER assays at a single reaction temperature while varying target concentration.

Reactions to determine LOD of temperature optimized probe sets were set up as follows. A dilution series of target DNAs (HPV 18 plasmid and synthetic target SEQ ID NO: 42) was made in 10 ng/µl tRNA in dH$_2$O; in the example presented here, target amounts per assay ranged from 125 copies/rxn to 8000 copies/rxn, doubling in each successive reaction. Aliquots of 15 µl of diluted target or 10 ng/µl tRNA in dH$_2$O for the no target controls were placed in appropriate wells of a microtiter plate and overlaid with 20 µl of mineral oil. All reactions were run in quadruplicate. A master mix (MM) was made containing buffer, CLEAVASE X enzyme, MgCl$_2$, both INVADER oligonucleotides (SEQ ID NOs: 40-41), primary probe T3e1b (SEQ ID NO: 39) and FRET cassette oligonucleotides (SEQ ID NO: 63) as below.

Master Mix (MM): no. rxns 125

| Reagent | Stock Conc. | Final Conc. | Vol/Rxn | Total Vol |
|---|---|---|---|---|
| FRET Cassette (µM) | 10 | 0.25 | 0.5 | 62.5 |
| MOPS (mM) | 400 | 10 | 0.5 | 62.5 |
| CLEAVASE X enzyme (ng/µl) | 50 | 2.5 37 | 1 | 125 |
| MgCl2 (mM) | 250 | 12.5 | 1 | 125 |
| Invader oligo 1 (µM) | 10 | 0.05 | 0.1 | 12.5 |
| Invader oligo 2 (uM) | 10 | 0.05 | 0.1 | 12.5 |
| Primary Probe (µM) | 10 | 0.5 | 1 | 125 |
| water | N/A | N/A | 0.8 | 100 |
| total volume | | | 5 | 625 |

Microtiter plates were covered and incubated at 95° C. for 5 minutes to denature the targets and then cooled to 20° C. Aliquots of 5 µl of master mix were added and the reactions heated to 63° C. for 4 hours. Upon completion, plates were removed to the CYTOFLUOR plate reader and analyzed as described above. Representative results are presented FIG. 2. These results demonstrate that the designs tested in this experiment are suitable for the detection of as few as 250 copies of the corresponding HPV 18 and 59 sequences.

Example 2

Design of Oligonucleotides to Detect HPV 16

Candidate oligonucleotide sets having a primary probe and an INVADER oligonucleotide were designed to detect regions in both HPV 16 and HPV 31 using the procedures described in the preceding examples. Designs were directed to the E7 gene of HPV. As in Example 1, different INVADER oligonucleotide sequences were tested in combination with a single probe sequence to find a probe set with optimal performance characteristics at the desired reaction temperature (63° C.) and in terms of limit of detection (FOZ). Both temperature optimization experiments and LOD (FOZ) experiments were conducted as described above using 15 µl of a 20 fM stock solution of HPV 16 plasmid (ATCC Catalog Number: 45113D). A total of 24 different INVADER oligonucleotides were tested with SEQ ID NO: 1 (Alg3p); of these, one was chosen for use in assays to detect HPV 16: SEQ ID NO: 2 (Alg10ci), based on its temperature optimization profile and FOZ.

Co-Detection of HPV 16 and a Human Genomic Internal Control Sequence

In some applications, it is desirable to co-detect an internal control sequence, for example in order to determine whether or not there are sample inhibition effects or operator errors. Oligonucleotide sets were designed to detect three different human genomic sequences and were tested in three different biplexed INVADER assays in combination with SEQ ID NOs: 1 and 2 to detect the HPV 16 plasmid. The human genomic regions were alpha actin (Genbank accession number NM_001100), the 3' untranslated region (UTR) of CFTR (Genbank accession number NM_000492), and hIGF (Genbank accession number AY260957). The oligonucleotides used for these designs were developed previously and optimized as described in the previous examples and were as follows: alpha actin probe SEQ ID NO: 64, INVADER oligo, SEQ ID NO: 65, FRET cassette 68; 3' UTR CFTR probe SEQ ID NO: 66, INVADER oligo SEQ ID NO: 67, FRET cassette SEQ ID NO: 68; hIGF probe SEQ ID NO: 69, INVADER oligo SEQ ID NO: 70, FRET cassette SEQ ID NO: 71.

Figure 4:
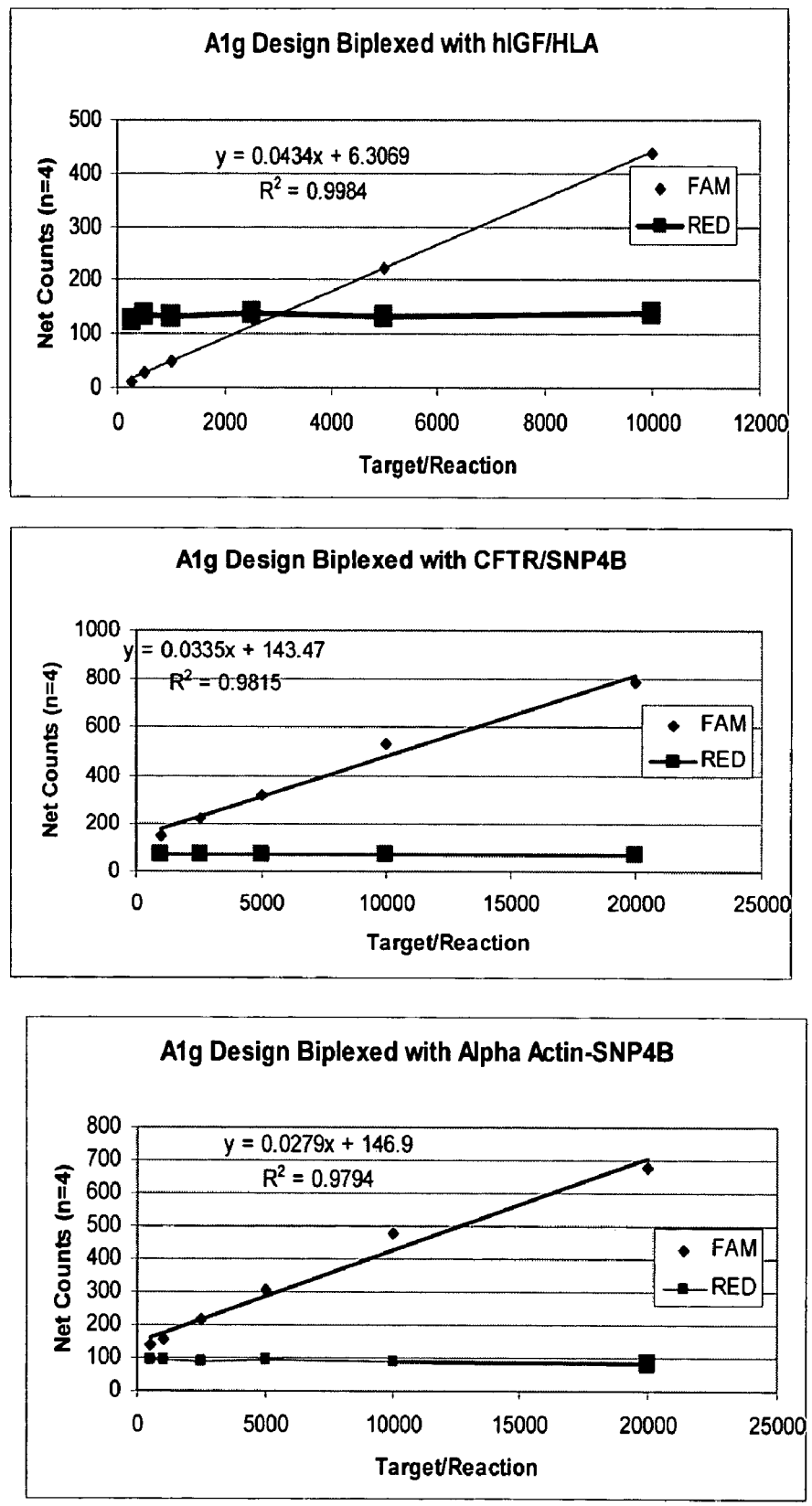
FIG. 4 shows results of HPV strain 16 detection experiments conducted in some embodiments of the present invention.

A standard curve was generated using different amounts of HPV 16 plasmid against a constant amount of human genomic DNA. Reactions containing 0, 250, 500, 1000, 2500, 5000, 10,000, or 20,000 copies of the HPV 16 plasmid and either 100 ng (for hIGF and CFTR) or 250 ng (for alpha actin) human genomic DNA. DNA was isolated using the Gentra PUREGENE® Autopure LS system (Gentra, Inc., Minneapolis, Minn.) or manual preparation methods. All other reaction components and detection were as described in the previous examples except that a second FRET oligo was used in each case (for hIGF, SEQ ID NO: 71, red dye; for 3' UTR of CFTR and alpha actin, SEQ ID NO: 68, red dye). The results are presented in FIG. 4 and indicate that all of the human genomic sequences tested were suitable for biplex detection in combination with varying levels of HPV 16 plasmid DNA. Furthermore, these experiments demonstrate that there is no apparent cross reactivity between the probe sets designed to detect HPV 16 and those designed to detect the human genomic sequences, as evidenced by both the unchanged signal generated using the IC probes in the presence of variable amounts of HPV 16 DNA as well as by the lack of detectable signal generated using the HPV 16 probes in the absence of HPV 16 plasmid DNA.

Example 3

Effects of Genomic DNA on Detection of HPV 18

Experiments were carried out to assess the effect of exogenous human genomic DNA on detection of HPV 18. INVADER reactions were set up as follows. Serial dilutions of a synthetic HPV 18 target B1T18 (SEQ ID NO: 72) were made to result in numbers of target molecules as indicated in the X-axis of FIG. 5 when 15 µl were pipetted into the appropriate wells of a microtiter plate. A second set of serial dilutions was made incorporating human genomic DNA, purified as described in Example 2, into each dilution such that each reaction contained 1 µg of human genomic DNA. No target controls contained 15 µl of 10 ng/µl tRNA in distilled water. All reactions were run in duplicate. The target aliquots were overlaid with 20 µl mineral oil and denatured at 95° C. for 5 minutes then chilled to 20° C. A master mix containing INVADER reaction components was made as follows.

| Reagent | Stock Conc. | Final Conc. | # of reactions | Volume/ reaction | Total volume |
| --- | --- | --- | --- | --- | --- |
| INVADER oligo mixture (SEQ ID NO: 73, 74, and 75) (µM) | 1 | 0.05 | 10 | 1 | 10 |
| Primary probe (SEQ ID NO: 76) B1b3 (µM) | 10 | 0.5 | | 1 | 10 |
| FRET Cassette (SEQ ID NO: 63) (µM) | 10 | 0.25 | | 0.5 | 5 |
| MOPS (mM) | 400 | 10 | | 0.5 | 5 |
| CLEAVASE X enzyme (ng/µl) | 50 | 2.5 | | 1 | 10 |
| MgCl$_2$ (mM) | 250 | 12.5 | | 1 | 10 |
| Total volume | | | | 5 | 50 |

Aliquots of 5 µl of the master mix were added to each well. Reactions were incubated at 62° C. for 4 hours and then read in the CYTOFLUOR as described above.

Figure 5:
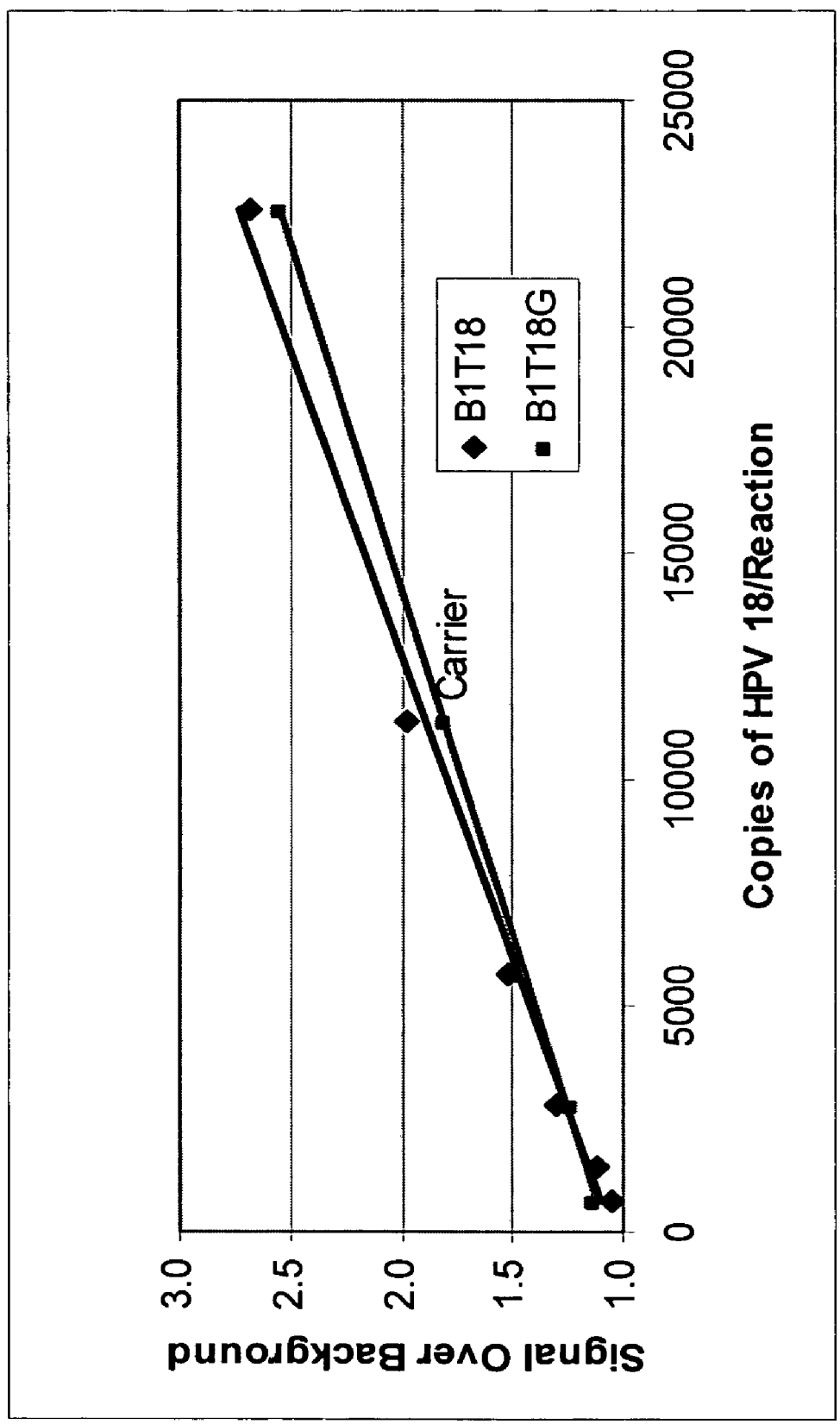
FIG. 5 shows results of HPV strain 18 detection experiments conducted in some embodiments of the present invention.

The results are presented in FIG. 5 and demonstrate that the presence of 1 µg of human genomic DNA does not exert a significant inhibitory effect on the INVADER assay designed to detect HPV 18 sequences.

Example 4

Simultaneous Detection of Multiple HPV Strains in a Single Pooled Reaction

In some situations, it may prove desirable to combine detection of many HPV strains in a single reaction vessel. For example, it may be desired to detect all high-risk HPV strains or all low-risk strains in a single reaction mixture. In some cases, the output of a pooled reaction is a qualitative answer such as a positive result, indicating the presence of one or more HPV strains, or a negative result, indicating the absence of HPV.

Preferred oligonucleotide designs for pooling multiple INVADER reactions in a single well may possess the following characteristics:

The oligonucleotides do not interact with one another to promote excessive signal generation in the absence of a specific target. Background in the INVADER assay may result from fragments of certain oligonucleotides that are an intrinsic component of some oligo synthesis mixtures. However, it is also possible for groups of different oligonucleotides to assume structures that are recognized and cleaved during the INVADER assay in the absence of target.

The oligonucleotides do not interact with one another to interfere significantly with signal generation in the presence of a specific target.

Performance of a given oligonucleotide set is comparable when tested in the pooled mixture and individually.

Pooled assays are created by combining probe and INVADER oligonucleotides in subcombinations and then assessing performance on each target by comparing signal generation and FOZ of the oligonucleotides in the pool to detection of that target in reactions containing only the probe and INVADER oligonucleotides designed to detect it. In the event that a given oligonucleotide set is adversely affected by combination with other oligo sets in a single reaction vessel, e.g. generates excessive background or fails to generate the expected levels of target-specific signal, in some cases it is possible to swap in an alternative oligonucleotide set useful for determining the presence of the same HPV strain. In other cases, it is possible to merely choose a different 5' arm for a particular probe oligonucleotide to reduce non-specific background generation or signal inhibition. In some cases, it is possible to detect the alternative strand of a particular target sequence, thereby altering the composition of the oligonucleotides and making them suitable for detection of the target in a pooled assay. In each case, the measure of a successfully performing assay is yield of statistically significant signal over background (FOZ) in the presence of the desired targets, e.g. ≧1.15 with t-test from neighbor <0.05.

Ultimately, candidate oligonucleotide designs are pooled in various combinations and tested against a sample containing purified HPV DNA or partial HPV sequences. Optimally, samples of all HPV strains being tested are evaluated individually with the pooled oligonucleotide sets to confirm that target-specific signal is generated for each desired strain. Similarly, HPV negative samples or samples containing strains of HPV not desired to be tested (e.g. low risk strains, HPV 1, or other non-cervical strains) are also tested against the pools to confirm that they do not generate statistically significant FOZ.

Example 5

Detection of Multiple HPV Strains in Cervical Samples

The methods and compositions of the present invention were used, as described in Example 4, to detect multiple strains of HPV in cervical samples.

INVADER Oligonucleotide Designs

The INVADER assay was designed to detect high-risk HPV strains including 16, 18, 31, 33, 35, 39, 45, 51, 52, 56, 58, 59, 67, 68, and 70. Probe sets were combined into three pools based on HPV genetic phylogeny. Probe sets (e.g., probe and INVADER oligonucleotides) were designed to hybridize to at least 2 different target regions for each HPV strain to accommodate for sequence polymorphisms and increase analytical sensitivity (See, e.g., FIG. 6). Multiple HPV strains are detected by each of the three pools using the INVADER assay (See, e.g., FIG. 6). Probe and INVADER oligonucleotide sequences are listed in FIG. 7. The probe and INVADER oligonucleotide sequences in FIG. 10 may also be used. An internal control assay (alpha-actin) is included in each pool to measure the relative amount of genomic DNA levels in the samples and to provide a semi-quantitative method for HPV titer. The HPV specific probes in the A7 and A9 pools contained arm 1 (CGCGCCGAGG; SEQ ID NOS: 85, 88, 91, 94, 97, 101, 105, 108, 110, and 114) and utilized the corresponding FAM FRET cassette (Fam-TCT-Z28-AGCCGGTTTTCCGGCTGAGACCTCGGCGCG-hex, SEQ ID NO: 119). The HPV specific probes in the A5/A6 pool contained arm AH9 (GGCAGTCTGGGAGT, SEQ ID NO: 77, 79, 81, and 83) and utilized the FAM FRET cassette (Fam-TCT-Z28-AGCCGGTTTTCCGGCTGAGAACTC-CCAGACTGCC-hex, SEQ ID NO: 120). The alpha-actin assay contained arm 3(ACGGACGCGGAG; SEQ ID NO: 117) and utilized the RED FRET cassette (Red-TCT-Z28-TCGGCCTTTTGGCCGAGAGACTCCGCGTCCGT-hex, SEQ ID NO. 121).

INVADER Assay Reagents and Methods

Preparation of genomic DNA from cervical samples: DNA was isolated from cervical samples obtained from a clinical laboratory using PUREGENE (Gentra Systems) DNA Purification Kit. The extraction procedure was modified to increase DNA yield and purity from this type of specimen using the following procedure:

1. Remove 1 ml of cervical specimen and transfer to 1.5 ml tube.
2. Centrifuge cells at 16000 g for 5 min.
3. Remove supernatant and resuspend pellet in Cell Lysis Solution
4. Heat lysates at 99° C. for 10 minutes. Let cool to room temperature.
5. Add proteinase K and incubate at 55 for 1 hour.
6. Add 100 µl of protein precipitation solution.
7. Vortex samples vigorously for 20 seconds. Place on ice for 10 minutes.
8. Centrifuge at 16000 g for 5 min.
9. Pour off the supernatant into a clean 1.5 ml tube containing 1.5 µl of glycogen (20 mg/ml)
10. Add 300 µl of 100% isopropanol.
11. Mix the sample gently by inverting 50 times.
12. Centrifuge at 16000 g for 5 min.
13. Pour off the supernatant and drain tube on clean absorbent paper.
14. Add 500 µl of 70% ethanol and invert the tube to wash the DNA pellet.
15. Centrifuge at 16000 g for 2 min. Carefully pour off supernatant.
16. Invert and drain the tube on a clean absorbent paper and allow to air dry for 10-15 min.
17. Add 100 µl of distilled water to the pellet.
18. Let sit at room temperature overnight.

10 µl aliquots of each genomic DNA sample or no target control (10 ng/µl tRNA) were added to a 96 well microtiter plate. Samples were overlaid with 20 µl mineral oil, denatured at 99° C. for 10 minutes and then cooled to 63° C. A 10 µl aliquot of the INVADER reaction mix was then added to each well and mixed by pipetting. An example of what is contained in the INVADER assay reaction mix is shown below.

| Component | Amount per reaction | Final concentrations (in 20 µl reaction) |
|---|---|---|
| MgCl2 (70 mM) | 4 µl | 14 mM MgCl$_2$ |
| HPV Pooled Primary probes and INVADER oligos/FAM FRET/MOPS Stock conc. 2.5 µM of each probe 0.25 µM of each Invader oligo 1.25 µM of FRET cassette 40 mM MOPS | 4 µl | 0.5 µM of each probe 0.05 µM of each Invader oligo 0.25 µM FRET cassette 10 mM MOPS |
| Alpha Actin Primary probe/ INVADER oligo/RED FRET/MOPS Stock conc. 5 µM probe 1 µM Invader oligo 5 µM of FRET 40 mM MOPS | 1 µl | 0.25 µM probe 0.05 µM Invader oligo 0.25 µM FRET cassette 10 mM MOPS |

-continued

| Component | Amount per reaction | Final concentrations (in 20 µl reaction) |
|---|---|---|
| CLEAVASE X enzyme (40 ng/µl) in CLEAVASE dilution buffer | 1 µl | 2 ng/µl |

INVADER Assay Reactions

Reactions were incubated at 63° C. for 4 hours and then cooled to 4° C. prior to scanning in a CYTOFLUOR 4000 fluorescence plate reader (Applied Biosystems, Foster City, Calif.). The settings used were: 485/20 nm excitation/bandwidth and 530/25 nm emission/bandwidth for FAM dye detection, and 560/20 nm excitation/bandwidth and 620/40 nm emission/bandwidth for RED dye detection. The instrument gain was set for each dye so that the No Target Blank produced between 100-250 Relative Fluorescence Units (RFUs). Microplates were also read in the Genios FL Plate reader (Tecan, Research Triangle Park, N.C.). The settings used were: 485/535 nm excitation/emission for FAM dye detection, and 560/612 nm excitation/emission for RED dye detection. The instrument gain was set for each dye so that the No Target Blank produced between 1000-2000 Relative Fluorescence Units (RFUs). Because the optimal gain setting can vary between instruments, the gain was adjusted to provide the best signal/background ratio (e.g., sample raw signal divided by the No Target Control signal) or No Target Control sample readings. For directly reading the microplates, the probe height of the microplate reader and the positioning of the plate was adjusted according to the manufacturer's recommendations.

The fluorescent signal from the Fam dye and the Red dye for the samples and No Target Control (NTC) was used to calculate fold over zero (FOZ) values as shown below.

$$FOZ_{Fam}dye=(RawSignal_{Fam}/NTC_{Fam})$$

$$FOZ_{Red}=(RawSignal_{Red}/NTC_{Red})$$

Figure 9:
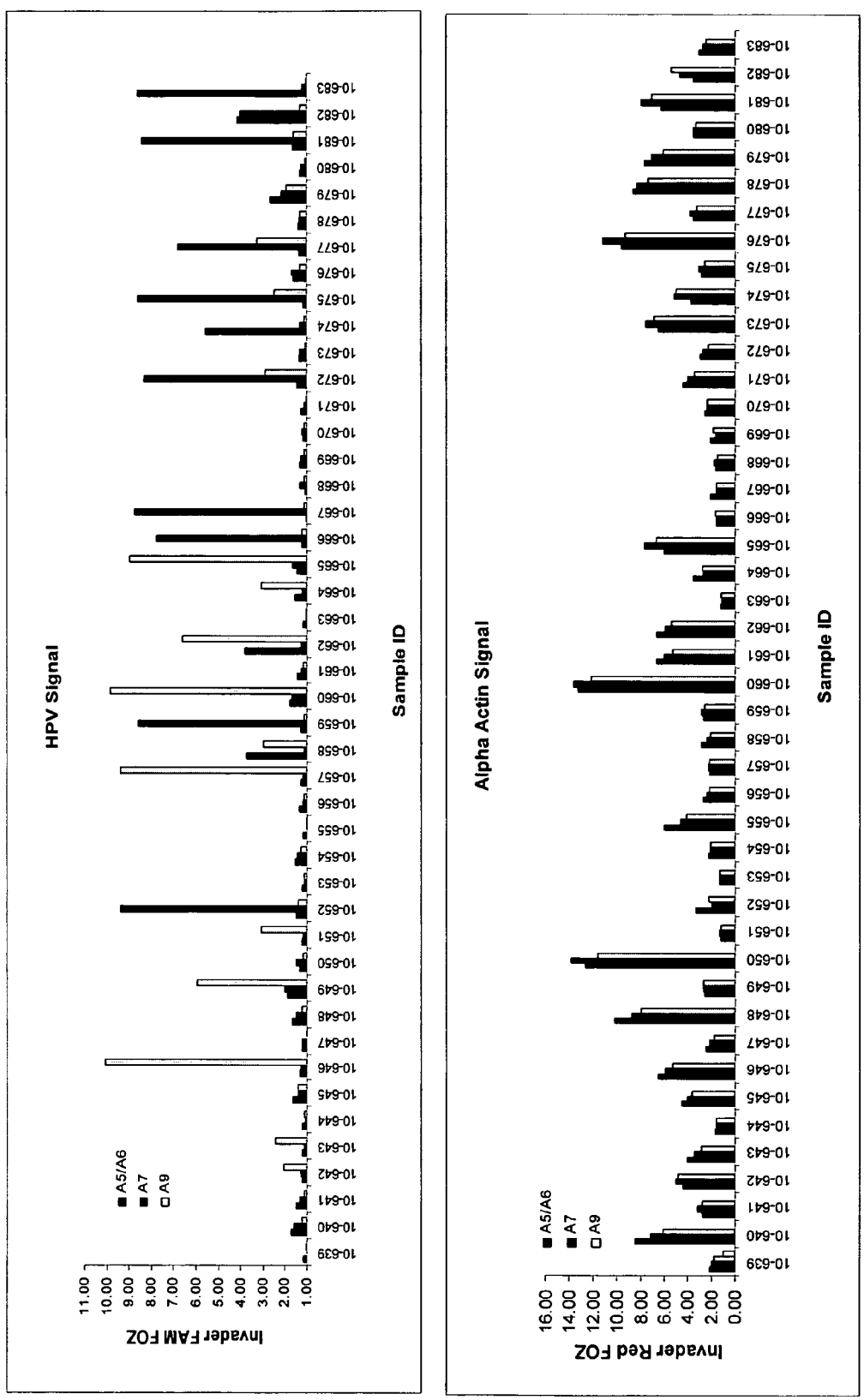
FIG. 9 shows detection of HPV and Alpha-Actin in cervical samples conducted in some embodiments of the present invention.

The Fam FOZ corresponds to the signal from the HPV assays, and the RED FOZ corresponds to the alpha-actin signal (See, e.g., FIG. 9).

Results of INVADER Assays for Detection HPV in Cervical Specimens

Figure 8:
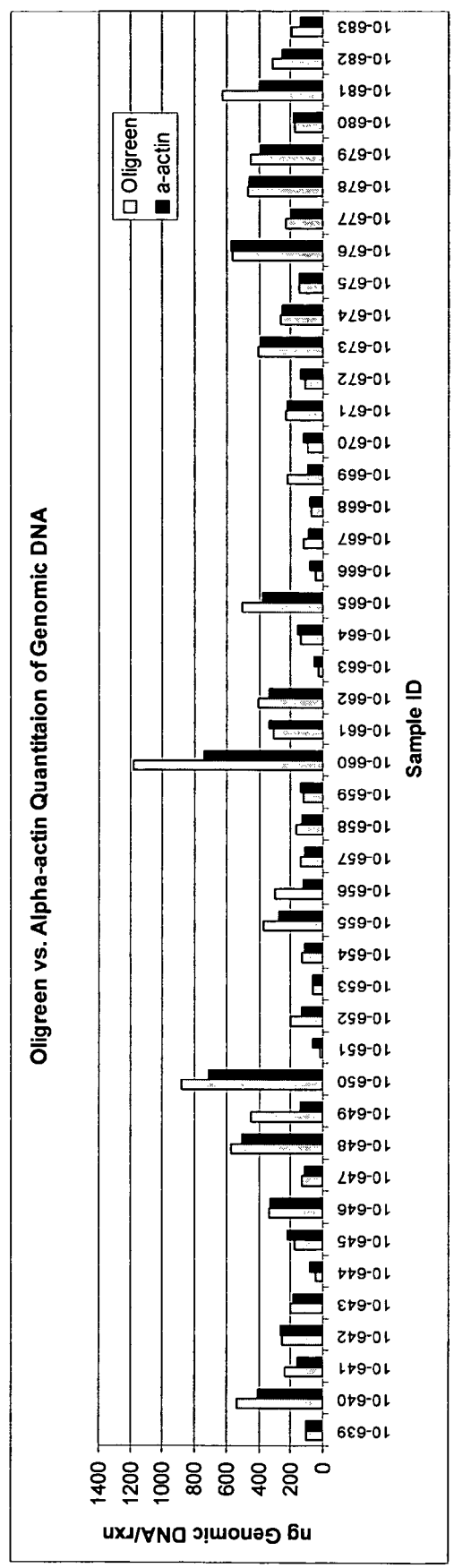
FIG. 8 shows the quantitation of cervical sample genomic DNA using the Oligreen Quantitation Kit or the Alpha-Actin Invader assays.

Quantification of DNA concentration in cervical samples may be achieved using various methods. For example, DNA concentration can be measured using the OliGreen ssDNA Quantitation kit (Molecular probes) or the alpha-actin INVADER assay (See, e.g., FIG. 8). To determine the amount of DNA present in each sample using the INVADER Assay, a control genomic DNA sample was serially diluted to generate a standard curve. The alpha-actin INVADER assay standard curve was used to determine the amount of DNA present in each sample using a linear regression analysis. Both methods are useful for determining concentrations of DNA in cervical samples. Since the signal from the alpha-actin INVADER assay can be detected in the same well as the HPV INVADER assays, a separate quantitation step by OliGreen or measuring absorbance at 260 nm is not required.

The INVADER assay was used to detect the presence or absence of HPV (e.g., high-risk HPV strains) in cervical samples (See, e.g., FIG. 9). Each sample was tested in three separate wells of a microtiter plate containing either the A5/A6, A7 or A9 INVADER reaction mix. All wells contained the alpha-actin oligonucleotides and FRET cassette. Samples were considered to be HPV positive if the FAM FOZ values were greater than 3, HPV negative if the FAM FOZ values were less than 2, and equivocal if the FAM FOZ values were between 2 and 3. Of the 45 cervical samples tested, there were 21 positive samples, 23 negative samples, and 1 equivocal sample. Four of the samples were determined, using the methods of the present invention, to be co-infected with multiple HPV strains (See, e.g., FIG. 9, samples 10-658, 10-662, 10-677 and 10-682).

All publications and patents mentioned in the above specification are herein incorporated by reference as if expressly set forth herein. Various modifications and variations of the described assays of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

We claim:

1. A kit comprising oligonucleotide detection assay components for detecting HPV sequences, wherein said components consist of:

a) first, second and third pools of oligonucleotide sets, said sets consisting of first and second oligonucleotides, wherein the combination of first and second oligonucleotides form an invasive cleavage structure in combination with a target sequence comprising a HPV sequence, wherein said first pool comprises a first oligonucleotide of SEQ ID NO. 77 and a second oligonucleotide of SEQ ID NO. 78; said second pool comprises a first oligonucleotide of SEQ ID NO. 127 and a second oligonucleotide of SEQ ID NO. 129; and wherein said third pool comprises a first oligonucleotide of SEQ ID NO. 160 and a second oligonucleotide of SEQ ID NO. 161;
b) a FEN-1 endonuclease;
c) an internal control;
d) a plurality of fluorescence resonance energy transfer (FRET) cassettes; and
e) assay reagents comprising a buffer solution.

2. The kit of claim 1, wherein said first pool of oligonucleotides further comprise SEQ ID NO. 79 and SEQ ID NO. 80.

3. The kit of claim 1, wherein said second pool of oligonucleotides further comprise SEQ ID NO. 91, SEQ ID NO. 94, SEQ ID NO. 142, SEQ ID NO. 90, and SEQ ID NO. 95.

4. The kit of claim 1, wherein said third pool of oligonucleotides further comprise SEQ ID NO. 110, SEQ ID NO. 163, SEQ ID NO. 173, SEQ ID NO. 177, SEQ ID NO. 180, SEQ ID NO. 111, SEQ ID NO. 112, SEQ ID NO. 113, SEQ ID NO. 164, SEQ ID NO. 165, SEQ ID NO. 166 and SEQ ID NO. 175.

5. The kit of claim 1, wherein each of said first and second oligonucleotides comprise at least a one base pair mismatch with said target sequence.

6. The kit of claim 1, wherein said first and second oligonucleotides of each pool form invasive cleavage structures under the same reaction conditions.

7. The kit of claim 1, wherein oligonucleotides of said first pool participate in a detectable invasive cleavage structure in the presence of a target sequence comprising HPV type 51 sequence and/or HPV type 56 sequence and no other high risk HPV sequence.

8. The kit of claim 1, wherein oligonucleotides of said second pool participate in a detectable invasive cleavage structure in the presence of a target sequence comprising HPV type 18 sequence, HPV type 39 sequence, HPV type 45 sequence, HPV type 59 sequence, HPV type 68 sequence and/or HPV type 70 sequence and no other high risk HPV sequence.

9. The kit of claim 1, wherein oliognucleotides of said third pool participate in a detectable invasive cleavage structure in the presence of a target sequence comprising HPV type 16 sequence, HPV type 31 sequence, HPV type 33 sequence, HPV type 35 sequence, HPV type 52 sequence, HPV type 58 and/or HPV type 67 sequence and no other high risk HPV sequence.

10. The kit of claim 1, wherein said oligonucleotide detection assay components detect two or more HPV types simultaneously in the presence or absence of other, non-detected HPV types.

* * * * *

SEQUENCE LISTING

<160> NUMBER OF SEQ ID NOS: 193

<210> SEQ ID NO 1
<211> LENGTH: 28
<212> TYPE: DNA
<213> ORGANISM: Artificial Sequence
<220> FEATURE:
<223> OTHER INFORMATION: Synthetic

<400> SEQUENCE: 1
cgcgccgagg gtccggttct gcttgacc                                      28

<210> SEQ ID NO 2
<211> LENGTH: 43
<212> TYPE: DNA
<213> ORGANISM: Artificial Sequence
<220> FEATURE:
<223> OTHER INFORMATION: Synthetic

<400> SEQUENCE: 2
cttacactgg caacaaaagg ttacgatatt gtaatgggat ctc                           43

<210> SEQ ID NO 3
<211> LENGTH: 48
<212> TYPE: DNA
<213> ORGANISM: Artificial Sequence
<220> FEATURE:
<223> OTHER INFORMATION: Synthetic

<400> SEQUENCE: 3
gtagactcac actgccaaca aaaggttacg atattgtaat tggatgtc                      48

<210> SEQ ID NO 4
<211> LENGTH: 35
<212> TYPE: DNA
<213> ORGANISM: Artificial Sequence
<220> FEATURE:
<223> OTHER INFORMATION: Synthetic

<400> SEQUENCE: 4
ggcagtctgg gagtcaacac aaacagggac cacaa                                    35

<210> SEQ ID NO 5
<211> LENGTH: 54
<212> TYPE: DNA
<213> ORGANISM: Artificial Sequence
<220> FEATURE:
<223> OTHER INFORMATION: Synthetic

<400> SEQUENCE: 5
gctccaacgg gtttcctgcg cacaatatta aacacacatt tacacgccat gtat               54

<210> SEQ ID NO 6
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: The residue at this position is linked to a
      Z28 quencher.

<400> SEQUENCE: 6
tctagccggt tttccggctg agaactccca gactgcc                                  37

<210> SEQ ID NO 7
<211> LENGTH: 36
<212> TYPE: DNA
<213> ORGANISM: Artificial Sequence
<220> FEATURE:
<223> OTHER INFORMATION: Synthetic

<400> SEQUENCE: 7
ggcagtctgg gagtgttgta tgactatgga gcaccg                                   36

<210> SEQ ID NO 8
<211> LENGTH: 62
<212> TYPE: DNA
<213> ORGANISM: Artificial Sequence
<220> FEATURE:
<223> OTHER INFORMATION: Synthetic

<400> SEQUENCE: 8

```
gctccaacgg gtttcctgct agccataatg tgatgtgtgt gtttataatt aacactgtat    60
tt                                                                  62

<210> SEQ ID NO 9
<211> LENGTH: 37
<212> TYPE: DNA
<213> ORGANISM: Artificial Sequence
<220> FEATURE:
<223> OTHER INFORMATION: Synthetic

<400> SEQUENCE: 9
ggcagtctgg gagtgaagtg gacagacttt gtaaggt                            37

<210> SEQ ID NO 10
<211> LENGTH: 55
<212> TYPE: DNA
<213> ORGANISM: Artificial Sequence
<220> FEATURE:
<223> OTHER INFORMATION: Synthetic

<400> SEQUENCE: 10
agatggcgac accaatccgg gcacaatatt aaacacacat ttacacgcca tgtat        55

<210> SEQ ID NO 11
<211> LENGTH: 28
<212> TYPE: DNA
<213> ORGANISM: Artificial Sequence
<220> FEATURE:
<223> OTHER INFORMATION: Synthetic

<400> SEQUENCE: 11
cgcgccgagg tcaagggttt ctggcacc                                      28

<210> SEQ ID NO 12
<211> LENGTH: 40
<212> TYPE: DNA
<213> ORGANISM: Artificial Sequence
<220> FEATURE:
<223> OTHER INFORMATION: Synthetic

<400> SEQUENCE: 12
gtcgtttttc cttaaggtgt ctaagttttt ctgctgggta                         40

<210> SEQ ID NO 13
<211> LENGTH: 40
<212> TYPE: DNA
<213> ORGANISM: Artificial Sequence
<220> FEATURE:
<223> OTHER INFORMATION: Synthetic

<400> SEQUENCE: 13
gtcgtttgtc attaaggtgt ctaagttttt ctgctggata                         40

<210> SEQ ID NO 14
<211> LENGTH: 30
<212> TYPE: DNA
<213> ORGANISM: Artificial Sequence
<220> FEATURE:
<223> OTHER INFORMATION: Synthetic

<400> SEQUENCE: 14
cgcgccgagg gtcctttgtg tgaccgtggt                                    30

<210> SEQ ID NO 15
```

```
<211> LENGTH: 39
<212> TYPE: DNA
<213> ORGANISM: Artificial Sequence
<220> FEATURE:
<223> OTHER INFORMATION: Synthetic

<400> SEQUENCE: 15
ggattgcgag cattacagca gctgtttctg gamaccctc                    39

<210> SEQ ID NO 16
<211> LENGTH: 39
<212> TYPE: DNA
<213> ORGANISM: Artificial Sequence
<220> FEATURE:
<223> OTHER INFORMATION: Synthetic

<400> SEQUENCE: 16
gaccttcgag cactccagca gctgttttg agcaccttc                     39

<210> SEQ ID NO 17
<211> LENGTH: 28
<212> TYPE: DNA
<213> ORGANISM: Artificial Sequence
<220> FEATURE:
<223> OTHER INFORMATION: Synthetic

<400> SEQUENCE: 17
cgcgccgagg agggcaatag ggtcgcca                                28

<210> SEQ ID NO 18
<211> LENGTH: 35
<212> TYPE: DNA
<213> ORGANISM: Artificial Sequence
<220> FEATURE:
<223> OTHER INFORMATION: Synthetic

<400> SEQUENCE: 18
acaaatataa actgttgtgc tgcaaaaaat gggtt                        35

<210> SEQ ID NO 19
<211> LENGTH: 30
<212> TYPE: DNA
<213> ORGANISM: Artificial Sequence
<220> FEATURE:
<223> OTHER INFORMATION: Synthetic

<400> SEQUENCE: 19
caagtgtgct gcaagccaca aatatgggtt                              30

<210> SEQ ID NO 20
<211> LENGTH: 28
<212> TYPE: DNA
<213> ORGANISM: Artificial Sequence
<220> FEATURE:
<223> OTHER INFORMATION: Synthetic

<400> SEQUENCE: 20
cgcgccgagg gtccatctgg ccagtcca                                28

<210> SEQ ID NO 21
<211> LENGTH: 54
<212> TYPE: DNA
<213> ORGANISM: Artificial Sequence
<220> FEATURE:
<223> OTHER INFORMATION: Synthetic

<400> SEQUENCE: 21
```

```
cccaaatata atcacaatgc tgatgtagta attgcttatg gcttgttctg cttc        54
```

<210> SEQ ID NO 22
<211> LENGTH: 30
<212> TYPE: DNA
<213> ORGANISM: Artificial Sequence
<220> FEATURE:
<223> OTHER INFORMATION: Synthetic

<400> SEQUENCE: 22

```
gtagtaatca gctgtggccg gttgtgcttc                                   30
```

<210> SEQ ID NO 23
<211> LENGTH: 34
<212> TYPE: DNA
<213> ORGANISM: Artificial Sequence
<220> FEATURE:
<223> OTHER INFORMATION: Synthetic

<400> SEQUENCE: 23

```
cgcgccgagg gaccttgtat gtcacgtgca atta                              34
```

<210> SEQ ID NO 24
<211> LENGTH: 51
<212> TYPE: DNA
<213> ORGANISM: Artificial Sequence
<220> FEATURE:
<223> OTHER INFORMATION: Synthetic

<400> SEQUENCE: 24

```
tgcaagaaat tgtgttagat ttatatccat gcaatgaaat agagccggtc a           51
```

<210> SEQ ID NO 25
<211> LENGTH: 48
<212> TYPE: DNA
<213> ORGANISM: Artificial Sequence
<220> FEATURE:
<223> OTHER INFORMATION: Synthetic

<400> SEQUENCE: 25

```
aggaaattgt attagagtta tgtccttaca atgaaataca gccggttc               48
```

<210> SEQ ID NO 26
<211> LENGTH: 28
<212> TYPE: DNA
<213> ORGANISM: Artificial Sequence
<220> FEATURE:
<223> OTHER INFORMATION: Synthetic

<400> SEQUENCE: 26

```
cgcgccgagg gtgcacctgg agaggatg                                     28
```

<210> SEQ ID NO 27
<211> LENGTH: 38
<212> TYPE: DNA
<213> ORGANISM: Artificial Sequence
<220> FEATURE:
<223> OTHER INFORMATION: Synthetic

<400> SEQUENCE: 27

```
agggtggaga tatgtatgct gccaaagtat tgttgcaa                          38
```

<210> SEQ ID NO 28
<211> LENGTH: 38
<212> TYPE: DNA

```
<213> ORGANISM: Artificial Sequence
<220> FEATURE:
<223> OTHER INFORMATION: Synthetic

<400> SEQUENCE: 28
agggtggaga tatagatgtt gccaaactat tgttgcaa                                    38

<210> SEQ ID NO 29
<211> LENGTH: 65
<212> TYPE: DNA
<213> ORGANISM: Artificial Sequence
<220> FEATURE:
<223> OTHER INFORMATION: Synthetic

<400> SEQUENCE: 29
cctatgccta aaagctgttt tattacaagg gtggcgccac caaagttgtg caagtattgt            60
tagaa                                                                       65

<210> SEQ ID NO 30
<211> LENGTH: 32
<212> TYPE: DNA
<213> ORGANISM: Artificial Sequence
<220> FEATURE:
<223> OTHER INFORMATION: Synthetic

<400> SEQUENCE: 30
cgcgccgagg atgagcaatt acgtgacagc tc                                          32

<210> SEQ ID NO 31
<211> LENGTH: 59
<212> TYPE: DNA
<213> ORGANISM: Artificial Sequence
<220> FEATURE:
<223> OTHER INFORMATION: Synthetic

<400> SEQUENCE: 31
cagccaagcg caggcgttgt tttagattta tatcctgtac caactgacct atactgctt            59

<210> SEQ ID NO 32
<211> LENGTH: 53
<212> TYPE: DNA
<213> ORGANISM: Artificial Sequence
<220> FEATURE:
<223> OTHER INFORMATION: Synthetic

<400> SEQUENCE: 32
cagccaagcg caggcgtaga tttacatcct gtaccaactg acctattctg ctt                  53

<210> SEQ ID NO 33
<211> LENGTH: 57
<212> TYPE: DNA
<213> ORGANISM: Artificial Sequence
<220> FEATURE:
<223> OTHER INFORMATION: Synthetic

<400> SEQUENCE: 33
cagccaagcg caggcgtatt ttagatttac atcctgtacc aattgaccta ttctgct             57

<210> SEQ ID NO 34
<211> LENGTH: 48
<212> TYPE: DNA
<213> ORGANISM: Artificial Sequence
<220> FEATURE:
<223> OTHER INFORMATION: Synthetic

<400> SEQUENCE: 34
```
cagccaagcg caggcgttgc aacctgtaac aactgaccta cactgctt        48

<210> SEQ ID NO 35
<211> LENGTH: 53
<212> TYPE: DNA
<213> ORGANISM: Artificial Sequence
<220> FEATURE:
<223> OTHER INFORMATION: Synthetic

<400> SEQUENCE: 35
cagccaagcg caggcgtaga tttgcaacca gtgacaactg atctctactg ttt        53

<210> SEQ ID NO 36
<211> LENGTH: 27
<212> TYPE: DNA
<213> ORGANISM: Artificial Sequence
<220> FEATURE:
<223> OTHER INFORMATION: Synthetic

<400> SEQUENCE: 36
cgcgccgagg gagcggaacc acagcgt        27

<210> SEQ ID NO 37
<211> LENGTH: 46
<212> TYPE: DNA
<213> ORGANISM: Artificial Sequence
<220> FEATURE:
<223> OTHER INFORMATION: Synthetic

<400> SEQUENCE: 37
gggccataaa taataattat cctcatgcac aactaccggc ccgacc        46

<210> SEQ ID NO 38
<211> LENGTH: 56
<212> TYPE: DNA
<213> ORGANISM: Artificial Sequence
<220> FEATURE:
<223> OTHER INFORMATION: Synthetic

<400> SEQUENCE: 38
gaggaagaaa acgatgaact agatggagtt aatcatcatt tgctactagc tagacc        56

<210> SEQ ID NO 39
<211> LENGTH: 27
<212> TYPE: DNA
<213> ORGANISM: Artificial Sequence
<220> FEATURE:
<223> OTHER INFORMATION: Synthetic

<400> SEQUENCE: 39
cgcgccgagg gatcctcaaa gcgagcc        27

<210> SEQ ID NO 40
<211> LENGTH: 43
<212> TYPE: DNA
<213> ORGANISM: Artificial Sequence
<220> FEATURE:
<223> OTHER INFORMATION: Synthetic

<400> SEQUENCE: 40
attctgtgca caaatcaggt agcttgtagg gtcgtcgtgt tgc        43

<210> SEQ ID NO 41
<211> LENGTH: 37
<212> TYPE: DNA

```
<213> ORGANISM: Artificial Sequence
<220> FEATURE:
<223> OTHER INFORMATION: Synthetic

<400> SEQUENCE: 41
tgcacaaatc aggcagtttg taaggtcgtt gtgtagc                              37

<210> SEQ ID NO 42
<211> LENGTH: 66
<212> TYPE: DNA
<213> ORGANISM: Artificial Sequence
<220> FEATURE:
<223> OTHER INFORMATION: Synthetic

<400> SEQUENCE: 42
gcatggcacg ctttgaggat cctacacaac gaccatacaa actgcctgat ttgagcacaa    60
cattga                                                                66

<210> SEQ ID NO 43
<211> LENGTH: 26
<212> TYPE: DNA
<213> ORGANISM: Artificial Sequence
<220> FEATURE:
<223> OTHER INFORMATION: Synthetic

<400> SEQUENCE: 43
cgcgccgagg gcccactctg cgcttc                                          26

<210> SEQ ID NO 44
<211> LENGTH: 29
<212> TYPE: DNA
<213> ORGANISM: Artificial Sequence
<220> FEATURE:
<223> OTHER INFORMATION: Synthetic

<400> SEQUENCE: 44
cgcgccgagg gtaacttgcc cactctgcg                                       29

<210> SEQ ID NO 45
<211> LENGTH: 28
<212> TYPE: DNA
<213> ORGANISM: Artificial Sequence
<220> FEATURE:
<223> OTHER INFORMATION: Synthetic

<400> SEQUENCE: 45
cgcgccgagg gtaacgtgcc ctctctgc                                        28

<210> SEQ ID NO 46
<211> LENGTH: 28
<212> TYPE: DNA
<213> ORGANISM: Artificial Sequence
<220> FEATURE:
<223> OTHER INFORMATION: Synthetic

<400> SEQUENCE: 46
cgcgccgagg gtaacgtgcc ccctctgc                                        28

<210> SEQ ID NO 47
<211> LENGTH: 35
<212> TYPE: DNA
<213> ORGANISM: Artificial Sequence
<220> FEATURE:
<223> OTHER INFORMATION: Synthetic

<400> SEQUENCE: 47
```

```
caactgctgc ttatgggtgc gttaacagta acgtc                          35

<210> SEQ ID NO 48
<211> LENGTH: 31
<212> TYPE: DNA
<213> ORGANISM: Artificial Sequence
<220> FEATURE:
<223> OTHER INFORMATION: Synthetic

<400> SEQUENCE: 48
gtactacagc tgcttatggg tgcgttaaca c                              31

<210> SEQ ID NO 49
<211> LENGTH: 35
<212> TYPE: DNA
<213> ORGANISM: Artificial Sequence
<220> FEATURE:
<223> OTHER INFORMATION: Synthetic

<400> SEQUENCE: 49
ggcagtctgg gagtgtacag cagaagttaa tgggc                          35

<210> SEQ ID NO 50
<211> LENGTH: 43
<212> TYPE: DNA
<213> ORGANISM: Artificial Sequence
<220> FEATURE:
<223> OTHER INFORMATION: Synthetic

<400> SEQUENCE: 50
gctccaacgg gtttcctgcg cagtggagac tcccttcgcg ttc                 43

<210> SEQ ID NO 51
<211> LENGTH: 35
<212> TYPE: DNA
<213> ORGANISM: Artificial Sequence
<220> FEATURE:
<223> OTHER INFORMATION: Synthetic

<400> SEQUENCE: 51
ggcagtctgg gagtgtacag cagatgttta tgggc                          35

<210> SEQ ID NO 52
<211> LENGTH: 44
<212> TYPE: DNA
<213> ORGANISM: Artificial Sequence
<220> FEATURE:
<223> OTHER INFORMATION: Synthetic

<400> SEQUENCE: 52
agatggcgac accaatccgg gcagaggaga caccccttcgc gttc               44

<210> SEQ ID NO 53
<211> LENGTH: 35
<212> TYPE: DNA
<213> ORGANISM: Artificial Sequence
<220> FEATURE:
<223> OTHER INFORMATION: Synthetic

<400> SEQUENCE: 53
ggcagtctgg gagtgtccat accgatcgcg cgatt                          35

<210> SEQ ID NO 54
<211> LENGTH: 50
<212> TYPE: DNA
```

<210> SEQ ID NO 55
<211> LENGTH: 37
<212> TYPE: DNA
<213> ORGANISM: Artificial Sequence
<220> FEATURE:
<223> OTHER INFORMATION: Synthetic

<400> SEQUENCE: 54
aaacggtttc aaccgaaatc ggtggatata aaaggcagtc acagtttctc    50

<210> SEQ ID NO 55
<211> LENGTH: 37
<212> TYPE: DNA
<213> ORGANISM: Artificial Sequence
<220> FEATURE:
<223> OTHER INFORMATION: Synthetic

<400> SEQUENCE: 55
ggcagtctgg gagtgcaaca tccatttctc caccta    37

<210> SEQ ID NO 56
<211> LENGTH: 43
<212> TYPE: DNA
<213> ORGANISM: Artificial Sequence
<220> FEATURE:
<223> OTHER INFORMATION: Synthetic

<400> SEQUENCE: 56
cttactcatc atcctgtcca ggtgcactac aacaatactt tgc    43

<210> SEQ ID NO 57
<211> LENGTH: 33
<212> TYPE: DNA
<213> ORGANISM: Artificial Sequence
<220> FEATURE:
<223> OTHER INFORMATION: Synthetic

<400> SEQUENCE: 57
ggcagtctgg gagtaggtag ggcacacata cca    33

<210> SEQ ID NO 58
<211> LENGTH: 58
<212> TYPE: DNA
<213> ORGANISM: Artificial Sequence
<220> FEATURE:
<223> OTHER INFORMATION: Synthetic

<400> SEQUENCE: 58
cgtcagccaa gcgcaggcgt gactaatacc acatccatta atttgtgcaa ccgaaatc    58

<210> SEQ ID NO 59
<211> LENGTH: 35
<212> TYPE: DNA
<213> ORGANISM: Artificial Sequence
<220> FEATURE:
<223> OTHER INFORMATION: Synthetic

<400> SEQUENCE: 59
ggcagtctgg gagtagaagg caactagaac ggaca    35

<210> SEQ ID NO 60
<211> LENGTH: 45
<212> TYPE: DNA
<213> ORGANISM: Artificial Sequence
<220> FEATURE:
<223> OTHER INFORMATION: Synthetic

<400> SEQUENCE: 60
tggacaccac cttgcatgac tttacaatag actgtgtcta ttgcc    45

<210> SEQ ID NO 61
<211> LENGTH: 35
<212> TYPE: DNA
<213> ORGANISM: Artificial Sequence
<220> FEATURE:
<223> OTHER INFORMATION: Synthetic

<400> SEQUENCE: 61
ggcagtctgg gagtgcagct tattctgagt ggact          35

<210> SEQ ID NO 62
<211> LENGTH: 41
<212> TYPE: DNA
<213> ORGANISM: Artificial Sequence
<220> FEATURE:
<223> OTHER INFORMATION: Synthetic

<400> SEQUENCE: 62
accgaaacgg gtttatgacc gaaaacggta catataaaag c          41

<210> SEQ ID NO 63
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: The residue at this position is linked to a
      Z28 quencher.

<400> SEQUENCE: 63
tctagccggt tttccggctg agacctcggc gcg          33

<210> SEQ ID NO 64
<211> LENGTH: 27
<212> TYPE: DNA
<213> ORGANISM: Artificial Sequence
<220> FEATURE:
<223> OTHER INFORMATION: Synthetic

<400> SEQUENCE: 64
tccgcgcgtc caggaaccct gtgacat          27

<210> SEQ ID NO 65
<211> LENGTH: 25
<212> TYPE: DNA
<213> ORGANISM: Artificial Sequence
<220> FEATURE:
<223> OTHER INFORMATION: Synthetic

<400> SEQUENCE: 65
ccatccaggg aagagtggcc tgttt          25

<210> SEQ ID NO 66
<211> LENGTH: 30
<212> TYPE: DNA
<213> ORGANISM: Artificial Sequence
<220> FEATURE:
<223> OTHER INFORMATION: Synthetic

<400> SEQUENCE: 66
tccgcgcgtc ctgaagaagc accaatcatg          30

<210> SEQ ID NO 67
<211> LENGTH: 44
<212> TYPE: DNA
<213> ORGANISM: Artificial Sequence
<220> FEATURE:
<223> OTHER INFORMATION: Synthetic

<400> SEQUENCE: 67
tgtacttcat gctgtctaca ctaagagaga atgagagaca caca         44

<210> SEQ ID NO 68
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: The residue at this position is linked to a
      Z28 quencher.

<400> SEQUENCE: 68
tcttcggcct tttggccgag agaggacgcg cgga         34

<210> SEQ ID NO 69
<211> LENGTH: 26
<212> TYPE: DNA
<213> ORGANISM: Artificial Sequence
<220> FEATURE:
<223> OTHER INFORMATION: Synthetic

<400> SEQUENCE: 69
cgcgccgagg cagcactcat ccacga         26

<210> SEQ ID NO 70
<211> LENGTH: 30
<212> TYPE: DNA
<213> ORGANISM: Artificial Sequence
<220> FEATURE:
<223> OTHER INFORMATION: Synthetic

<400> SEQUENCE: 70
ccagcctcct tagatcacag ctccggaagt         30

<210> SEQ ID NO 71
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: The residue at this position is linked to a
      Z28 quencher.

<400> SEQUENCE: 71
tcttcggcct tttggccgag agagtctgcc acgtcat         37

<210> SEQ ID NO 72
<211> LENGTH: 73
<212> TYPE: DNA
<213> ORGANISM: Artificial Sequence
<220> FEATURE:
<223> OTHER INFORMATION: Synthetic

<400> SEQUENCE: 72

```
ttcggttgca cagcaaaatg gaggattgta ggataaaatg gatgctgtaa ggtgtgcagt    60
tttataactt gat                                                       73
```

<210> SEQ ID NO 73
<211> LENGTH: 40
<212> TYPE: DNA
<213> ORGANISM: Artificial Sequence
<220> FEATURE:
<223> OTHER INFORMATION: Synthetic

<400> SEQUENCE: 73

```
tctgcacacc ttacagcatc cattttctcc tacaatccta                          40
```

<210> SEQ ID NO 74
<211> LENGTH: 51
<212> TYPE: DNA
<213> ORGANISM: Artificial Sequence
<220> FEATURE:
<223> OTHER INFORMATION: Synthetic

<400> SEQUENCE: 74

```
acaagttata aacttgcata ctacacagca tccattttcc ttataatcct a             51
```

<210> SEQ ID NO 75
<211> LENGTH: 45
<212> TYPE: DNA
<213> ORGANISM: Artificial Sequence
<220> FEATURE:
<223> OTHER INFORMATION: Synthetic

<400> SEQUENCE: 75

```
agcatttgca cattatatgg cgtccatttt ctcctttaaa tccta                    45
```

<210> SEQ ID NO 76
<211> LENGTH: 29
<212> TYPE: DNA
<213> ORGANISM: Artificial Sequence
<220> FEATURE:
<223> OTHER INFORMATION: Synthetic

<400> SEQUENCE: 76

```
cgcgccgagg ccattttgca gtgcaaccg                                      29
```

<210> SEQ ID NO 77
<211> LENGTH: 35
<212> TYPE: DNA
<213> ORGANISM: Artificial Sequence
<220> FEATURE:
<223> OTHER INFORMATION: Synthetic

<400> SEQUENCE: 77

```
ggcagtctgg gagtgtacag cagatgttta tgggc                               35
```

<210> SEQ ID NO 78
<211> LENGTH: 44
<212> TYPE: DNA
<213> ORGANISM: Artificial Sequence
<220> FEATURE:
<223> OTHER INFORMATION: Synthetic

<400> SEQUENCE: 78

```
agatggcgac accaatccgg gcagaggaga cacccttcgc gttc                     44
```

<210> SEQ ID NO 79
<211> LENGTH: 32

<212> TYPE: DNA
<213> ORGANISM: Artificial Sequence
<220> FEATURE:
<223> OTHER INFORMATION: Synthetic

<400> SEQUENCE: 79
ggcagtctgg gagtgcttag cctgtggaag gg                          32

<210> SEQ ID NO 80
<211> LENGTH: 50
<212> TYPE: DNA
<213> ORGANISM: Artificial Sequence
<220> FEATURE:
<223> OTHER INFORMATION: Synthetic

<400> SEQUENCE: 80 cgttcctttta gatctacatt ccaaaattta tatttggcca aaggatctgc      50

<210> SEQ ID NO 81
<211> LENGTH: 35
<212> TYPE: DNA
<213> ORGANISM: Artificial Sequence
<220> FEATURE:
<223> OTHER INFORMATION: Synthetic

<400> SEQUENCE: 81
ggcagtctgg gagtgcagct tattctgagt ggact                       35

<210> SEQ ID NO 82
<211> LENGTH: 41
<212> TYPE: DNA
<213> ORGANISM: Artificial Sequence
<220> FEATURE:
<223> OTHER INFORMATION: Synthetic

<400> SEQUENCE: 82
accgaaacgg gtttatgacc gaaaacggta catataaaag c                41

<210> SEQ ID NO 83
<211> LENGTH: 31
<212> TYPE: DNA
<213> ORGANISM: Artificial Sequence
<220> FEATURE:
<223> OTHER INFORMATION: Synthetic

<400> SEQUENCE: 83
ggcagtctgg gagtgttggt ggctgttacc g                           31

<210> SEQ ID NO 84
<211> LENGTH: 61
<212> TYPE: DNA
<213> ORGANISM: Artificial Sequence
<220> FEATURE:
<223> OTHER INFORMATION: Synthetic

<400> SEQUENCE: 84
gctccaacgg gtttcctgcc atcccacaat ttatatttag ctaatgggtc ctgtttttct    60
c                                                                   61

<210> SEQ ID NO 85
<211> LENGTH: 27
<212> TYPE: DNA
<213> ORGANISM: Artificial Sequence
<220> FEATURE:
<223> OTHER INFORMATION: Synthetic

<400> SEQUENCE: 85
cgcgccgagg gatcctcaaa gcgagcc                                27

<210> SEQ ID NO 86
<211> LENGTH: 43
<212> TYPE: DNA
<213> ORGANISM: Artificial Sequence
<220> FEATURE:
<223> OTHER INFORMATION: Synthetic

<400> SEQUENCE: 86
attctgtgca caaatcaggt agcttgtagg gtcgtcgtgt tgc              43

<210> SEQ ID NO 87
<211> LENGTH: 37
<212> TYPE: DNA
<213> ORGANISM: Artificial Sequence
<220> FEATURE:
<223> OTHER INFORMATION: Synthetic

<400> SEQUENCE: 87
tgcacaaatc aggcagtttg taaggtcgtt gtgtagc                     37

<210> SEQ ID NO 88
<211> LENGTH: 27
<212> TYPE: DNA
<213> ORGANISM: Artificial Sequence
<220> FEATURE:
<223> OTHER INFORMATION: Synthetic

<400> SEQUENCE: 88
cgcgccgagg gagcggaacc acagcgt                                27

<210> SEQ ID NO 89
<211> LENGTH: 46
<212> TYPE: DNA
<213> ORGANISM: Artificial Sequence
<220> FEATURE:
<223> OTHER INFORMATION: Synthetic

<400> SEQUENCE: 89
gggccataaa taataattat cctcatgcac aactaccggc ccgacc           46

<210> SEQ ID NO 90
<211> LENGTH: 56
<212> TYPE: DNA
<213> ORGANISM: Artificial Sequence
<220> FEATURE:
<223> OTHER INFORMATION: Synthetic

<400> SEQUENCE: 90
gaggaagaaa acgatgaact agatggagtt aatcatcatt tgctactagc tagacc   56

<210> SEQ ID NO 91
<211> LENGTH: 35
<212> TYPE: DNA
<213> ORGANISM: Artificial Sequence
<220> FEATURE:
<223> OTHER INFORMATION: Synthetic

<400> SEQUENCE: 91
cgcgccgagg gattggacaa aacgatatgt atcca                       35

<210> SEQ ID NO 92
<211> LENGTH: 34

```
<212> TYPE: DNA
<213> ORGANISM: Artificial Sequence
<220> FEATURE:
<223> OTHER INFORMATION: Synthetic

<400> SEQUENCE: 92
ggtgtagcat cctttgaca ggtaatagca acat                                  34

<210> SEQ ID NO 93
<211> LENGTH: 34
<212> TYPE: DNA
<213> ORGANISM: Artificial Sequence
<220> FEATURE:
<223> OTHER INFORMATION: Synthetic

<400> SEQUENCE: 93
ggtgtagtat cctttgaca ggtaacagca actt                                  34

<210> SEQ ID NO 94
<211> LENGTH: 31
<212> TYPE: DNA
<213> ORGANISM: Artificial Sequence
<220> FEATURE:
<223> OTHER INFORMATION: Synthetic

<400> SEQUENCE: 94
cgcgccgagg aggaagcttt acaggacagt g                                    31

<210> SEQ ID NO 95
<211> LENGTH: 69
<212> TYPE: DNA
<213> ORGANISM: Artificial Sequence
<220> FEATURE:
<223> OTHER INFORMATION: Synthetic

<400> SEQUENCE: 95
ctgaaaccgt tgagtccagc agaaaaatta aggcacctaa ctaccaaacg aagatttcat     60
aaaatagcc                                                             69

<210> SEQ ID NO 96
<211> LENGTH: 69
<212> TYPE: DNA
<213> ORGANISM: Artificial Sequence
<220> FEATURE:
<223> OTHER INFORMATION: Synthetic

<400> SEQUENCE: 96
ctgaaaccgt tgtgtccagc agaaaaatta agacacgtta ataccaaacg aagatttcat     60
caaatagcc                                                             69

<210> SEQ ID NO 97
<211> LENGTH: 30
<212> TYPE: DNA
<213> ORGANISM: Artificial Sequence
<220> FEATURE:
<223> OTHER INFORMATION: Synthetic

<400> SEQUENCE: 97
cgcgccgagg ggtccggcaa tttgtatggc                                      30

<210> SEQ ID NO 98
<211> LENGTH: 33
<212> TYPE: DNA
<213> ORGANISM: Artificial Sequence
<220> FEATURE:
```

```
<223> OTHER INFORMATION: Synthetic

<400> SEQUENCE: 98
gtcttgcaag gtagtgtcca gcgctgtgca cac                                    33

<210> SEQ ID NO 99
<211> LENGTH: 38
<212> TYPE: DNA
<213> ORGANISM: Artificial Sequence
<220> FEATURE:
<223> OTHER INFORMATION: Synthetic

<400> SEQUENCE: 99
gtaatgtcat gcaatgtggt gtccaacgtc gtgcacac                               38

<210> SEQ ID NO 100
<211> LENGTH: 34
<212> TYPE: DNA
<213> ORGANISM: Artificial Sequence
<220> FEATURE:
<223> OTHER INFORMATION: Synthetic

<400> SEQUENCE: 100
tgtcttgcaa ggtagtgtcc agcgtcgtgc acac                                   34

<210> SEQ ID NO 101
<211> LENGTH: 28
<212> TYPE: DNA
<213> ORGANISM: Artificial Sequence
<220> FEATURE:
<223> OTHER INFORMATION: Synthetic

<400> SEQUENCE: 101
cgcgccgagg gtccatctgg ccagtcca                                          28

<210> SEQ ID NO 102
<211> LENGTH: 54
<212> TYPE: DNA
<213> ORGANISM: Artificial Sequence
<220> FEATURE:
<223> OTHER INFORMATION: Synthetic

<400> SEQUENCE: 102
cccaaatata atcacaatgc tgatgtagta attgcttatg gcttgttctg cttc             54

<210> SEQ ID NO 103
<211> LENGTH: 31
<212> TYPE: DNA
<213> ORGANISM: Artificial Sequence
<220> FEATURE:
<223> OTHER INFORMATION: Synthetic

<400> SEQUENCE: 103
tgtagtaatt agctgtggca ggttgtgctt c                                      31

<210> SEQ ID NO 104
<211> LENGTH: 58
<212> TYPE: DNA
<213> ORGANISM: Artificial Sequence
<220> FEATURE:
<223> OTHER INFORMATION: Synthetic

<400> SEQUENCE: 104
gctccaacgg gtttcctgca gtaacaattt ggtaattggt tgtatctggt tttgcttc         58
```

```
<210> SEQ ID NO 105
<211> LENGTH: 29
<212> TYPE: DNA
<213> ORGANISM: Artificial Sequence
<220> FEATURE:
<223> OTHER INFORMATION: Synthetic

<400> SEQUENCE: 105
cgcgccgagg gcacgttgca gccaatatg                                29

<210> SEQ ID NO 106
<211> LENGTH: 46
<212> TYPE: DNA
<213> ORGANISM: Artificial Sequence
<220> FEATURE:
<223> OTHER INFORMATION: Synthetic

<400> SEQUENCE: 106
cagccaagcg caggcgccca acaaatagca ttattgtgtc cctgac             46

<210> SEQ ID NO 107
<211> LENGTH: 51
<212> TYPE: DNA
<213> ORGANISM: Artificial Sequence
<220> FEATURE:
<223> OTHER INFORMATION: Synthetic

<400> SEQUENCE: 107
cagccaagcg caggcggtta ctccaacaaa tagcattatt atggccttgt c        51

<210> SEQ ID NO 108
<211> LENGTH: 28
<212> TYPE: DNA
<213> ORGANISM: Artificial Sequence
<220> FEATURE:
<223> OTHER INFORMATION: Synthetic

<400> SEQUENCE: 108
cgcgccgagg gccacggtgt acctgcct                                 28

<210> SEQ ID NO 109
<211> LENGTH: 25
<212> TYPE: DNA
<213> ORGANISM: Artificial Sequence
<220> FEATURE:
<223> OTHER INFORMATION: Synthetic

<400> SEQUENCE: 109
atgtccgtga ggcggcctag tgagc                                    25

<210> SEQ ID NO 110
<211> LENGTH: 29
<212> TYPE: DNA
<213> ORGANISM: Artificial Sequence
<220> FEATURE:
<223> OTHER INFORMATION: Synthetic

<400> SEQUENCE: 110
cgcgccgagg ggttatgctt gtccagctg                                29

<210> SEQ ID NO 111
<211> LENGTH: 59
<212> TYPE: DNA
<213> ORGANISM: Artificial Sequence
<220> FEATURE:
<223> OTHER INFORMATION: Synthetic
```

<400> SEQUENCE: 111
cagccaagcg caggcgcatt ccaacagga cgttacaata ttataattgg aggtgtctc    59

<210> SEQ ID NO 112
<211> LENGTH: 57
<212> TYPE: DNA
<213> ORGANISM: Artificial Sequence
<220> FEATURE:
<223> OTHER INFORMATION: Synthetic

<400> SEQUENCE: 112
cagccaagcg caggcgctga caacaacagg taacgatatt gtaattggat gtgtccc    57

<210> SEQ ID NO 113
<211> LENGTH: 54
<212> TYPE: DNA
<213> ORGANISM: Artificial Sequence
<220> FEATURE:
<223> OTHER INFORMATION: Synthetic

<400> SEQUENCE: 113
cagccaagcg caggcggcaa cacaaggtta caatattgta atgggctctg tccc    54

<210> SEQ ID NO 114
<211> LENGTH: 33
<212> TYPE: DNA
<213> ORGANISM: Artificial Sequence
<220> FEATURE:
<223> OTHER INFORMATION: Synthetic

<400> SEQUENCE: 114
cgcgccgagg acataatcat ccgtgcttac aac    33

<210> SEQ ID NO 115
<211> LENGTH: 33
<212> TYPE: DNA
<213> ORGANISM: Artificial Sequence
<220> FEATURE:
<223> OTHER INFORMATION: Synthetic

<400> SEQUENCE: 115
tgcctgcatg ataatagatg tttgtgcgtg cat    33

<210> SEQ ID NO 116
<211> LENGTH: 42
<212> TYPE: DNA
<213> ORGANISM: Artificial Sequence
<220> FEATURE:
<223> OTHER INFORMATION: Synthetic

<400> SEQUENCE: 116
gcctagaact gcctgcgtga tagtatatgt ttgttcgtgt tt    42

<210> SEQ ID NO 117
<211> LENGTH: 28
<212> TYPE: DNA
<213> ORGANISM: Artificial Sequence
<220> FEATURE:
<223> OTHER INFORMATION: Synthetic

<400> SEQUENCE: 117
acggacgcgg agaggaaccc tgtgacat    28

<210> SEQ ID NO 118
<211> LENGTH: 25

```
<212> TYPE: DNA
<213> ORGANISM: Artificial Sequence
<220> FEATURE:
<223> OTHER INFORMATION: Synthetic

<400> SEQUENCE: 118
ccatccaggg aagagtggcc tgttt                                       25

<210> SEQ ID NO 119
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: The residue at this position is linked to a
      Z28 quencher.

<400> SEQUENCE: 119
tctagccggt tttccggctg agacctcggc gcg                              33

<210> SEQ ID NO 120
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: The residue at this position is linked to a
      Z28 quencher.

<400> SEQUENCE: 120
tctagccggt tttccggctg agaactccca gactgcc                          37

<210> SEQ ID NO 121
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: The residue at this position is linked to a
      Z28 quencher.

<400> SEQUENCE: 121
tcttcggcct tttggccgag agactccgcg tccgt                            35

<210> SEQ ID NO 122
<211> LENGTH: 32
<212> TYPE: DNA
<213> ORGANISM: Artificial Sequence
<220> FEATURE:
<223> OTHER INFORMATION: Synthetic

<400> SEQUENCE: 122
ggcagtctgg gagtgctgag gtttccccaa ca                               32

<210> SEQ ID NO 123
<211> LENGTH: 32
<212> TYPE: DNA
<213> ORGANISM: Artificial Sequence
<220> FEATURE:
<223> OTHER INFORMATION: Synthetic
```

<400> SEQUENCE: 123
ggcagtctgg gagtgctgca gtttccccaa ca                32

<210> SEQ ID NO 124
<211> LENGTH: 59
<212> TYPE: DNA
<213> ORGANISM: Artificial Sequence
<220> FEATURE:
<223> OTHER INFORMATION: Synthetic

<400> SEQUENCE: 124
gctccaacgg gtttcctgca ctaccagacg tacaaattta actattagca ctgccactc     59

<210> SEQ ID NO 125
<211> LENGTH: 32
<212> TYPE: DNA
<213> ORGANISM: Artificial Sequence
<220> FEATURE:
<223> OTHER INFORMATION: Synthetic

<400> SEQUENCE: 125
ggcagtctgg gagtggtagg agcagaccgc tt                32

<210> SEQ ID NO 126
<211> LENGTH: 48
<212> TYPE: DNA
<213> ORGANISM: Artificial Sequence
<220> FEATURE:
<223> OTHER INFORMATION: Synthetic

<400> SEQUENCE: 126
cagccaagcg caggcggcct cttacgtttt gctggtgtag aggtggac    48

<210> SEQ ID NO 127
<211> LENGTH: 30
<212> TYPE: DNA
<213> ORGANISM: Artificial Sequence
<220> FEATURE:
<223> OTHER INFORMATION: Synthetic

<400> SEQUENCE: 127
cgcgccgagg attcccctte ccccagtggc        30

<210> SEQ ID NO 128
<211> LENGTH: 62
<212> TYPE: DNA
<213> ORGANISM: Artificial Sequence
<220> FEATURE:
<223> OTHER INFORMATION: Synthetic

<400> SEQUENCE: 128
tccggtgcat tatacacaag tgtgcacacg gatatacttg agcgtcctgg tactcatgta    60
tc        62

<210> SEQ ID NO 129
<211> LENGTH: 60
<212> TYPE: DNA
<213> ORGANISM: Artificial Sequence
<220> FEATURE:
<223> OTHER INFORMATION: Synthetic

<400> SEQUENCE: 129
tccggtgcat tatacacaag tgtgcactaa tatgcttgaa acccctggca gttgtgtgtc    60

<210> SEQ ID NO 130
<211> LENGTH: 31
<212> TYPE: DNA
<213> ORGANISM: Artificial Sequence
<220> FEATURE:
<223> OTHER INFORMATION: Synthetic

<400> SEQUENCE: 130
cgcgccgagg attcccttc ccccagtggc t                                31

<210> SEQ ID NO 131
<211> LENGTH: 32
<212> TYPE: DNA
<213> ORGANISM: Artificial Sequence
<220> FEATURE:
<223> OTHER INFORMATION: Synthetic

<400> SEQUENCE: 131
cgcgccgagg attcccttc ccccagtggc tc                               32

<210> SEQ ID NO 132
<211> LENGTH: 31
<212> TYPE: DNA
<213> ORGANISM: Artificial Sequence
<220> FEATURE:
<223> OTHER INFORMATION: Synthetic

<400> SEQUENCE: 132
cgcgccgagg gctgggttca acggtttctg g                               31

<210> SEQ ID NO 133
<211> LENGTH: 54
<212> TYPE: DNA
<213> ORGANISM: Artificial Sequence
<220> FEATURE:
<223> OTHER INFORMATION: Synthetic

<400> SEQUENCE: 133
gtccagctat gttgtggaat cgtcgttttt ccttaaggtg tctaggtttt tctc      54

<210> SEQ ID NO 134
<211> LENGTH: 31
<212> TYPE: DNA
<213> ORGANISM: Artificial Sequence
<220> FEATURE:
<223> OTHER INFORMATION: Synthetic

<400> SEQUENCE: 134
cgcgccgagg tttgtgtgtc cttggtgtgc a                               31

<210> SEQ ID NO 135
<211> LENGTH: 49
<212> TYPE: DNA
<213> ORGANISM: Artificial Sequence
<220> FEATURE:
<223> OTHER INFORMATION: Synthetic

<400> SEQUENCE: 135
tggatgctgt caagggtgtg ccagcagctg tttctgaaga ccctgtcca            49

<210> SEQ ID NO 136
<211> LENGTH: 54
<212> TYPE: DNA
<213> ORGANISM: Artificial Sequence
<220> FEATURE:
<223> OTHER INFORMATION: Synthetic

<400> SEQUENCE: 136
ggtggaggcg acagattgtg agaactacag cagatgttat ggactcacta ggaa    54

<210> SEQ ID NO 137
<211> LENGTH: 54
<212> TYPE: DNA
<213> ORGANISM: Artificial Sequence
<220> FEATURE:
<223> OTHER INFORMATION: Synthetic

<400> SEQUENCE: 137
ggtggaggcg acagattgtg agactacagc atctgttttt gagcaccttg tcca    54

<210> SEQ ID NO 138
<211> LENGTH: 29
<212> TYPE: DNA
<213> ORGANISM: Artificial Sequence
<220> FEATURE:
<223> OTHER INFORMATION: Synthetic

<400> SEQUENCE: 138
cgcgccgagg gatcctcaaa gcgagccat    29

<210> SEQ ID NO 139
<211> LENGTH: 28
<212> TYPE: DNA
<213> ORGANISM: Artificial Sequence
<220> FEATURE:
<223> OTHER INFORMATION: Synthetic

<400> SEQUENCE: 139
cgcgccgagg ggatcctcaa agcgagcc    28

<210> SEQ ID NO 140
<211> LENGTH: 42
<212> TYPE: DNA
<213> ORGANISM: Artificial Sequence
<220> FEATURE:
<223> OTHER INFORMATION: Synthetic

<400> SEQUENCE: 140
attctgtgca caaatcaggt agcttgtagg gtcgtcgtgt tc    42

<210> SEQ ID NO 141
<211> LENGTH: 37
<212> TYPE: DNA
<213> ORGANISM: Artificial Sequence
<220> FEATURE:
<223> OTHER INFORMATION: Synthetic

<400> SEQUENCE: 141
tgcacaaatc aggcagtttg taaggtcgtt gtgtagc    37

<210> SEQ ID NO 142
<211> LENGTH: 29
<212> TYPE: DNA
<213> ORGANISM: Artificial Sequence
<220> FEATURE:
<223> OTHER INFORMATION: Synthetic

<400> SEQUENCE: 142
cgcgccgagg gagcggaacc acagcgtca    29

<210> SEQ ID NO 143

<210> SEQ ID NO 143
<211> LENGTH: 27
<212> TYPE: DNA
<213> ORGANISM: Artificial Sequence
<220> FEATURE:
<223> OTHER INFORMATION: Synthetic

<400> SEQUENCE: 143
cgcgccgagg cgagcggaac cacagcg                                27

<210> SEQ ID NO 144
<211> LENGTH: 45
<212> TYPE: DNA
<213> ORGANISM: Artificial Sequence
<220> FEATURE:
<223> OTHER INFORMATION: Synthetic

<400> SEQUENCE: 144
gggccataaa taataattat cctcatgcac aactaccggc ccgaa            45

<210> SEQ ID NO 145
<211> LENGTH: 55
<212> TYPE: DNA
<213> ORGANISM: Artificial Sequence
<220> FEATURE:
<223> OTHER INFORMATION: Synthetic

<400> SEQUENCE: 145
gaggaagaaa acgatgaact agatggagtt aatcatcatt tgctactagc tagaa   55

<210> SEQ ID NO 146
<211> LENGTH: 36
<212> TYPE: DNA
<213> ORGANISM: Artificial Sequence
<220> FEATURE:
<223> OTHER INFORMATION: Synthetic

<400> SEQUENCE: 146
cgcgccgagg gattggacaa aacgatatgt atccac                      36

<210> SEQ ID NO 147
<211> LENGTH: 31
<212> TYPE: DNA
<213> ORGANISM: Artificial Sequence
<220> FEATURE:
<223> OTHER INFORMATION: Synthetic

<400> SEQUENCE: 147
cgcgccgagg ggtccggcaa tttgtatggc c                           31

<210> SEQ ID NO 148
<211> LENGTH: 30
<212> TYPE: DNA
<213> ORGANISM: Artificial Sequence
<220> FEATURE:
<223> OTHER INFORMATION: Synthetic

<400> SEQUENCE: 148
cgcgccgagg gccatacaaa ttgccggacc                             30

<210> SEQ ID NO 149
<211> LENGTH: 32
<212> TYPE: DNA
<213> ORGANISM: Artificial Sequence
<220> FEATURE:
<223> OTHER INFORMATION: Synthetic

<400> SEQUENCE: 149

```
gaatggcgcg atttcacaac cctgaagaac gc                                    32

<210> SEQ ID NO 150
<211> LENGTH: 69
<212> TYPE: DNA
<213> ORGANISM: Artificial Sequence
<220> FEATURE:
<223> OTHER INFORMATION: Synthetic

<400> SEQUENCE: 150
agatggcgac accaatccgg agaaaaatta agacacctaa atagaaaacg aagatttcat     60
aaaatagcc                                                             69

<210> SEQ ID NO 151
<211> LENGTH: 62
<212> TYPE: DNA
<213> ORGANISM: Artificial Sequence
<220> FEATURE:
<223> OTHER INFORMATION: Synthetic

<400> SEQUENCE: 151
agatggcgac accaatccgg ctaaggcacc taacaaccaa acgaagatta cataaaatag     60
cc                                                                    62

<210> SEQ ID NO 152
<211> LENGTH: 64
<212> TYPE: DNA
<213> ORGANISM: Artificial Sequence
<220> FEATURE:
<223> OTHER INFORMATION: Synthetic

<400> SEQUENCE: 152
agatggcgac accaatccgg aactaaggca cctaaattcc aaacgaagat tcataaaat      60 agcc                                                                  64

<210> SEQ ID NO 153
<211> LENGTH: 64
<212> TYPE: DNA
<213> ORGANISM: Artificial Sequence
<220> FEATURE:
<223> OTHER INFORMATION: Synthetic

<400> SEQUENCE: 153
agatggcgac accaatccgg aattaaggca tgttaataca aaagaagat ttcaccaaat      60 agcc                                                                  64

<210> SEQ ID NO 154
<211> LENGTH: 30
<212> TYPE: DNA
<213> ORGANISM: Artificial Sequence
<220> FEATURE:
<223> OTHER INFORMATION: Synthetic

<400> SEQUENCE: 154
cgcgccgagg gttgcctttg gtccatgcat                                      30

<210> SEQ ID NO 155
<211> LENGTH: 57
<212> TYPE: DNA
<213> ORGANISM: Artificial Sequence
<220> FEATURE:
<223> OTHER INFORMATION: Synthetic
```

```
<400> SEQUENCE: 155
cagccaagcg caggcgttca ttttgtggct ctaaatgcaa tacaatgtat tgcaatc        57

<210> SEQ ID NO 156
<211> LENGTH: 60
<212> TYPE: DNA
<213> ORGANISM: Artificial Sequence
<220> FEATURE:
<223> OTHER INFORMATION: Synthetic

<400> SEQUENCE: 156
cagccaagcg caggcgctca taattttgtg gttccaaatc taaatcaatg tcacaaagtc     60

<210> SEQ ID NO 157
<211> LENGTH: 33
<212> TYPE: DNA
<213> ORGANISM: Artificial Sequence
<220> FEATURE:
<223> OTHER INFORMATION: Synthetic

<400> SEQUENCE: 157
cgcgccgagg gcaggtacac agcctataat aca                                  33

<210> SEQ ID NO 158
<211> LENGTH: 46
<212> TYPE: DNA
<213> ORGANISM: Artificial Sequence
<220> FEATURE:
<223> OTHER INFORMATION: Synthetic

<400> SEQUENCE: 158
gtcagccaag cgcaggcgta gcccttcgcc cagtgctctc ccatac                    46

<210> SEQ ID NO 159
<211> LENGTH: 50
<212> TYPE: DNA
<213> ORGANISM: Artificial Sequence
<220> FEATURE:
<223> OTHER INFORMATION: Synthetic

<400> SEQUENCE: 159
gtcagccaag cgcaggcgta cagtgccctg tgtccagtgt tctccaatgc                50

<210> SEQ ID NO 160
<211> LENGTH: 30
<212> TYPE: DNA
<213> ORGANISM: Artificial Sequence
<220> FEATURE:
<223> OTHER INFORMATION: Synthetic

<400> SEQUENCE: 160
cgcgccgagg acgtagagaa acccaggtgt                                      30

<210> SEQ ID NO 161
<211> LENGTH: 55
<212> TYPE: DNA
<213> ORGANISM: Artificial Sequence
<220> FEATURE:
<223> OTHER INFORMATION: Synthetic

<400> SEQUENCE: 161
ccaagcgcag gcgtaaggcg gtcgatgtat gtcttgttgg agatcatcaa gaact          55

<210> SEQ ID NO 162
<211> LENGTH: 50
```

<210> SEQ ID NO 163
<211> LENGTH: 33
<212> TYPE: DNA
<213> ORGANISM: Artificial Sequence
<220> FEATURE:
<223> OTHER INFORMATION: Synthetic

<400> SEQUENCE: 162
ccaagcgcag gcgtaaggca ggtcggtgtg tgtcctgttg gaaaccaact    50

<210> SEQ ID NO 163
<211> LENGTH: 33
<212> TYPE: DNA
<213> ORGANISM: Artificial Sequence
<220> FEATURE:
<223> OTHER INFORMATION: Synthetic

<400> SEQUENCE: 163
cgcgccgagg acatattcat ctgtgcttac aac    33

<210> SEQ ID NO 164
<211> LENGTH: 33
<212> TYPE: DNA
<213> ORGANISM: Artificial Sequence
<220> FEATURE:
<223> OTHER INFORMATION: Synthetic

<400> SEQUENCE: 164
tgcctgcatg ataatagatg tttgtgcgtg cat    33

<210> SEQ ID NO 165
<211> LENGTH: 42
<212> TYPE: DNA
<213> ORGANISM: Artificial Sequence
<220> FEATURE:
<223> OTHER INFORMATION: Synthetic

<400> SEQUENCE: 165
gcctagaact gcctgcgtga tagtatatgt ttgttcgtgt tt    42

<210> SEQ ID NO 166
<211> LENGTH: 42
<212> TYPE: DNA
<213> ORGANISM: Artificial Sequence
<220> FEATURE:
<223> OTHER INFORMATION: Synthetic

<400> SEQUENCE: 166
gtctggaact gccagcgtaa tagtaaatgc ttgtgcgtga ct    42

<210> SEQ ID NO 167
<211> LENGTH: 32
<212> TYPE: DNA
<213> ORGANISM: Artificial Sequence
<220> FEATURE:
<223> OTHER INFORMATION: Synthetic

<400> SEQUENCE: 167
cgcgccgagg atgagcaatt acgtgacagc tc    32

<210> SEQ ID NO 168
<211> LENGTH: 40
<212> TYPE: DNA
<213> ORGANISM: Artificial Sequence
<220> FEATURE:
<223> OTHER INFORMATION: Synthetic

<400> SEQUENCE: 168

```
tactagatat gaaacccgaa acaactgacc tacactgctc                             40
```

<210> SEQ ID NO 169
<211> LENGTH: 42
<212> TYPE: DNA
<213> ORGANISM: Artificial Sequence
<220> FEATURE:
<223> OTHER INFORMATION: Synthetic

<400> SEQUENCE: 169

```
tgttttagat ttatatcctg aaccaagtga cctattctgc tc                          42
```

<210> SEQ ID NO 170
<211> LENGTH: 26
<212> TYPE: DNA
<213> ORGANISM: Artificial Sequence
<220> FEATURE:
<223> OTHER INFORMATION: Synthetic

<400> SEQUENCE: 170

```
cgcgccgagg gtttacgact gcgacg                                            26
```

<210> SEQ ID NO 171
<211> LENGTH: 38
<212> TYPE: DNA
<213> ORGANISM: Artificial Sequence
<220> FEATURE:
<223> OTHER INFORMATION: Synthetic

<400> SEQUENCE: 171

```
gccgccacac ggacatctgg aaaaaaatat ggaaaact                               38
```

<210> SEQ ID NO 172
<211> LENGTH: 37
<212> TYPE: DNA
<213> ORGANISM: Artificial Sequence
<220> FEATURE:
<223> OTHER INFORMATION: Synthetic

<400> SEQUENCE: 172

```
ccgccacacg gacatctgta aaaaatatg gaaacct                                 37
```

<210> SEQ ID NO 173
<211> LENGTH: 30
<212> TYPE: DNA
<213> ORGANISM: Artificial Sequence
<220> FEATURE:
<223> OTHER INFORMATION: Synthetic

<400> SEQUENCE: 173

```
cgcgccgagg gcttgtccat ctggccagtc                                        30
```

<210> SEQ ID NO 174
<211> LENGTH: 54
<212> TYPE: DNA
<213> ORGANISM: Artificial Sequence
<220> FEATURE:
<223> OTHER INFORMATION: Synthetic

<400> SEQUENCE: 174

```
gctccaacgg gtttcctgct gtcacaatgt agtaattgct tgtagcttgt tctt             54
```

<210> SEQ ID NO 175
<211> LENGTH: 41
<212> TYPE: DNA
<213> ORGANISM: Artificial Sequence

```
<220> FEATURE:
<223> OTHER INFORMATION: Synthetic

<400> SEQUENCE: 175
acaacaggtt acaatgtagt aattagctgt ggcaggttgt t                    41

<210> SEQ ID NO 176
<211> LENGTH: 59
<212> TYPE: DNA
<213> ORGANISM: Artificial Sequence
<220> FEATURE:
<223> OTHER INFORMATION: Synthetic

<400> SEQUENCE: 176
gctccaacgg gtttcctgcc acacagtaac aatttggtaa ttggttgtat ctggttttt   59

<210> SEQ ID NO 177
<211> LENGTH: 30
<212> TYPE: DNA
<213> ORGANISM: Artificial Sequence
<220> FEATURE:
<223> OTHER INFORMATION: Synthetic

<400> SEQUENCE: 177
cgcgccgagg gcacgttgca gccaatatgg                                 30

<210> SEQ ID NO 178
<211> LENGTH: 46
<212> TYPE: DNA
<213> ORGANISM: Artificial Sequence
<220> FEATURE:
<223> OTHER INFORMATION: Synthetic

<400> SEQUENCE: 178
cagccaagcg caggcgccca acaaatagca ttattgtgtc cctgac                46

<210> SEQ ID NO 179
<211> LENGTH: 51
<212> TYPE: DNA
<213> ORGANISM: Artificial Sequence
<220> FEATURE:
<223> OTHER INFORMATION: Synthetic

<400> SEQUENCE: 179
cagccaagcg caggcggtta ctccaacaaa tagcattatt atggccttgt c          51

<210> SEQ ID NO 180
<211> LENGTH: 29
<212> TYPE: DNA
<213> ORGANISM: Artificial Sequence
<220> FEATURE:
<223> OTHER INFORMATION: Synthetic

<400> SEQUENCE: 180
cgcgccgagg gccacggtgt acctgcctc                                  29

<210> SEQ ID NO 181
<211> LENGTH: 25
<212> TYPE: DNA
<213> ORGANISM: Artificial Sequence
<220> FEATURE:
<223> OTHER INFORMATION: Synthetic

<400> SEQUENCE: 181
atgtccgtga ggcggcctag tgagc                                      25
```

<210> SEQ ID NO 182
<211> LENGTH: 31
<212> TYPE: DNA
<213> ORGANISM: Artificial Sequence
<220> FEATURE:
<223> OTHER INFORMATION: Synthetic

<400> SEQUENCE: 182
cgcgccgagg atgagcaatt gagtgacagc t         31

<210> SEQ ID NO 183
<211> LENGTH: 61
<212> TYPE: DNA
<213> ORGANISM: Artificial Sequence
<220> FEATURE:
<223> OTHER INFORMATION: Synthetic

<400> SEQUENCE: 183
ggtcgtgctc caacgggttt cctttagatt tggaactcga ggcaactgac ctatactgtt    60
c                                                                    61

<210> SEQ ID NO 184
<211> LENGTH: 61
<212> TYPE: DNA
<213> ORGANISM: Artificial Sequence
<220> FEATURE:
<223> OTHER INFORMATION: Synthetic

<400> SEQUENCE: 184
ggtcgtgctc caacgggttt cctttagatt tgcaacctca ggcaactgac ctatactgct    60
c                                                                    61

<210> SEQ ID NO 185
<211> LENGTH: 36
<212> TYPE: DNA
<213> ORGANISM: Artificial Sequence
<220> FEATURE:
<223> OTHER INFORMATION: Synthetic

<400> SEQUENCE: 185
cgcgccgagg ccagccctat aaataaatg tcaaac      36

<210> SEQ ID NO 186
<211> LENGTH: 60
<212> TYPE: DNA
<213> ORGANISM: Artificial Sequence
<220> FEATURE:
<223> OTHER INFORMATION: Synthetic

<400> SEQUENCE: 186
cagccaagcg caggcggcct ttaatgtata aatcgtttgg tacattttca ccaacagtat    60

<210> SEQ ID NO 187
<211> LENGTH: 58
<212> TYPE: DNA
<213> ORGANISM: Artificial Sequence
<220> FEATURE:
<223> OTHER INFORMATION: Synthetic

<400> SEQUENCE: 187
cagccaagcg caggcgcctt aatatatagg tctgtaggta ctgtttcacc tacagttt      58

<210> SEQ ID NO 188
<211> LENGTH: 28

```
<210> SEQ ID NO 188
<211> LENGTH: 28
<212> TYPE: DNA
<213> ORGANISM: Artificial Sequence
<220> FEATURE:
<223> OTHER INFORMATION: Synthetic

<400> SEQUENCE: 188
cgcgccgagg gtccggttat gcttgtcc                                28

<210> SEQ ID NO 189
<211> LENGTH: 53
<212> TYPE: DNA
<213> ORGANISM: Artificial Sequence
<220> FEATURE:
<223> OTHER INFORMATION: Synthetic

<400> SEQUENCE: 189
cagccaagcg caggcgcttg caacacaagg ttacaatatt gtaatgggct ctc       53

<210> SEQ ID NO 190
<211> LENGTH: 54
<212> TYPE: DNA
<213> ORGANISM: Artificial Sequence
<220> FEATURE:
<223> OTHER INFORMATION: Synthetic

<400> SEQUENCE: 190
cagccaagcg caggcgactg acaacaaaag gaaacgatat tgtaattgga tgtc      54

<210> SEQ ID NO 191
<211> LENGTH: 28
<212> TYPE: DNA
<213> ORGANISM: Artificial Sequence
<220> FEATURE:
<223> OTHER INFORMATION: Synthetic

<400> SEQUENCE: 191
cgcgccgagg gtccggttgt gcttgtcc                                28

<210> SEQ ID NO 192
<211> LENGTH: 53
<212> TYPE: DNA
<213> ORGANISM: Artificial Sequence
<220> FEATURE:
<223> OTHER INFORMATION: Synthetic

<400> SEQUENCE: 192
cagccaagcg caggcgcttg caacacaagg ttacaatatt gtaatgggct ctc       53

<210> SEQ ID NO 193
<211> LENGTH: 54
<212> TYPE: DNA
<213> ORGANISM: Artificial Sequence
<220> FEATURE:
<223> OTHER INFORMATION: Synthetic

<400> SEQUENCE: 193
cagccaagcg caggcgactg acaacaaaag gaaacgatat tgtaattgga tgtc      54
```